(12) United States Patent
Tan et al.

(10) Patent No.: US 10,113,065 B1
(45) Date of Patent: Oct. 30, 2018

(54) TWO-PHOTON ABSORBING COMPOUNDS AND METHODS OF MAKING SAME

(71) Applicant: The United States of America, as represented by the Secretary of the Air Force, Washington, DC (US)

(72) Inventors: Loon-Seng Tan, Centerville, OH (US); Ramamurthi Kannan, Cincinnati, OH (US)

( * ) Notice: Subject to any disclaimer, the term of this patent is extended or adjusted under 35 U.S.C. 154(b) by 0 days.

(21) Appl. No.: 15/711,084

(22) Filed: Sep. 21, 2017

Related U.S. Application Data

(60) Provisional application No. 62/415,120, filed on Oct. 31, 2016.

(51) Int. Cl.
| | |
|---|---|
| C07D 277/60 | (2006.01) |
| C07D 277/62 | (2006.01) |
| C07D 251/24 | (2006.01) |
| C07D 333/78 | (2006.01) |
| C09B 57/00 | (2006.01) |

(52) U.S. Cl.
CPC ............ *C09B 57/00* (2013.01); *C07D 251/24* (2013.01); *C07D 277/60* (2013.01); *C07D 277/62* (2013.01); *C07D 333/78* (2013.01)

(58) Field of Classification Search
CPC ... C07D 251/24; C07D 277/60; C07D 333/78
USPC ............ 544/251, 180; 548/148; 549/42, 43; 270/40
See application file for complete search history.

(56) References Cited

U.S. PATENT DOCUMENTS

| | | | |
|---|---|---|---|
| 5,770,737 | A | 6/1998 | Reinhardt et al. |
| 6,100,405 | A | 8/2000 | Reinhardt et al. |
| 6,300,502 | B1 | 10/2001 | Kannan et al. |
| 6,300,793 | B1 | 10/2001 | Ting et al. |
| 6,555,682 | B1 | 4/2003 | Kannan et al. |
| 6,730,793 | B1 | 5/2004 | Kannan et al. |
| 6,867,304 | B1 | 3/2005 | Tan et al. |
| 7,067,674 | B1 | 6/2006 | Kannan et al. |
| 7,319,151 | B1 | 1/2008 | Tan et al. |
| 8,153,812 | B1 | 4/2012 | Tan et al. |
| 8,318,888 | B1 | 11/2012 | Tan et al. |
| 8,471,035 | B1 | 6/2013 | Tan et al. |
| 8,580,958 | B1 | 11/2013 | Tan et al. |
| 8,735,528 | B1 | 5/2014 | Tan et al. |
| 8,895,730 | B2 | 11/2014 | Tan et al. |
| 9,024,037 | B1 | 5/2015 | Tan et al. |

OTHER PUBLICATIONS

Pawlicki, Two-Photon Absorption and the Design of Two-Photon Dyes, Angew. Chem. Int. Ed. 2009, 48, 3244-3266.
He, Multiphoton Absorbing Materials: Molecular Designs, Characterizations, and Applications, Chem. Rev. 2008, 108, 1245-1330.
Kannan, Toward Highly Active Two-Photon Absorbing Liquids; Synthesis and Characterization of 1,3,5-Triazine-Based Octupolar Molecules, Chem. Mater. 2004, 16, 185-194.
Kannan, Diphenylaminofluorene-Based Two-Photon-Absorbing Chromophores with Various pi-Electron Acceptors, Chem. Mater. 2001, 13, 1896-1904.
Jhaveri, Direct Three-Dimensional Microfabrication of Hydrogels via Two-Photon Lithography in Aqueous Solution, Chem. Mater., vol. 21, No. 10, 2009.
Belfield, Multiphoton-absorbing organic materials for microfabrication, emerging optical applications and non-destructive three-dimensional imaging, J. Phys. Org. Chem. 2000; 13: 837-849.
Sadighi, A Highly Active Palladium Catalyst System for the Arylation of Anilines, Tetrahedron Letters 39 (1998) 5327-5330.
Makarov, Impact of Electronic Coupling, Symmetry, and Planarization on One and Two-Photon Properties of Triarylamines with One, Two, or Three Diarylboryl Acceptors, J. Phys. Chem. A 2012, 116, 3781-3793.

(Continued)

*Primary Examiner* — Venkataraman Balasubramanian

(57) ABSTRACT

A two-photon absorbing (TPA) compound is provided, along with a method of making same. The TPA compound has a general structural formula:

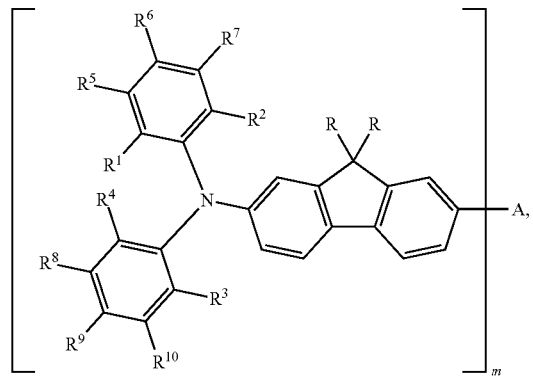

where A is an acceptor moiety that is connected to m number of diarylaminofluorene arms (m=1-3); in each diarylaminofluorene arms, R is selected from linear or branched alkyl chains having a general formula $C_nH_{2n+1}$, where n is in a range from 2 to 25; where $R^1$, $R^2$, and $R^3$ are independently selected from H or $C_1$-$C_4$ alkyls; where $R^4$ is selected from $C_1$-$C_5$ alkyls; and wherein $R^5$ through $R^{10}$ are independently selected from H, alkoxyls, alkyls, or aryls. A may be benzothiazol-2-yl, benzo[1,2-d:4,5-d']bisthiazole-2,6-diyl, thiazolo[5,4-d]thiazole-2,5-diyl-, 1,3,5-triazine-2,4,6-triyl, 1,3,5-triazine-2,4,6-triyl, benzo[1,2-d:3,4-d':5,6-d"]tristhiazole-2,5,8-triyl-, or dithieno[3,2-b:2',3'-d]thiophene-2,6-diyl-.

20 Claims, 19 Drawing Sheets

(56) References Cited

OTHER PUBLICATIONS

Rogers, Understanding the One-Photon Photophysical Properties of a Two-Photon Absorbing Chromophore, J. Phys. Chem. A 2004, 108, 5514-5520.
Stewart, Steric hindrance inhibits excited-state relaxation and lowers the extent of intramolecular charge transfer in two-photon absorbing dyes, Phys.Chem.Chem.Phys., 2016, 18, 5587.
Reguardati, High-accuracy reference standards for two-photon absorption in the 680-1050 nm wavelength range, Optics Express 9054, Apr. 18, 2016, vol. 24, No. 8.

TWO-PHOTON ABSORBING COMPOUNDS AND METHODS OF MAKING SAME

CROSS REFERENCE TO RELATED APPLICATIONS

This application claims the benefit under 35 U.S.C. § 119(e) of U.S. Provisional Patent Application Ser. No. 62/415,120 filed on Oct. 31, 2016, and titled Two-Photon Absorbing Compounds and Methods of Making Same, the entire content of which is incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention is directed to two-photon active compounds, and more particularly to two-photon active compounds with a dipolar structure and bearing multialkyl-substituted diaryl amino moieties, as well as methods of making such compounds.

BACKGROUND OF THE INVENTION

Two-photon absorption (TPA) occurs through the simultaneous absorption of two or more photons via virtual states in an absorbing medium. For a given chromophore, TPA processes take place at wavelengths much longer than the cut-off wavelength of its linear (single-photon) absorption. In the case of TPA, two quanta of photons may be absorbed from a single light source (degenerate TPA) or two sources of different wavelengths (non-degenerate TPA).

Although multiphoton absorption processes have been known since 1931, this field remained dormant largely due to the lack of TPA-active materials with sufficiently large cross-sections. In the mid-1990s, several new classes of chromophores exhibiting very large effective TPA cross-section values, which are generally reported in $GM=1\times10^{-50}$ $cm^4$ s $photon^{-1}$, were reported. In conjunction with the increased availability of ultrafast high-intensity lasers, the renewed interest has not only sparked a flurry of activities in the preparation of novel dye molecules with enhanced TPA cross-section values, but also many previously-conceived applications based on the TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis up-conversion; (b) deeper penetration of incident light; (c) highly localized excitation allowing precision control of in-situ photochemical events in the absorbing medium, thereby minimizing undesirable activities such as photodegradation or photobleaching; and (d) fluorescence when properly manipulated allows information feedback. It is anticipated that further ingenious utilizations of these basic characteristics will lead to new practical applications in addition to those already under investigation, e.g., fluorescence imaging, data storage, eye and sensor protection, microfabrication of microelectromechanical systems (MEMS), photodynamic therapy, etc.

Although enhancement of TPA cross-section values have been reported, these results are mostly limited to relatively narrow wavelength ranges or longer (red-shifted) wavelengths, invariably derived from dilute solutions, and cannot be directly translated to solid-state systems, where confinement, severely restricted mobility, and undesired interactions with the matrix environment would significantly affect the linear and nonlinear optical properties of the chromophore. A potentially feasible approach to broadening the TPA wavelength range in solid state systems would be blending two or more TPA chromophores that are structurally similar and phase-compatible, but sensitive in complementary parts of the electromagnetic spectrum.

Accordingly, there is a need for new TPA compounds, as well as methods of making them.

SUMMARY OF THE INVENTION

The present invention overcomes one or more of the foregoing problems and other shortcomings, drawbacks, and challenges of two-photon absorbing compounds. While the invention will be described in connection with certain embodiments, it will be understood that the invention is not limited to these embodiments. To the contrary, this invention includes all alternatives, modifications, and equivalents as may be included within the spirit and scope of the present invention.

In accordance with an embodiment of the present invention, a two-photon active compound is provided, having a general structural formula:

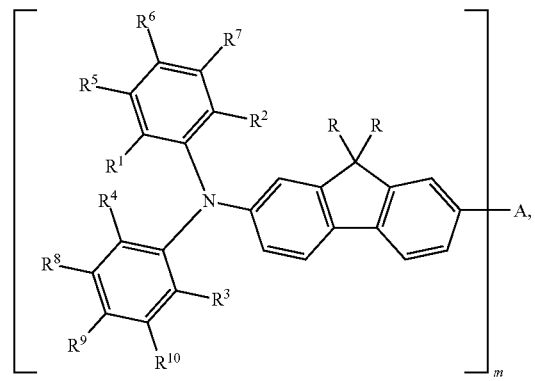

wherein A is an acceptor moiety that is connected to m number of diarylaminofluorene arms (m=1-3); in each diarylaminofluorene arms, R is selected from linear or branched alkyl chains having a general formula $C_nH_{2n+1}$, where n is in a range from 2 to 25; wherein $R^1$, $R^2$, and $R^3$ are independently selected from the group consisting of H and $C_1$-$C_5$ alkyls; wherein $R^4$ is selected from the group consisting of $C_1$-$C_5$ alkyls; and wherein $R^5$ through $R^{10}$ are independently selected from the group consisting of H, alkoxyls, alkyls, and aryls.

In another embodiment, A is selected from the group consisting of: benzothiazol-2-yl, benzo[1,2-d:4,5-d']bisthiazole-2,6-diyl, thiazolo[5,4-d]thiazole-2,5-diyl-, dithieno[3,2-b:2',3'-d]thiophene-2,6-diyl-, 1,3,5-triazine-2,4,6-triyl, benzo[1,2-d:3,4-d':5,6-d"]tristhiazole-2,5,8-triyl-, and benzo[1,2-b:3,4-b':5,6-b"]trithiophene-2,5,8-triyl

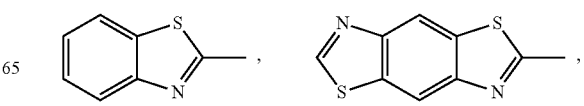

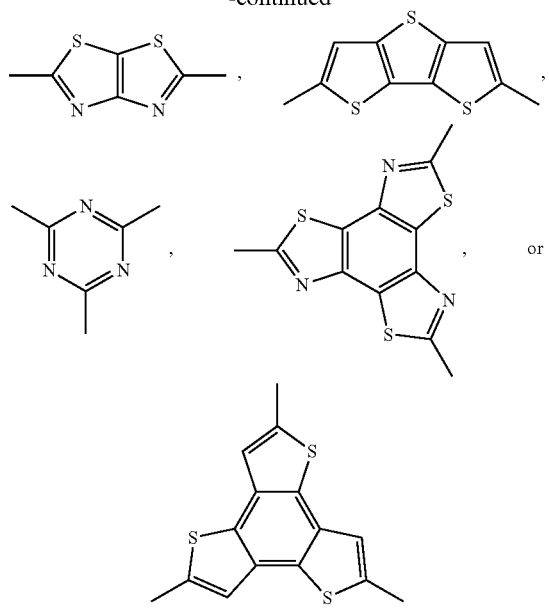

but A is not limited to those compounds.

In accordance with another embodiment, the acceptor moiety (A) is a benzothiazole moiety, whereby the two-photon active compound has a general structural formula:

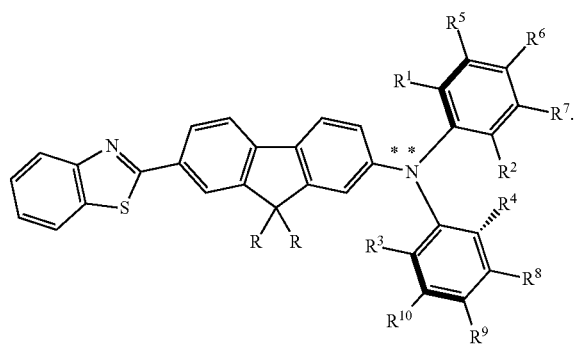

In accordance with another embodiment, a method of synthesizing the two-photon active compound is provided. The method includes reacting an amino-fluorene derivative having a general formula:

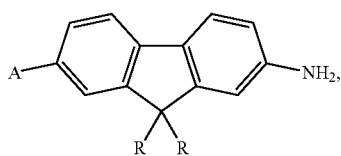

with an ortho-substituted aryl halide in the presence of a catalyst, wherein the ortho-substituted aryl halide comprises a $C_1$-$C_5$ alkyl substituent positioned ortho to a halide on a phenyl moiety.

In accordance with another embodiment, another method of synthesizing the two-photon active compound is provided. The method includes reacting a halo-fluorene derivative having a general formula:

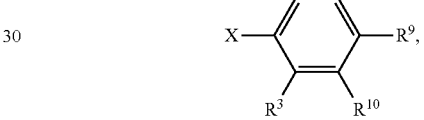

with an aniline derivative having a general formula:

$$H_2N\!-\!\!\underset{R^1\ \ \ R^7}{\overset{R^2\ \ \ R^5}{\bigcirc}}\!\!-\!R^6,$$

in the presence of a first catalyst to form a monoaryl-substituted amino fluorene derivative; and reacting the monoaryl-substituted amino fluorene derivative with an ortho-substituted aryl halide having a general formula:

$$X\!-\!\!\underset{R^3\ \ \ R^{10}}{\overset{R^4\ \ \ R^8}{\bigcirc}}\!\!-\!R^9,$$

where X is bromide or iodide, in the presence of a second catalyst. The catalyst(s) suitable for carrying out the foregoing methods may comprise palladium or copper.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention. It will be appreciated that for purposes of clarity and where appropriate, reference numerals have been repeated in the figures to indicate corresponding structures or features.

DETAILED DESCRIPTION OF THE INVENTION

The composition and synthesis of a series of two-photon active molecules with donor-π-acceptor (dipolar) structure and bearing multialkyl subsitituents at the ortho-positions of the donating diphenylamino moiety are described. Introducing the ortho-substitution chemistry into the phenyl rings of the donating diphenylamino moiety of an exemplary system enables the derivative molecules to blue-shift two-photon sensitivity (relative to the un-substituted variant), while preserving their linear optical properties.

In accordance with an embodiment of the present invention, a class of two-photon absorbing (TPA) compounds is provided, having a general formula:

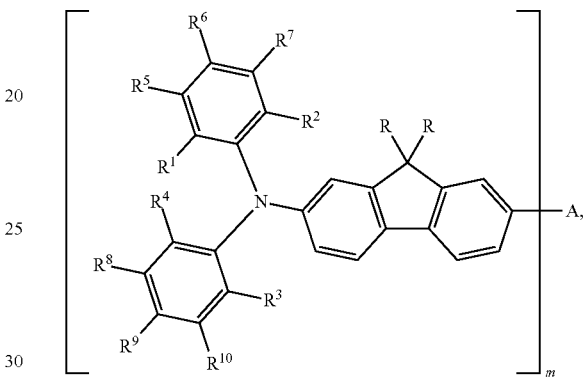

wherein A is an acceptor moiety connected to m number of diarylamino-fluorene arms (m=1-3); wherein R is selected from linear or branched alkyl chains having a general formula $C_nH_{2n+1}$, where n is in a range from 2 to 25 carbons; wherein $R^1$, $R^2$, and $R^3$ are independently selected from the group consisting of H and $C_1$-$C_5$ alkyl groups; wherein $R^4$ is selected from the group consisting $C_1$-$C_5$ alkyl groups; and wherein $R^5$ through $R^{10}$ are independently selected from the group consisting of H, alkoxyls, alkyls, and aryls.

In another embodiment, non-limiting examples of the acceptor group A include: benzothiazol-2-yl, benzo[1,2-d:4,5-d']bisthiazole-2,6-diyl, thiazolo[5,4-d]thiazole-2,5-diyl-, dithieno[3,2-b:2',3'-d]thiophene-2,6-diyl-, 1,3,5-triazine-2,4,6-triyl, benzo[1,2-d:3,4-d':5,6-d'']tristhiazole-2,5,8-triyl-, and benzo[1,2-b:3,4-b':5,6-b']trithiophene-2,5,8-triyl

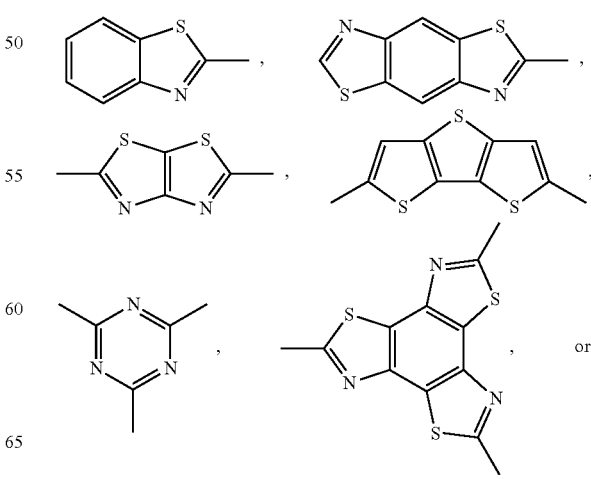

-continued

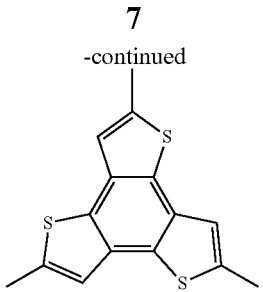

In an embodiment, the acceptor group is a benzothiazole moiety, whereby the two-photon active compound has a general structural formula:

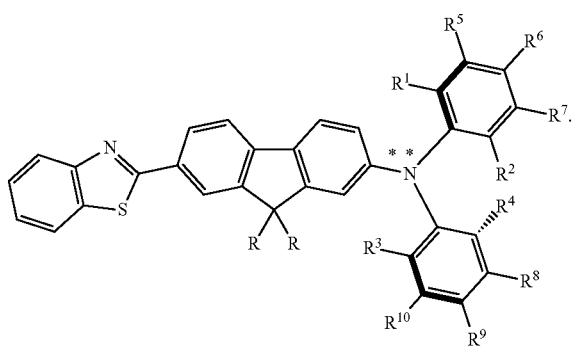

Regarding the linear or branched alkyl chains having a general formula $C_nH_{2n+1}$, non-limiting examples include ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl, pentacosyl, and isomeric forms thereof. In one aspect, n may be in a range from 6 to 20, or in a range from 10 to 15. In the examples, ethyl was utilized, but the linear or branched alkyl chains may be varied to change solubility properties of the final TPA compounds.

In another aspect, the $C_1$-$C_5$ alkyl groups may be methyl, ethyl, n-propyl, isopropyl, n-butyl, isobutyl, tert-butyl, n-pentyl, isopentyl, or neopentyl.

In yet another aspect, $R^5$ through $R^{10}$ may be H, alkoxyls (e.g., $C_1$-$C_5$ alkoxyls), alkyls (e.g., $C_1$-$C_5$ alkyls), substituted phenyls, or unsubstituted phenyls. In one aspect, $R^5$ through $R^{10}$ may be H.

Figure 1:
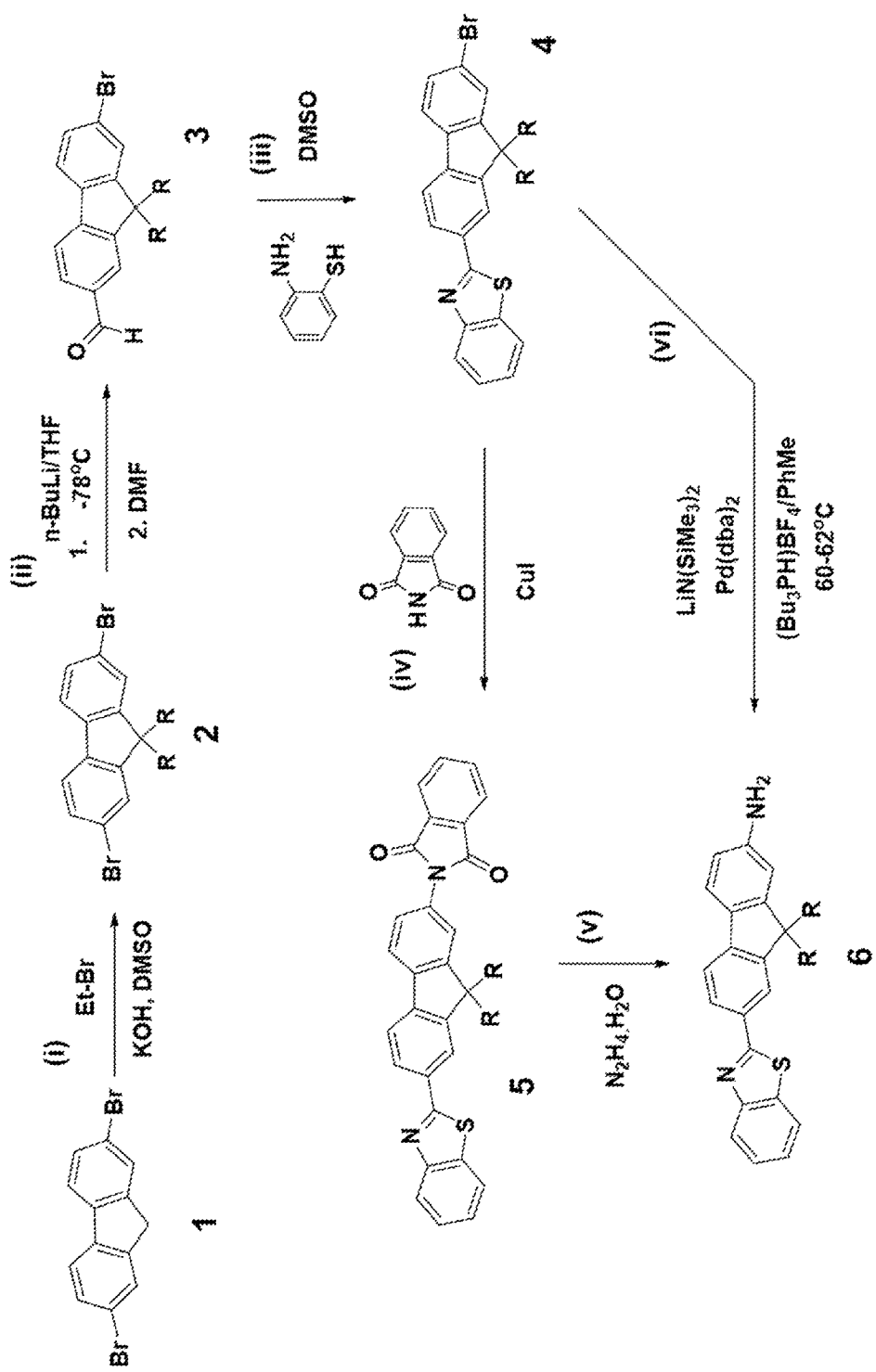
FIG. 1 is a synthetic scheme outlining exemplary preparative routes to precursors 4 and 6, which may be utilized in synthesizing a two photon absorbing (TPA) compound, in accordance with an embodiment of the present invention.

FIG. 1 is a synthetic scheme outlining exemplary preparative routes to precursor compounds 4 and 6, which may be utilized in synthesizing a two-photon absorbing (TPA) compound, in accordance with an embodiment of the present invention. With reference to FIG. 1, two exemplary precursors (compounds 4 and 6) may be utilized to form the TPA compounds of the present invention starting from 2,7-dibromofluorene 1. Linear or branched alkyl chains (R) may be introduced into the C9 position of 2,7-bromofluorene 1 by reacting (i) with at least two equivalents of the corresponding linear or branched alkyl halide (R—X, where X may be chloro, bromo, or iodo) under basic conditions. A formyl group may be introduced into the resulting dialkylated product 2 by mono-lithiation with n-butyllithium (ii) and quenching with dimethylformamide to provide 9,9-dialkyl-7-bromo-fluorene-2-carboxaldehyde 3. Treatment of 3 with 2-am inothiophenol at elevated temperature (iii) provides 2-(7-bromo-9,9-dialkylfluoren-2-yl)benzothiazole 4.

With continued reference to FIG. 1, a palladium-catalyzed amination (vi) of precursor 4 with bis(trimethylsilyl)amide in the presence of tri-t-butylphosphonium tetrafluoroborate, followed by an acidic work up to effect desilylation, provides precursor 2-(7-amino-9,9-dialkylfluoren-2-yl)benzothiazole 6. Alternatively, precursor 4 may be converted to precursor 6 by a two-step process, where precursor 4 is subject to Ullmann conditions (iv) (potassium phthalimide, CuI) to form 2-(7-phthalimido-9,9,-dialkylfluoren-2-yl)benzothiazole 5, which upon treatment with hydrazine hydrate (v) forms phthalhydrazide thereby liberating the desired 2-(7-amino-9,9-dialkylfluoren-2-yl)benzothiazole 6.

Figure 2:
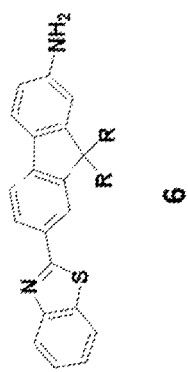
FIG. 2 is a schematic showing a method for synthesizing exemplary TPA compounds of the present invention, in accordance with an embodiment of the present invention.
Figure 2:
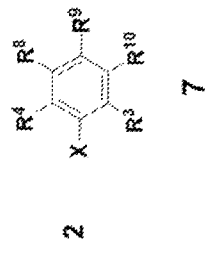
Figure 2:
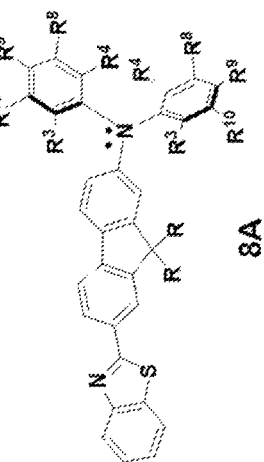
Figure 3:
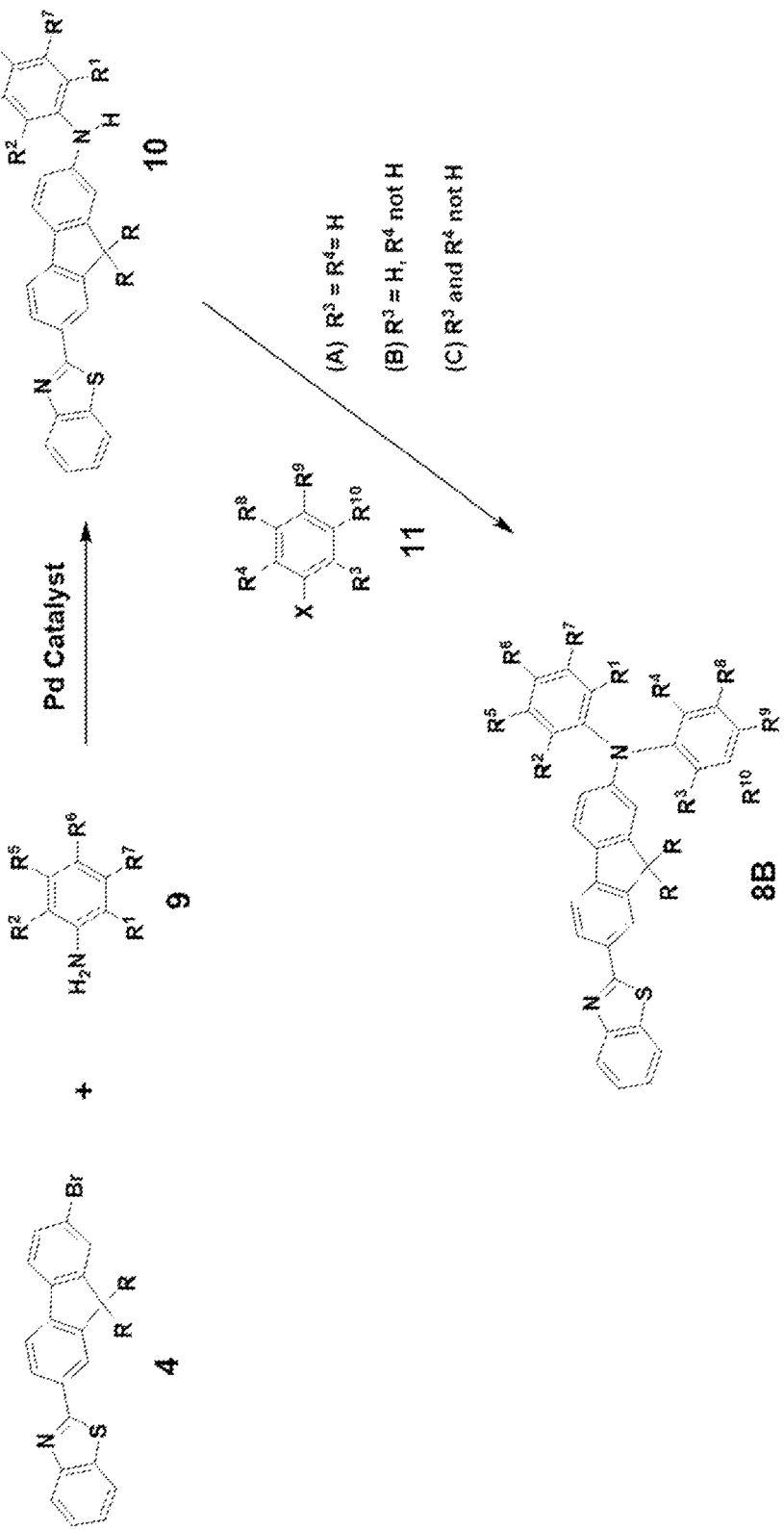
FIG. 3 is a schematic showing a complementary method for synthesizing exemplary TPA compounds of the present invention relative to the method shown in FIG. 2, where mono-, di-, tri-, and tetra-ortho alkylated TPA compounds are prepared via a mono-aminated intermediate, in accordance with an embodiment of the present invention.

FIG. 2 is a schematic showing a method for synthesizing exemplary TPA compounds of the present invention, in accordance with an embodiment of the present invention. FIG. 3 is a schematic showing a complementary method for synthesizing exemplary TPA compounds of the present invention relative to the method shown in FIG. 2, where mono-, di-, tri- and tetra-ortho alkylated TPA compounds are prepared via a mono-aminated intermediate, in accordance with an embodiment of the present invention. With reference to FIGS. 2 and 3, the TPA compounds of the present invention may be realized by two complementary approaches. A first approach (shown in FIG. 2) involves a direct bis-N-arylation of 2-(7-amino-9,9-dialkylfluoren-2-yl)benzothiazole 6, which may be facilitated by a palladium-catalyzed reaction with at least two equivalents of a mono-ortho-substituted halobenzene 7 to directly bis-arylate the nitrogen and provide the TPA compound 8A. Due to the incorporation of two mono-ortho-substituted aryl groups, the resultant TPA compound 8A may be considered a di-ortho alkylated TPA compound. Non-limiting examples of mono-ortho or di-ortho-halobenzenes include 2-methyl bromobenzene, 2,6-dimethyl bromobenzene, 2-ethyl bromobenzene, 2,6-diethyl bromobenzene, 2-propyl bromobenzene, 2-isopropyl bromobenzene, 2-butyl bromobenzene, 2-isobutyl bromobenzene, 2-tert-butyl bromobenzene, 2-methyl iodobenzene, 2,6-dimethyl iodobenzene, 2-ethyl iodobenzene, 2,6-diethyl bromobenzene, 2-propyl iodobenzene, 2-isopropyl iodobenzene, 2-butyl iodobenzene, 2-isobutyl iodobenzene, or 2-tert-butyl iodobenzene.

In the complementary two-step approach shown in FIG. 3, 2-(7-bromo-9,9-dialkylfluoren-2-yl) benzothiazole 4 may be first coupled to the desired aniline derivative 9 in the presence of a catalyst, e.g. Pd or Cu, to form a mono-arylated amino-fluorenyl benzothiozole derivative 10. Aniline derivative 9 may vary in ortho substitution, relative to the halide, having zero, one, or both ortho positions alkyl-substituted. Palladium-catalyzed or copper-catalyzed N-arylation of derivative 10 with at least one equivalent of a halobenzene 11 affords the desired TPA compound 8B. Halobenzene 9 may vary in ortho substitution, relative to the halide, having zero, one, or both ortho positions alkyl-substituted.

In continued reference to FIG. 3, the complementary two-step approach is further described to illustrate how the TPA compound 8B of the present invention may be mono-, di-, tri-, or tetra-ortho substituted. Mono-ortho substituted TPA compound 8B may be realized starting from 2-(7-bromo-9,9-dialkylfluoren-2-yl) benzothiazole 4, which is sequentially coupled to the desired aniline derivative 9, and then the resulting product 10 coupled to the desired halobenzene 11, where only one of $R^1$, $R^2$, $R^3$, or $R^4$ is a C1-C4 alkyl group, and the remaining are all H. Di-ortho substituted TPA compound 8B may be prepared, where both aniline derivative 9 and halobenzene 11 are mono-ortho substituted. Alternatively, one of the aniline derivative 9 or halobenzene 11 may be di-ortho substituted, while the other has no other substituents. Tri-ortho substituted TPA compound 8B may be prepared, where one of the aniline derivative 9 or halobenzene 11 is di-ortho substituted, while the other has only one ortho-substituent. A tetra-ortho substituted TPA compound 8B may be derived using di-ortho substituted aniline derivative 9 and di-ortho substituted halobenzene 11.

Amination Reaction Conditions

The synthesis of desired triarylamines can be accomplished by either (i) the classical Ullmann reaction of a diarylamine and an arylbromide or aryliodide, which generally is conducted with copper and an inorganic base (e.g. potassium carbonate), under solvent-less and high temperature (typically approaching 200° C.) conditions or (ii) milder catalysis based on numerous Pd-phosphine complexes and in the presence of a base to scavenge the hydrogen halide by-product.

Palladium Catalyst Systems:

Bis[2-(diphenylphosphino)phenyl] ether (DPEphos) is claimed to be a suitable ligand with palladium acetate and sodium t-butoxide in toluene to make sterically crowded hindered diarylamines (not triarylamines) by Buchwald et al. One of the compounds reported in the work of Buchwald et al., 2,6-diisopropyl-2'-dimethyl diphenylamine, was made in high yields as reported. These reaction conditions were used in the reactions between bromofluorenyl benzothiazole (4) and 2,6-dialkyl substituted anilines and 2-t-butylaniline, $ArNH_2$ (Ar=2,6-dimethyl, 2,6-diethyl, 2,6-diisopropylphenyl and 2-t-butylphenyl) to make the arylamino fluorenylbenzothiazoles, i.e. the secondary amine intermediates (10). The only monoalkyl phenylamino benzothiazole made in this study, the 2-isopropyl compound (10, R=Et, $R^1$=iPr, $R^2$-$R^7$=H) was made from the bromofluorenyl benzothiazole and 2-isopropylaniline. Except for 2,2'-di-tert-butyl substituted chromophore, all other disubstituted chromophores with 2,2'- and 2,6-disubstitution (methyl, ethyl and isopropyl) were accessed using a $Pd(dba)_2$ and 2-(di-t-butylphosphino)biphenyl combination. Being more basic, 2-(di-t-butylphosphino)biphenyl and tri-t-butyl phosphine are more suitable for aminations of less reactive aryl chlorides than most others.

The hindered 2,6-diisopropyl-2'-methyldiphenyl amine on reaction with bromofluorenyl benzothiazole (4), with the biphenyl phosphine and $Pd(dba)_2$ gave 70% yield of t-butoxyfluorenyl benzothiazole and no amination product. The logical extension of this observation is to examine non-nucleophilic bases such as cesium carbonate. This was tried albeit with a different substrate. Thus, 2-ethyl bromobenzene was reacted with 2,6-diethylphenylamino benzothiazole (10; R,$R^1$,$R^2$=Et; $R^5$-$R^7$=H) in toluene with palladium acetate, tri-t-butyl phosphonium tetrafluoroborate and cesium carbonate. While there was mass spectral evidence for the formation of the desired triarylamine, after 20 hours at 100° C., the reaction returned mostly the starting arylaminophenyl benzothiazole (10).

A reaction between the same substrates, 2,6-diethylphenylamino benzothiazole and 2-ethyl bromobenzene, in NMP with potassium carbonate as the base and a mixture of copper (I) iodide and copper after 3 days at reflux resulted only in recovering most of the benzothiazole starting material, albeit mass spectral result suggesting formation of some desired product. 2,6-Diisopropyl-2'-methyldiphenylamine also failed to react with 7-bromo-9,9-diethylfluorenyl-2-benzothiazole (4) in xylenes with potassium t-butoxide as the base and bipyridine as the ligand for copper (I) iodide catalyst. In contrast, the tetramethyl chromophore (AF-331-22, Table 1 below) was obtained in 20% yield using 2-bromo-o-xylene and copper, copper iodide catalyst in DMAC in their reaction with the dimethylphenylamino benzothiazole precursor (10, $R^1$=$R^2$=Me, $R^3$=$R^4$=$R^5$=H; Example 10) after 5 days at reflux.

Ullmann Conditions:

Classical Ullmann conditions of reaction utilize copper metal, an amine compound, an iodoarene compound, and a base. The iodoarene compound can undergo many side reactions such as reduction to arene and reductive dimerization to biaryl. However, these iodoarene-derived by-products are generally inert and easily removable. Thus, by using a large excess (e.g., two or more equivalents) of iodoarene, there is generally sufficient iodoarene to give the desired product. Most of the tri- and tetra-alkyl ortho-substituted, as well as the di-t-butyl ortho,ortho-substituted derivatives were made using copper catalysis in moderate to low yields.

Steric Effect of Ortho-Substitution:

Based on the premise that extended planar geometry would provide maximal π-π orbital overlap, creating high "ortho-congestion" in one or both phenyl rings severely limits free C—N bond rotation so much so that their dihedral angles with a fluorene plane will be <<44° (which is the mean value observed in the crystal structure of triphenylamine with a 3-blade propeller shape). This can be considered as the lowest limit of π-π overlapping of nitrogen lone-pair and phenyl aromatic system.

Two opposite outcomes are possible. On one hand, the resulting steric effect forces the phenyl rings to move away from the nitrogen lone pair, causes greater overlap with the π-system of fluorene, and in turn a greater degree of intramolecular charge (IMC) transfer to the acceptor (e.g., benzothiazole moiety).

Figure 4:
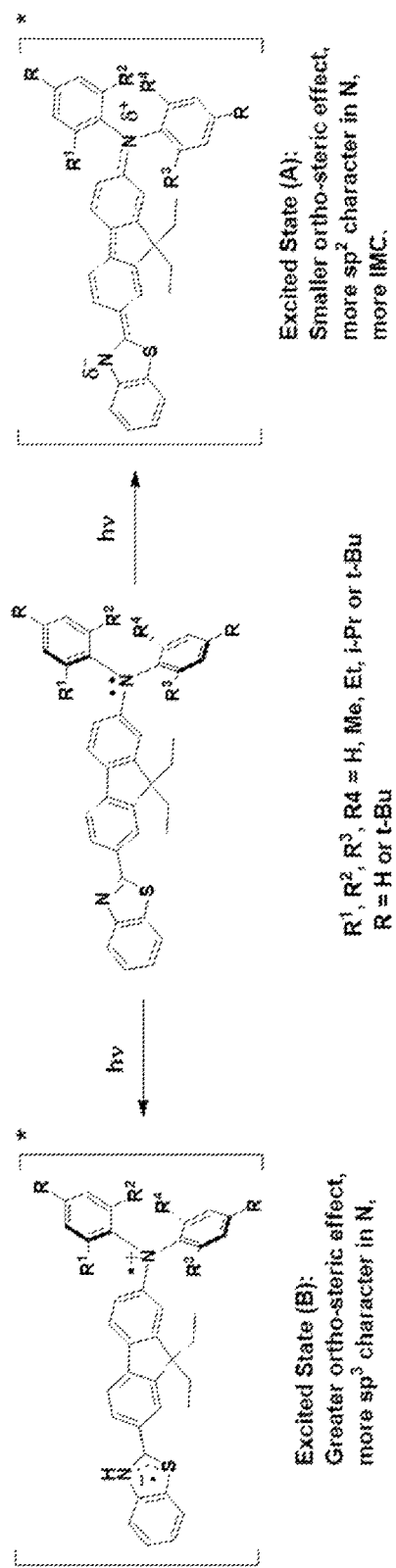
FIG. 4 is a schematic show two possible complementary excited states (A and B) in response to ortho-steric effect of TPA compounds bearing a diphenylamino donor group.

Conversely, as depicted in FIG. 4, steric congestion around nitrogen forces its hydridization to go from orbital-character that is more $sp^2$ (trigonal planar, Excited State A) to more $sp^3$ (tetrahedral, Excited State B) in order to minimize nitrogen's lone-pair and bond-pairs repulsion in accordance with valence shell electron pair repulsion (VSEPR) theory, as well as steric interactions between the alkyl group and fluorene-hydrogen. Excited State B would effectively reduce the π-electron density for IMC process from nitrogen to the acceptor (e.g., benzothiazole) upon photonic excitation. As the effective length of conjugation in the excited state (B) is reduced compared to excited state (A), this results in 2PA peak being blue-shifted with concomitant reduction in cross-section value.

Figure 13:
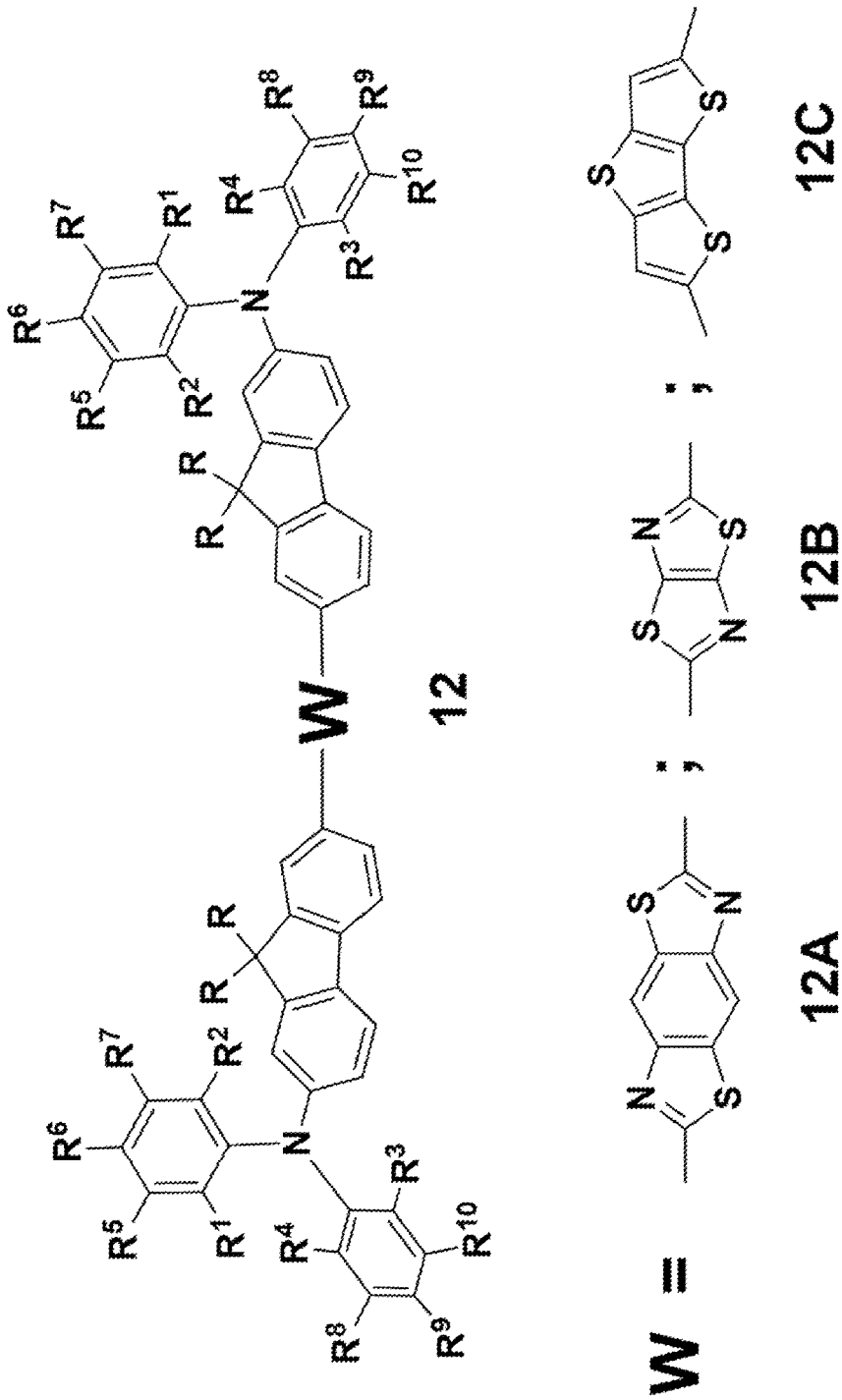
FIG. 13 shows exemplary quadrupolar TPA compounds (12A, 12B, 12C) with a sterically-hindered triaryamino endgroups and electron-accepting central hubs.
Figure 14:
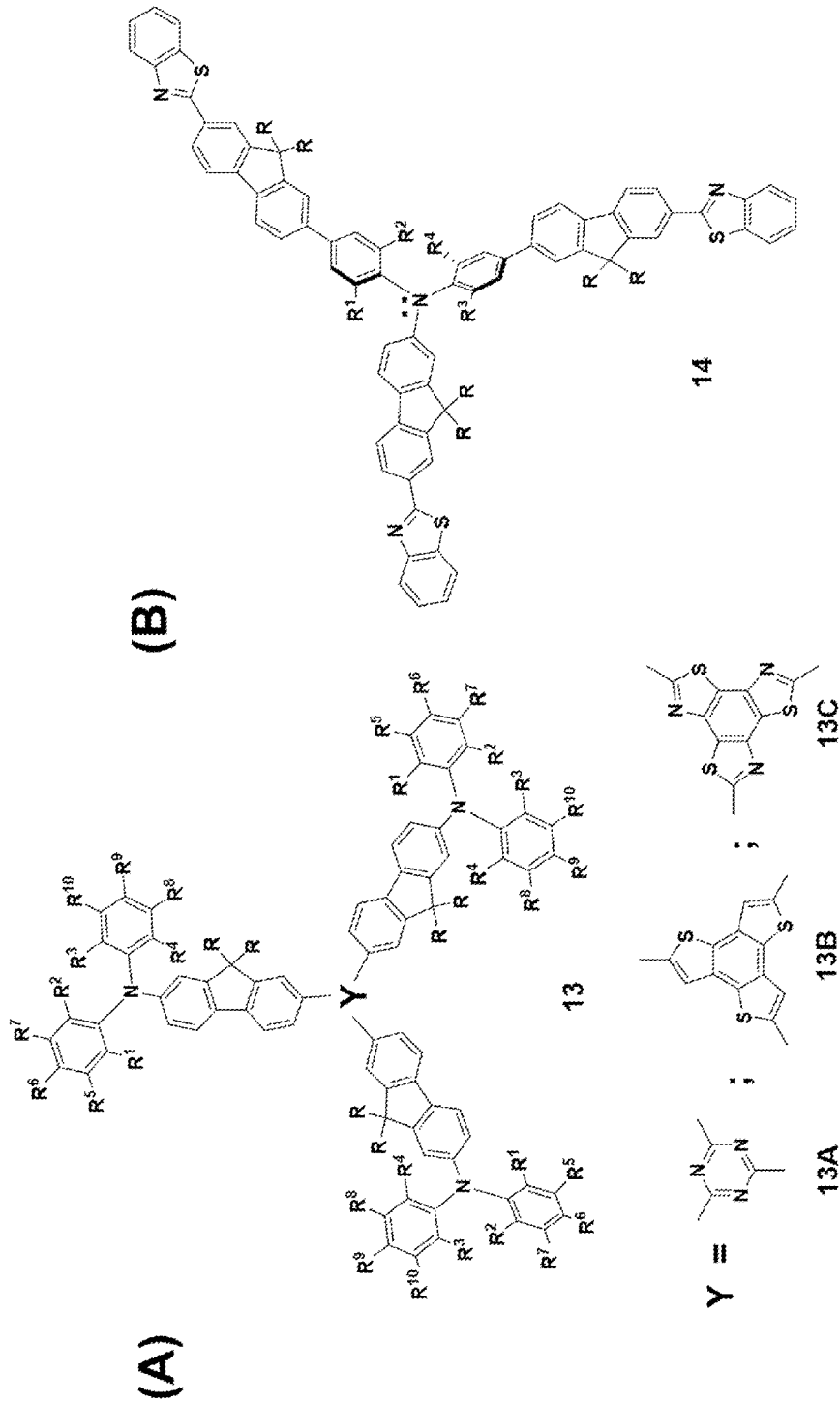
FIG. 14 shows exemplary octupolar TPA compounds: (A) structures (13A, 13B, 13C) with a sterically-hindered triaryamino endgroups as terminal groups and electron-accepting hubs (Y moieties); and (B) structure 14 with a sterically hindered triaryamino endgroups as the electron-donating hub and the terminal benzothiazole groups as electron-accepting groups.

Because of the systematic nature of our study, it is anticipated that the favorable results may provide the basis for a molecular design tool to blue-shift the 2PA peak of other related AFX molecules (see Table 1 below) of the quadrupolar and octupolar types, with little or no peak-shifting consequence on linear optical transition. The representative examples for quadrupolar-structure and octupolar-structure, which are known to have much higher two-photon sensitivity in the near-IR region, are depicted in FIG. 13 and FIG. 14, respectively. The methods for preparing these TPA compounds are outlined in FIGS. 15-18.

Figure 15:
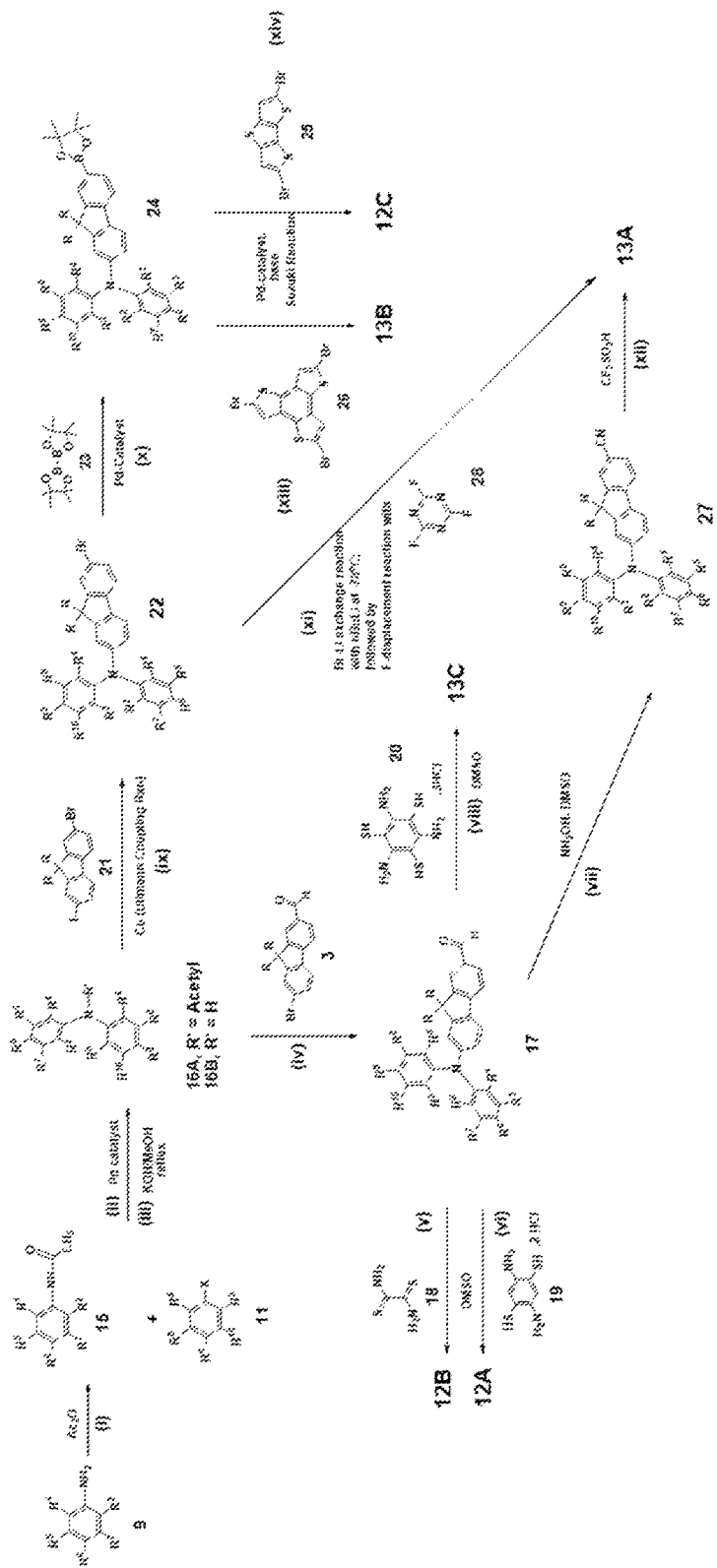
FIG. 15 is a schematic showing general methods for synthesizing TPA compounds with a sterically-hindered amino moiety as the terminal groups of quadrupolar (12A, 12B, 12C) and octupolar (13A, 13B, 13C) structures.

A general strategy is to construct the triarylamine-containing 'arm' first, followed by coupling it to a quadrupolar or an octupolar core. Two pathways to accomplish this construction are feasible. With reference to FIG. 15, the syntheses of quadrupolar molecules 12A, 12B, and 12C (see FIG. 13), as well as octupolar molecules 13A, 13B, and 13C (see FIG. 14), are briefly described as follows. In these molecules, sterically-hindered triarylamino groups are situated at the ends. Towards successful construction of these quadrupolar and octupolar molecules, the following reactions are ideal for the last steps:

(I) for molecules 12A, 12B, and 13C via oxidative-condensation reactions (i.e. (v), (vi), and (viii)) in DMSO of formyl (aldehyde)-functionalized triarylamino-fluorene-arm (compound 17) with 2,5-diamino-1,4-benzenedithiol dihydrochloride (compound 19), dithiooxamide (compound 18), and triaminobenzene-1,3,5-trithiol (compound 20; CAS#96069-48-6);

(II) for molecules 12C and 13B via multiple Suzuki Pd-catalyzed coupling reaction (i.e., (xiii), (xiv)) between the boronate-functionalized triarylamino-fluorene-arm and 2,6-dibromodithieno[3,2-b:2',3'-d]thiophene (compound 25; CAS#67061-69-2) and 2,5,8-tribromobenzo[1,2-b:3,4-b':5, 6-b"]trithiophene (compound 26; CAS #1174223-26-7);

(III) for molecule 13A via either a superacid-catalyzed cyclotrimerization (step xii) of nitrile-functionalized triarylamino-fluorene-arm (compound 27) to form the respective s-triazine core or via triple aromatic nucleophilic substitution reaction (xi) of 2,4,6-trifluoro-s-triazine by 7-lithiated triarylamino-fluorene arm (derived from compound 22). These methods for 13A are exemplified by the experimental preparation of AF452-2,2'-6iPr and AF452-2,6-6iPr that are depicted in FIG. 16 and FIG. 17, respectively.

Figure 16:
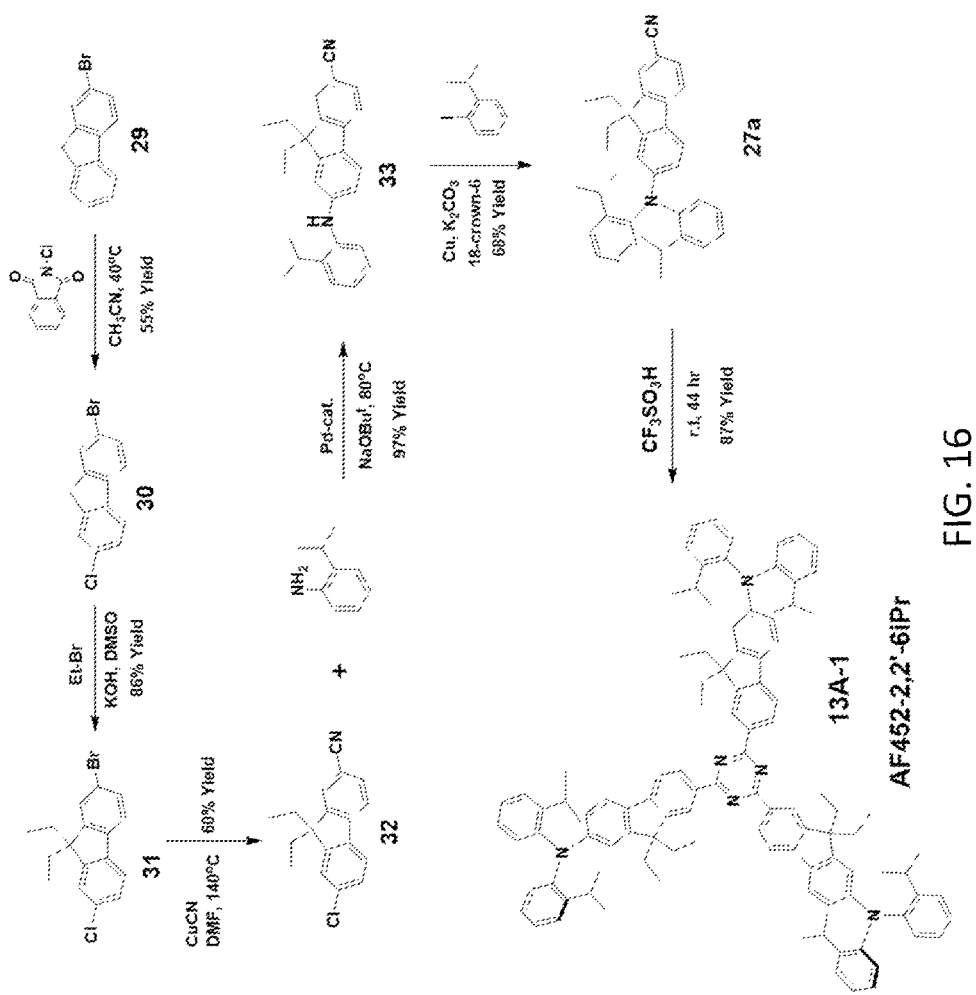
FIG. 16 is a schematic showing a representative method that features the use of an acid-catalyzed cyclotrimerization to synthesize an octupolar TPA compound with a sterically-hindered amino as the terminal groups and 1,3,5-triazine-hub (13A-1)

With reference to FIG. 16, the preparative details of compound 13A-1 ($R^1=R^2$=isopropyl, $R^3=R^4=R^5=R^6=R^7=R^8=R^9=R^{10}$=H) are provided as Examples-32-35 (see below). In this specific example (compound 13A-1=AF452-2,2'-6iPr), an alternative route was used to construct the nitrile-functionalized triarylamino-fluorene-arm (generic compound 27; FIG. 15). Thus, in a palladium-catalyzed amination, the chlorofluorene nitrile (compound 31 of FIG. 16) was converted to the 2-isopropylanilino fluorene nitrile (compound 32), m.p. 111.3-113° C., in 97% yield. A copper catalyzed N-arylation of compound 32 with 2-isopropyl-iodobenzene gave the N-arylated nitrile (compound 27a; FIG. 16), m.p. 179.2-180.4° C., in 68% yield. Cyclotrimerization of compound 27a in trifluoromethane sulfonic acid and chloroform at room temperature converted it to the triazine chromophore (compound 13A-1 or AF452-2,2'-6iPr), m.p. 281.2-283.7° C., in 87% yield.

Figure 17:
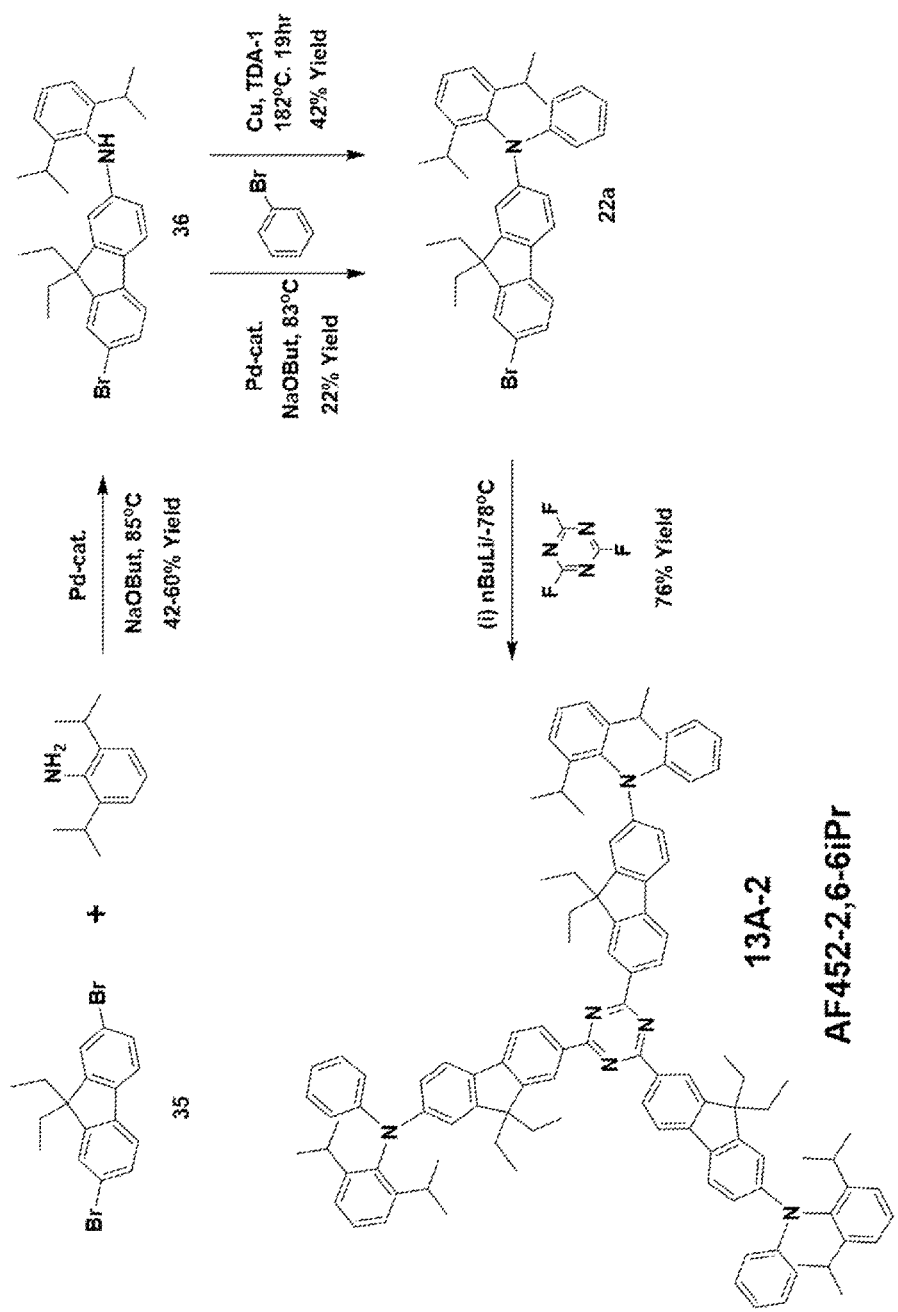
FIG. 17 is a schematic showing a representative method that features the use of triple aromatic nucleophilic displacement reactions for synthesizing an octupolar TPA compound with a sterically-hindered amino as the terminal groups and 1,3,5-triazine hub (13A-2)

With reference to FIG. 17, the preparative details of compound 13A-2 ($R^1=R^3$=isopropyl, $R^2=R^4=R^5=R^6=R^7=R^8=R^9=R^{10}$=H) is provided as Examples-36-38 (see below). In this specific example (13A-2=AF452-2,6-6iPr), an alternative route was used to synthesize the bromo-triarylamino-fluorene precursor (generic compound 22; FIG. 15). Thus, dibromodiethyl fluorene (compound 35) was monoaminated with 2,6-diisopropylaniline to get the aniline-bromofluorene (compound 36), m.p. 158.3-160.3° C., in 42% yield. Compound 36 was allowed to react with bromobenzene in another palladium-catalyzed amination reaction to get the diarylamino-7-bromo-fluorene (compound 22a), m.p. 156-157° C., in 22% yield. Alternatively, a copper-catalyzed reaction on compound 36 using more reactive iodobenzene gave an improved yield, 42%, of compound 22a. Finally, compound 22a was then subjected to a halogen-metal exchange reaction with butyllithium at low temperature, followed by triple aromatic nucleophilic displacement reaction with 2,4,6-trifluoro-1,3,5-triazine to produce the target triazine (compound 13A-2 or AF452-2, 6-6iPr), m.p. 290-292° C., in 76% yield.

Figure 18:
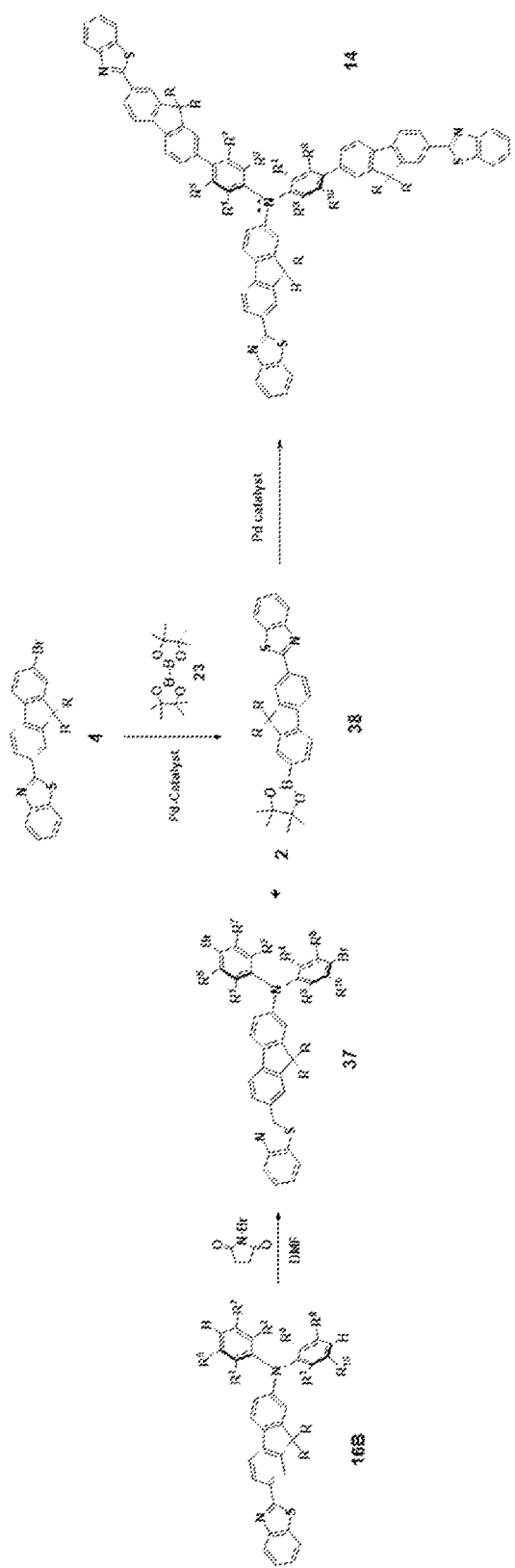
FIG. 18 is a schematic showing a general method for synthesizing TPA compounds with a sterically-hindered amino moiety as the central hub of an octupolar structure 14.

With reference to FIG. 18, the synthesis of the octupolar molecule 14, in which the sterically-hindered triarylamino group serves as the central hub and the benzothiazole groups are the terminal groups, is briefly described as follows. Compound 16B, which can be prepared in a manner similar to that of compound 8B (see FIG. 3), is synthesized, and with all the ortho positions blocked, the electrophilic bromination of the para-positions that is strongly activated by the amine would result in the dibromo compound 38. Subsequently, a double Suzuki coupling reaction with the boronate-functionalized benzothiazolyl-fluorene-arm would result in the desired octupolar molecule 14.

Figure 19:
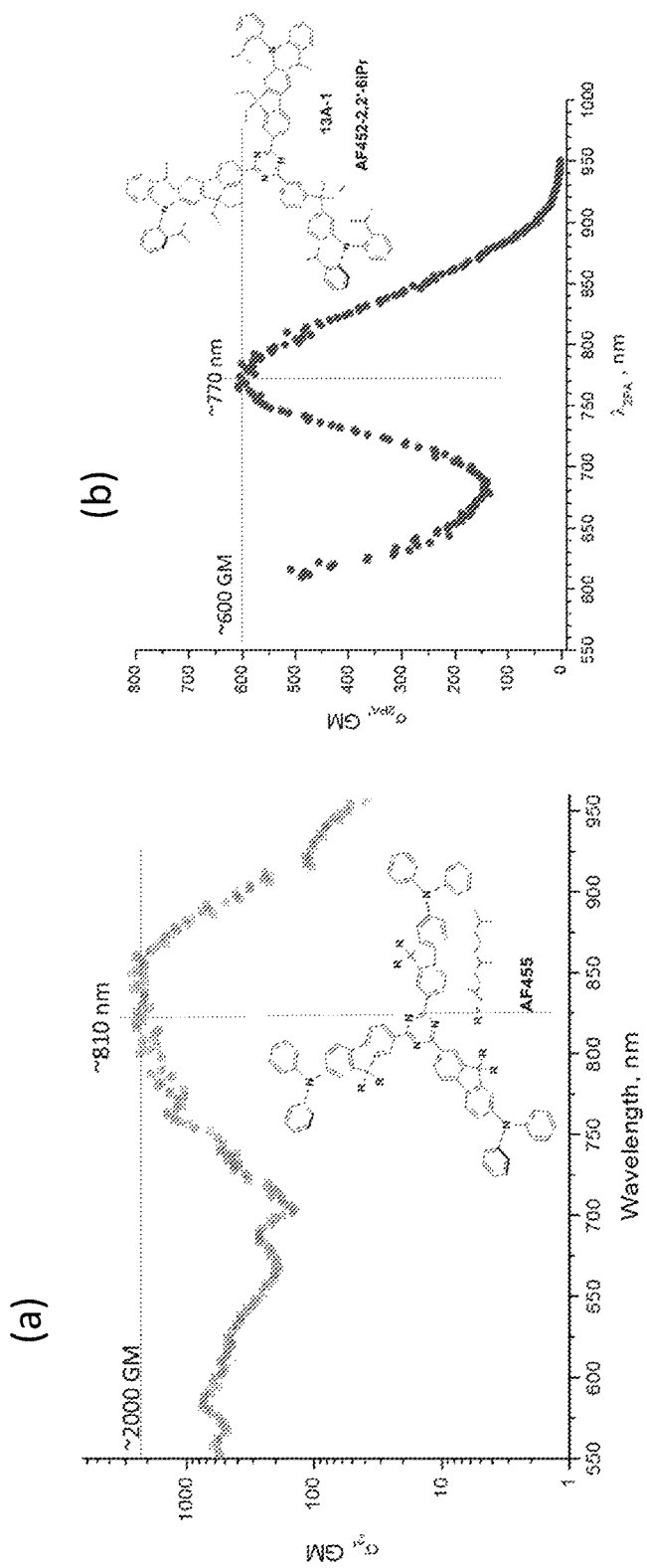
FIG. 19 depicts the plots of molecular two-photon cross-section (in units of Goeppert-Mayer (GM) versus wavelength (nm) of two 1,3,5-triazine-based, octupolar TPA compounds: (a) AF455 and (b) Compound 13A-1 and blue-shifting of 2PA peak of Compound 13A-1 relative to that of AF455.

With reference to FIG. 19, the plots (a) and (b) of molecular two-photon cross-section (in units of Goeppert-Mayer (GM) versus excitation wavelength (nm) of two 1,3,5-triazine-based, octupolar TPA compounds, namely AF455 (2,000 GM at 810 nm) (plot (a)) and Compound 13A-1 (~600 GM at 770 nm) (plot (b)) indicate the higher much two-photon sensitivity than that of dipolar AF240 (560 GM) (see Table 1 below) and AF240 derivatives (140-270 GM) with sterically-hindered diphenylamino end-groups, respectively. In addition, comparison of the 2PA spectrum of Compound 13A-1, FIG. 19(*a*), with sterically hindered diarylamino end-groups with that of AF455 without such steric effect, FIG. 19(*b*), blue-shifting (~40 nm) of 2PA peak of Compound 13A-1 relative to that of AF455 is noted. Because compound 13A-2 is structurally isomeric, its TPA spectrum is similar to that of compound 13-1.

The following examples and methods are presented as illustrative of the present invention or methods of carrying out the invention, and are not restrictive or limiting of the scope of the invention in any manner.

EXAMPLES

Example 1: 2,7-Dibromofluorene

To a mechanically-stirred mixture of fluorene (113.76 g., 0.68 mol), iodine (catalytic amount: 1.96 g, 0.0077 mol), and methylene chloride (750 mL), bromine (74 mL, 1.44 mol) diluted with methylene chloride (100 mL) was added dropwise at room temperature over a period of 1.5 hours. After 5 minutes, a solution of sodium bisulfite (15.0 g) in water (100 mL) was added and the mixture was stirred for 30 minutes, when the mixture became colorless. Water (750 mL) was then added, and methylene chloride was distilled off. The product slurry was filtered and the product was air-dried, 220.5 g., m.p. 151° C. (sh), 156-160° C. This material was used in the next step without further purification.

Example 2: 9,9-Diethyl-2,7-dibromofluorene

To a mechanically stirred mixture of 2,7-dibromofluorene (66.5 g., 0.205 mol.), powdered potassium hydroxide (56.0 g., 1.0 mol.), potassium iodide (3.4 g.) and DMSO (150 ml), cooled to 10° C., ethyl bromide (40 ml, 58.4 g. 0.536 mol.) was added dropwise over 45 minutes. The mixture turned from red to light purple. After allowing the temperature to warm to 20° C., the mixture was left overnight to stir and poured into water, 77.0 g. (98.7% yield), m.p. 144-153° C. The product was then recrystallized from hexane (550 ml) with charcoal treatment, and collected in two crops, m.p. 154-157° C. and 153-154° C., totaling 60.36 g. (77.4% yield).

Example 3: 9,9-Diethyl-7-bromo-fluorene-2-carboxaldehyde

To a mechanically stirred solution of 9,9-diethyl-2,7-dibromofluorene (59.38 g., 0.1563 mol.), in THF (325 ml), cooled in dry ice-ethanol bath, n-butyl lithium (104 ml of 1.6M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 of concentrated hydrochloric acid diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane-ethyl acetate (9:1), to get colorless solids, 40.29 g. (78.4% yield) m.p. 126-128° C. The mother liquor after chromatography over 150 g. silica gel, elution with 1:1 heptane-toluene, and trituration of residual solids in hexanes gave additional product, 6.56 g. (12.8% yield, total 91% yield), m.p. 126-128° C. Mass Spectrum (m/z): 328, 330, (M+). A sample for analysis was prepared by recrystallization from hexanes, m.p. 127-129° C. Anal. Calcd. for $C_{18}H_{17}BrO$, C, 65.55, H, 5.20, and Br, 24.27%. Found, C, 65.60, H, 5.51, and Br, 24.71%.

Example 4:
2-(7-Bromo-9,9-diethylfluoren-2-yl)benzothiazole

A mixture of 9,9-diethyl-7-bromo-fluorene-2-carboxaldehyde (49.35 g., 0.15 mol.), 2-aminothiophenol (20 ml. 0.187 mol., 1.25 eq.), and DMSO (110 ml) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the product benzothiazole, 45.69 g., m.p. 133.6-135° C. An additional 6.6 g., m.p. 134.6-135.5° C., was obtained by chromatography of the ethanol filtrate. Total recovery was 52.29 g. (80.3% yield). Mass Spec: m/z 433, 435, (M+). Anal. Calcd for $C_{24}H_{20}BrNS$: C, 66.37; H, 4.64; Br, 18.40; N, 3.23; S, 7.37%. Found: C, 66.46; H, 4.52; Br, 18.54; N, 3.14; S 7.19%.

Example 5:
2-(7-Amino-9,9-diethylfluoren-2-yl)benzothiazole

Method A:
A solution of 2-(7-bromo-9,9-diethylfluoren-2-yl)benzothiazole (Example 4) (8.68 g, 20 m·mol) in toluene (75 mL) was azeotroped dry and cooled. Bis(dibenzylidene acetone) palladium (0) (290 mg, 0.504 m·mol), tri-t-butylphosphonium tetrafluoroborate (155.3 mg, 0.535 m·mol), and lithium bis(trimethylsilyl)amide (1M solution in toluene, 26 mL, 26 m·mol) were then added, and the mixture was held at 60-62° C. for 5 hours. After cooling, a solution of hydrochloric acid (10 mL) in water (15 mL) was added, and the slurry was filtered. The solids (12.75 g) were stirred with dilute sodium hydroxide, and filtered. The product was then recrystallised from a mixture of toluene and heptane, 6.09 g (82%), m.p. 202.5-203.5° C. Mass spec: m/z 370 (M+). A small sample of the product was dissolved in toluene, passed through a column of alumina and then crystallized from a mixture of toluene and isopropanol (2:1), m.p. 204-205° C. Anal.: Calc. for $C_{24}H_{22}N_2S$: C, 77.80; H, 5.98; N, 7.56; S, 8.65%. Found: C, 77.55; H, 5.98; N, 7.50; S, 8.57%. $^1H$ NMR (CDCl$_3$) δ ppm: 0.36 (t, 6H, 7.36 Hz), 1.99 (m, 2H), 2.13 (m, 2H), 3.84 (s, 2H), 6.68 (m, 2H), 7.36 (td, 1H, 8.12, 1.12 Hz), 7.50 (m, 2H), 7.62 (d, 1H, 7.84 Hz), 7.89 (d, 1H, 7.96 Hz), 7.97 (dd, 1H, 1.64 Hz, 7.92 Hz), 8.07 (m 2H). $^{13}C$ NMR δ ppm: 8.54, 32.92, 56.21 (3 sp$^3$C), 109.55, 114.16, 118.56, 121.28, 121.50, 122.83, 124.82, 126.20, 127.23, 130.59, 131.72, 134.88, 145.34, 147.00, 149.78, 152.80, 154.27, and 169.14 (18 sp$^2$C).

Method B:
Under nitrogen, from a solution of 2-(7-bromo-9,9-diethylfluoren-2-yl) benzothiazole (43.9 g, 0.1 mole) in N, N-dimethylacetamide (150 mL) and toluene (55 mL), all the toluene was distilled off to a solution temperature of 160° C. After cooling the dried mixture to room temperature, Copper (I) iodide (42.85 g, 0.225 mole) and potassium phthalimide (22.44 g, 0.12 mole) were added and the mixture was maintained at 160-165° C. for 20 hours, and then poured into water (1.5 L). The separated solids were collected, washed with water and allowed to dry in air. The air-dried solids (95.65 g) were continuously extracted with methylene chloride in a soxhlet extractor over 4 days. On removal of methylene chloride from the extract, the crude phthalimide product was obtained as a solid (41.62 g). Mass spec: m/z 500 (M+). This was dissolved in tetrahydrofuran (250 mL), and treated with hydrazine hydrate (15.0 mL). After stirring overnight at room temperature, the mixture was filtered, and the solid was washed with toluene. The filtrate and washings were concentrated, and the residual solid product was crystallized from a mixture of toluene and heptane to get the desired aminofluorenyl benzothiazole as an orange solid, 29.34 g (79% yield), m.p. 205.6-206.5° C. Mass spec: m/z 370 (M+). Anal. Calc. for $C_{24}H_{22}N_2S$: C, 77.80; H, 5.98; N, 7.56; S, 8.65%. Found: C, 77.81; H, 6.14; N, 7.73; S, 8.31%.

Example 6: (7-[(Benzothiazol-2-yl)-9,9-diethylfluoren-2-yl]-bis(2-methylphenyl)amine (AF-331-11)

A mixture of 2-(7-amino-9,9-diethylfluoren-2-yl)benzothiazole (Example 5) (1.85 g, 5.0 mmol), 2-bromotoluene (4.12 g, 24.6 mmol), and toluene (55 mL) was azeotroped dry under nitrogen and cooled. Bis(dibenzylideneacetone) palladium(0) (163.2 mg, 0.284 mmol), 2-(di-t-butylphosphino)biphenyl (162.9 mg, 0.546 mmol), and sodium t-butoxide (2.05 g, 21.3 mmol) were added, and the mixture was maintained at 90° C. for 6 hours. After cooling, the mixture was diluted with toluene and water, and the toluene phase was washed with water, dried and concentrated. The residue was chromatographed over silica gel, and the column was eluted with 3:1 toluene-heptane to get the product. The product was then crystallized from a mixture of toluene and heptane, 2.42 g (88% yield), m.p. 203-204° C. Mass spec: m/z 550 (M+). Anal. Calcd. for $C_{38}H_{34}N_2S$: C, 82.87; H, 6.22; N, 5.09; S, 5.82%. Found: C, 82.71; H, 6.37; N, 5.17; S, 5.82%. $^1H$ NMR (CDCl$_3$) δ ppm: 0.34 (t, 6H, 7.32 Hz), 1.84-1.91 (m, 2H), 2.04 (s, 6H), 2.00-2.09 (m, 2H), 6.64-6.69 (m, 2H), 6.99-7.01 (m, 2H), 7.08-7.25 (m, 6H), 7.34-7.38 (m, 1H), 7.45-7.49 (m, 1H), 7.53 (d, 1H, 8.24 Hz), 7.64 (d, 1H, 7.92 Hz), 7.89 (d, 1H, 7.48 Hz), 7.99 (dd, 1H, 1.64 Hz, 7.92 Hz), 8.04-8.07 (m, 2H). $^{13}C$ NMR δ ppm: 8.49, 18.94, 32.70, 56.28 (4 sp$^3$C), 114.28, 118.93, 119.43, 120.83, 121.33, 121.50, 122.86, 124.83, 126.21, 126.99, 127.22, 127.43, 130.95, 131.73, 133.22, 134.52, 134.90, 144.97, 146.10, 149.22, 150.30, 152.10, 154.27, 169.01 (24 sp$^2$C).

Example 7: N,7-[(benzothiazol-2-yl)-9,9-diethylfluoren-2-yl]-N-(2,6-dimethylphenyl)amine A mixture of 2-(7-bromo-9,9-diethylfluoren-2-yl)benzothiazole (Example 4) (21.70 g, 0.05 mol), 2,6-dimethylaniline (6.54 g, 0.05 mol), and toluene (200 mL) was azeotroped dry under nitrogen and cooled. Palladium(II) acetate (121.0 mg, 0.54 mol), bis(2-diphenylphosphinophenyl) ether (DPEphos, 428.9 mg, 0.796 mmol), and sodium t-butoxide (7.25 g, 0.075 mol), were then added, and the mixture was held at 90° C. for 6 hours. The solids separated on cooling were collected, and the filtrate was diluted with toluene, washed with water, dried and concentrated, to get additional solids. Both solids were combined, and crystallized from a mixture of toluene and heptane to get the product, 20.94 g, m.p. 191-194° C. Additional product, 1.82 g, m.p. 195-197° C., was obtained from a column chromatography of the crystallization liquors, followed by crystallization. Total product recovery was 22.76 g (96% yield). Mass spec: m/z 474 (M+). Anal. Calcd. for $C_{32}H_{30}N_2S$: C, 80.97; H, 6.37; N, 5.90; S, 6.76%. Found: C, 80.66; H, 6.49; N, 6.26; S, 6.74%. $^1$H NMR (CDCl$_3$) δ ppm: 0.35 (t, 6H, 7.34 Hz), 1.89-1.97 (m, 2H), 2.05-2.12 (m, 2H), 2.24 (s, 6H), 5.38 (broad s, 1H), 6.45 (broad s, 1H), 6.52 (d, 1H, 7.56 Hz), 7.10-7.17 (m, 3H), 7.36 (t, 1H, 8.10 Hz), 7.47 (t, 1H, 8.28 Hz), 7.53 (d, 1H, 8.16 Hz), 7.61 (d, 1H, 7.88 Hz), 7.89 (d, 1H, 7.64 Hz), 7.96 (dd, 1H, 1.52, 7.88 Hz), 8.03-8.08 (m, 2H). $^{13}$C NMR: 8.53, 18.45, 32.85, 56.20 (4 sp$^3$C), 107.76, 112.87, 118.40, 121.22, 121.28, 121.49, 122.81, 124.78, 125.85, 126.18, 127.24, 128.66, 130.41, 131.36, 134.88, 135.76, 138.02, 145.47, 146.93, 149.81, 152.76, 154.29, and 168.18 (23 sp$^2$C).

Example 8: N,7-[(benzothiazol-2-yl)-9,9-diethylfluoren-2-yl]-N-phenyl-N-(2,6-dimethylphenyl) amine (AF331-20)

To a dried mixture of N,7-[(benzothiazol-2-yl)-9,9-diethylfluorenyl-2-yl]-N-(2,6-dimethylphenyl)amine (Example 7; 2.37 g, 5.0 mmol), bromobenzene (2.18 g, 13.9 mmol) and toluene (50 mL), bis(dibenzylideneacetone)palladium (0) (66.9 mg, 0.116 mmol), 2-di t-butylphosphino biphenyl (72.9 mg, 0.244 mmol) and sodium t-butoxide (1.2 g, 12.5 mmol) were added, and the mixture was held at 95° C. for 3 hours. After cooling and dilution with toluene, the toluene solution was washed with water, dried and concentrated. The residue was chromatographed over silica gel and the column was eluted with toluene to get the product. The product was recrystallized from a mixture of toluene and isopropanol, 2.68 g (97% yield), m.p. 225.7-227.0° C. Mass spec: m/z 550 (M+). Anal. Calcd. for $C_{38}H_{34}N_2S$: C, 82.87; H, 6.22; N, 5.09; S, 5.82%. Found: C, 82.91; H, 6.31; N, 5.35; S, 5.89%. $^1$H NMR (CDCl$_3$) δ ppm: 0.37 (t, 6H, 7.32 Hz), 1.90-1.97 (m, 2H), 2.05 (s, 6H), 2.04-2.11 (m, 2H), 6.81 (dd, 1H, 2.12, 8.28 Hz), 6.92 (t, 1H, 7.28 Hz), 7.02 (d, 2H, 8.64 Hz), 7.11-7.25 (m, 6H), 7.36 (t, 1H, 8.08 Hz), 7.48 (t, 1H, 7.16 Hz), 7.54 (d, 1H, 8.28 Hz), 7.65 (d, 1H, 7.96 Hz), 7.89 (d, 1H, 7.92 Hz), 7.99 (dd, 1H, 1.64, 7.96 Hz), 8.07 (d, 2H, 8.08 Hz). $^{13}$C NMR: 8.54, 18.70, 32.69, 56.30 (4 sp$^3$C), 114.16, 118.85, 118.99, 119.90, 121.06, 121.08, 121.37, 121.51, 122.88, 124.88, 126.23, 127.22, 127.26, 129.04, 129.19, 129.32, 131.07, 133.70, 134.91, 137.81, 142.75, 144.80, 145.99, 146.53, 150.54, 152.01, 154.27, and 168.96 (28 sp$^2$C).

Example 9: N,7-[(Benzothiazol-2-yl)-9,9-diethylfluoren-2-yl]-N-(2-methylphenyl)-2,6-dimethylphenyl-amine (AF-331-21)

2-Bromotoluene (1.84 g, 10.8 mmol) was similarly reacted with N,7-[(benzothiazol-2-yl)-9,9-diethylfluoren-2-yl]-N-(2,6-dimethylphenyl)amine (Example 7; 2.37 g, 5.0 mmol), bis(dibenzylideneacetone)palladium (0) (66.6 mg, 0.116 mmol), 2-di t-butylphosphinobiphenyl (74.9 mg, 0.25 mmol), and sodium t-butoxide (1.12 g, 11.65 mmol) in toluene (50 mL) for 44 hours at 98-100° C. The product was separated from unreacted starting material by chromatography on silica gel and elution with 65% toluene-35% heptane, and recrystallization from a mixture of toluene and isopropanol, 1.91 g (68% yield), m.p. 232-234° C. Mass spec: m/z 564 (M+). Anal. Calcd. for $C_{39}H_{36}N_2S$: C, 82.94; H, 6.42; N, 4.96; S, 5.68%. Found: C, 82.85; H, 6.42; N, 5.35; S, 5.64%. $^1$H NMR (CDCl$_3$) δ ppm: 0.27 (t, 3H, 7.32 Hz), 0.38 (t, 3H, 7.32 Hz), 1.83-1.92 (m, 2H), 2.02 (s, 6H), 2.03-2.08 (m, 2H), 2.11 (s, 3H), 6.56 (d, 2H, 8.0 Hz), 6.79 (dd, 1H, 1.28, 7.88 Hz), 7.02-7.16 (m, 5H), 7.23 (dd, 1H, 1.20, 7.32 Hz), 7.36 (t, 1H, 8.04 Hz), 7.46-7.52 (m, 2H), 7.63 (d, 1H, 7.92 Hz), 7.89 (d, 1H, 7.64 Hz), 7.97 (dd, 1H, 1.64, 7.92 Hz), 8.04-8.07 (m, 2H). $^{13}$C NMR: 8.36, 8.50, 19.36, 18.35, 20.08, 32.66, 32.90, 56.26 (8 sp$^2$C), 112.31, 117.62, 118.78, 121.04, 121.27, 121.50, 122.83, 123.75, 124.83, 126.21, 126.57, 126.91, 127.23, 129.38, 129.54, 130.76, 131.97, 132.50, 132.53, 134.88, 137.26, 137.28, 143.07, 144.49, 145.13, 148.75, 150.12, 152.18, 154.26, and 169.05 (30 sp$^2$C). Elution of the column with toluene returned N,7-[(benzothiazol-2-yl)-9,9-diethylfluoren-2-yl]-2,6-dimethylphenylamine or xylidenofluorenyl benzothiazole (identified by TLC), 0.56 g (24%), m.p. 194-195° C.

Example 10: N,7-[(Benzothiazol-2-yl)-9,9-diethylfluoren-2-yl]-N,N-bis(2,6-dimethylphenyl)amine (AF331-22)

A mixture of N,7-[(benzothiazol-2-yl)-9,9-diethylfluoren-2-yl]-N-(2,6-dimethylphenyl)amine (Example 7; 4.74 g, 10.0 mmol), 2-bromo-1,3-dimethylbenzene (5.55 g, 30.0 mmol), potassium carbonate (6.90 g, 49.9 mmol), copper (I) iodide (4.0 g, 21 mmol), copper powder (1.0 g, 15.7 mg atom), DMAC (80 mL), and toluene (30 mL), was heated to reflux, and the solvents were partially removed by distillation (60 mL). The mixture was kept under reflux, and 2-bromo-1,3-dimethylbenzene (3.0 g, 16.2 mmol) was added after 24 and 48 hours. After a total of 5 days under reflux, the reaction was cooled, and filtered. The filtrate was diluted with toluene, the solution was washed with water, dried and concentrated. The residue was chromatographed over silica gel, and the column was eluted with 3:1 toluene-heptane to get the product after recrystallization from a mixture of toluene and isopropanol, 1.13 g (20% yield), m.p. 236-237° C. Mass spec: m/z 578 (M+). Anal. Calcd. for $C_{40}H_{38}N_2S$: C, 83.00; H, 6.62; N, 4S: C, 83.00; H, 6.62; N, 4.84; S, 5.54%. Found: C, 82.83; H, 6.56; N, 5.18; S, 5.58%. $^1$H NMR (CDCl$_3$) δ ppm: 0.39 (t, 6H, 7.30 Hz), 1.90-1.99 (m, 2H), 2.02-2.10 (m, 2H), 2.05 (s, 6H), 2.21 (s, 6H), 6.58 (s, 1H), 6.65 (s, 2H), 6.74 (dd, 1H, 2.08, 8.24 Hz), 7.12-7.20 (m, 4H), 7.36 (t, 1H, 8.04 Hz), 7.48 (t, 1H, 7.12 Hz), 7.52 (d, 1H, 8.28 Hz), 7.64 (d, 1H, 7.92 Hz), 7.89 (d, 1H, 7.88 Hz), 7.98 (dd, 1H, 1.6 Hz, 7.96 Hz), 8.06-8.08 (m, 2H). $^{13}$C NMR: 8.53, 18.77, 21.46, 32.66, 56.24 (5 sp$^3$C), 114.83, 117.54, 118.96, 119.04, 121.02, 121.33, 121.51, 122.87, 122.93, 124.86, 126.22, 127.06, 127.26, 129.23, 131.01, 133.51, 134.90, 137.83, 138.72, 142.78, 144.84, 146.00, 146.69, 150.52, 151.76, 154.27, and 168.99 (27 sp$^2$C).

Example 11: N,7-[(Benzothiazol-2-yl)-9,9-diethylfluoren-2-yl]-N,N-bis(2-ethylphenyl)amine (AF337-11)

A mixture of 2-(7-amino-9,9-diethylfluoren-2-yl)benzothiazole (34) (Example 5; 1.85 g, 5 mmol), 2-ethyl bromobenzene (2.8 g, 15.12 mmol), and toluene (55 mL) was azeotroped dry and cooled. Bis(dibenzylidene acetaone) palladium (0) (163.4 mg, 0.284 mmol), 2-di-t-butylphosphino biphenyl (161.8 mg, 0.542 mmol), and sodium t-butoxide were then added, and the mixture was held at 95° C. for 20 hours. TLC examination revealed the presence of both mono and diarylated products. Additional 2-ethyl-bromobenzene (0.75 g, 4.05 mmol) was added, and the reaction was allowed to proceed for an additional 4-hour period at 101° C. After cooling and dilution with toluene, the toluene phase was washed with water, dried and concentrated. The residue (4.34 g) was chromatographed over silica gel. Elution of the column with 65% toluene-heptane, gave the product after crystallization from a mixture of isopropanol and toluene, 2.08 g (72%), m.p. 166.5-168° C. Mass spec: m/z 578 (M+). Anal. Calcd. for $C_{40}H_{38}N_2S$: C, 83.00; H, 6.62; N, 4.84; and S, 5.54%. Found: C, 83.10, H, 6.71; N, 4.73; and S, 5.68%. $^1$H NMR (CDCl$_3$) δ ppm: 0.33 (t, 6H, 7.32 Hz), 1.09, (t, 6H, 7.52 Hz), 1.81-1.90 (m, 2H), 2.01-2.10 (m, 2H), 2.46 (q, 4H, 7.56 Hz), 6.62 (d, 1H, 2.0 Hz), 6.68 (dd, 1H, 2.12 Hz), 7.01 (s, 2H), 7.16 (m, 4H), 7.32 (m 2H), 7.36 (m, 1H), 7.48 (m 1H), 7.52 (d, 1H, 8.28 Hz), 7.64 (d, 1H, 7.92 Hz), 7.89 (d, 1H, 7.44 Hz), 7.98 (dd, 1H), 1.6 Hz, 7.92 Hz), 8.06 (m, 2H). $^{13}$C NMR δ ppm: 8.47, 13.89, 24.19, 32.70, 56.29 (5 spa C), 114.18, 118.93, 119.93, 119.59, 120.72, 121.33, 121.51, 122.86, 124.85, 125.18, 126.22, 126.85, 127.21, 128.14, 129.60, 130.92, 133.15, 134.90, 140.25, 144.99, 145.76, 150.28, 150.32, 152.01, 154.27, and 169.02 (25 sp$^2$C). Elution with 75% toluene-heptane gave the mono arylated compound, 0.2 g (9%), m.p. 150-153° C. Mass spec: m/z 474 (M+). $^1$H NMR (CDCl$_3$) δ ppm: 0.37 (t, 6H, 7.2 Hz), 1.28 (t, 3H, 7.6 Hz), 1.99 (m 2H0, 2.13 (m, 2H), 2.67 (q, 2H, 7.46 Hz), 5.60 (s, 1H), 6.93 (m, 2H), 7.04 (t, 1H, 7.4 Hz), 7.19 (t, 1H, 7.56 Hz), 7.30 (t, 2H, 8.08 Hz), 7.37 (t, 1H, 7.72 Hz), 7.49 (t, 1H, 7.68 Hz), 7.61 (d, 1H, 7.8 Hz), 7.67 (d, 1H, 7.92 Hz), 7.90 (d, 1H, 7.92 Hz), 7.99 (d, 1H, 7.88 Hz), 8.08 (m, 2H).

Example 12: N,7-[(benzothiazol-2-yl)-9,9-diethylfluoren-2-yl]-N-(2,6-diethylphenyl)amine A solution of 2-(7-bromo-9,9-diethylfluoren-2-yl)benzothiazole (Example 5; 10.85 g, 25 mmol), and 2,6-diethylaniline (4.88 g, 32.75 mmol) in toluene (125 mL) was azeotroped dry under nitrogen and cooled. Palladium (II) acetate (62.4 mg, 0.278 mmol), DPE Phos (212 mg, 0.394 mmol), and sodium t-butoxide (2.99 g, 31.1 mmol) were added, and the mixture was held at 95° C. for 4 hours. The residue (17.83 g) left after extractive work-up, was chromatographed over silica gel. Elution with 3:1 toluene-heptane gave the product, 11.53 g (89%). A small sample was recrystallized from isopropanol, m.p. 121-123° C. Mass spec: m/z 502 (M+). Anal. Calcd. for $C_{34}H_{34}N_2S$: C, 81.23; H, 6.82; N, 5.57; and S, 6.34%. Found: C, 81.22; H, 6.79; N, 5.57 and S, 6.38%. $^1$H NMR (CDCl$_3$) δ ppm: 0.33 (t, 6H, 7.34 Hz), 1.14 (t, 6H, 7.54 Hz), 1.89 (m, 2H), 2.08 (m, 2H), 2.61 (q, 4H, 7.56 HZ), 5.32 (S, 1H), 6.40 (D, 1H, 2.04 Hz), 6.53 (dd, 1H, 2.12 hz, 8.16 Hz), 7.20 (m, 3H), 7.35 (m, 1H), 7.49 (m, 2H), 7.60 (m, d, 1H, 8.08 Hz), 7.88 (m, 1H), 7.94 (m, 1H), and 8.05 (m, 2H). $^{13}$C NMR δ ppm: 8.47, 14.76, 24.80, 32.84, 56.18 (5 sp$^3$C), 107.35, 112.72, 118.35, 121.21, 121.25, 121.47, 122.80, 124.76, 126.16, 126.75, 126.90, 127.24, 130.35, 131.10, 134.87, 136.69, 142.43, 145.51, 148.17, 149.78, 152.75, 154.30 and 169.18 (23 sp$^2$C).

Example 13: 7-(Benzothiazol-2-yl)-9,9-diethylfluoren-2-yl-phenyl-(2,6-diethyl)-phenylamine (AF337-20)

Mixture of N,7-[(benzothiazol-2-yl)-9,9-diethylfluoren-2-yl]-N-(2,6-diethylphenyl)amine (Example 12; 2.26 g, 5 mmol), bromobenzene (3.0 g, 19.1 mmol) and toluene (50 mL) was azeotroped dry and cooled. Pd(dba)$_2$ (64.1 mg, 0.11 mmol), 2-di t-butylphosphino biphenyl (69.1 mg, 0.24 mmol), and sodium t-butoxide (2.06 g, 21.4 mmol) were added and the mixture was held at 90° C. for 20 hours. Extractive work-up left a residue (7.6 g), and it was chromatographed over silica gel. Elution with 1:1 toluene-heptane followed by crystallization from a mixture of toluene and heptane gave the product (42), 2.47 g (85%), m.p. 170-171.5° C. Mass spec: m/z 578 (M+). Anal. Calcd. for $C_{40}H_{38}N_2S$: C, 83.00, H, 6.62, N, 4.84 and S, 5.54%. Found: C, 83.06; H, 6.58; N, 4.80 and S, 5.60%. $^1$H NMR (CDCl$_3$) δ ppm: 0.37 (t, 6H, 7.32 Hz), 0.97 (t, 6H, 7.56 Hz), 1.91 (m, 2H), 2.07 (m 2H), 2.46 (m, 4H), 6.84 (dd, 1H, 2.08 and 8.32 Hz), 6.92 (t, 1H, 7.28 Hz), 7.03 (d, 1H, 7.8 Hz), 7.12 (d, 1H, 1.96 Hz), 7.22 (m, 4H), 7.34 (m, 2H), 7.48 (t, 1H, 8.2 Hz), 7.53 (d, 1H, 8.28 Hz), 7.64 (d, 1H, 7.92 Hz), 7.89 (d, 1H, 7.84 Hz), 7.98 (dd, 2H, 1.52 and 7.92 Hz), 8.06 (m, 2H). $^{13}$C NMR δ ppm: 8.49, 13.92, 24.48, 32.69, 56.30 (5 sp$^3$C), 114.24, 119.00, 119.13, 120.14, 120.92, 121.04, 121.41, 121.51, 122.91, 124.87, 126.23, 127.25, 127.50, 127.74, 129.07, 131.09, 133.62, 134.94, 141.69, 143.46, 144.82, 146.68, 147.27, 150.46, 151.95, 154.31, and 168.96 (27 sp$^2$C).

Example 14: 2-Ethyl-iodobenzene

With mechanical stirring, a suspension of 2-ethylaniline (36.4 g, 0.30 mol) in 25 wt % sulfuric acid (240 mL), was cooled in 1, 2-xylene-dry ice bath to −20° C. Sodium nitrite (21 g, 0.30 mol) in water (40 mL) was added, and after 1 hour at this temperature, the gelly mass was transferred to a solution of potassium iodide (150 g, 0.90 mol) in water (150 mL), and the mixture was left stirring at room temperature for 18 hours. The reaction mass was extracted into hexanes and the extract after drying was passed through a column of silica gel to get the product as a colorless oil after evaporation of the solvent, 59.14 g (85%). Mass spec: m/z 232 (M+). Anal. Calcd. for $C_8H_9I$: C, 41.41; H, 3.91 and I, 54.32%. Found: C, 41.50; H, 3.90 and I, 54.28%. $^1$H NMR (CDCl$_3$) δ ppm: 1.20 (t, 3H, 7.52 Hz), 2.73 (q, 2H, 7.52 Hz), 6.86 (td, 1H, 7.50 and 1.76 Hz), 7.25 (m, 2H), 7.80 (dd, 1H, 0.88 and 7.88 Hz).

Example 15: N,7-[(Benzothiazol-2-yl)-9,9-diethylfluoren-2-yl)-N-(2,6-diethylphenyl)-N-(2-ethylphenyl)amine (AF337-21)

A mixture of 2-ethyl iodobenzene (6.09 g, 25.9 mmol), N,7-[(benzothiazol-2-yl)-9,9-diethylfluoren-2-yl]-N-(2,6-diethylphenyl)amine (Example 12; (2 g, 3.98 mmol), copper powder (0.39 g, 6.14 mmol), 18-crown-6 (0.105 g, 0.397 mmol) and potassium carbonate (2.4 g, 17.4 mmol) was kept in a heating bath at 240-270° C. under nitrogen for 18 hours, cooled, diluted with toluene and filtered. The toluene solution was washed with water, dried and concentrated. The residue (9.29 g) was chromatographed over silica gel and eluted with 3:1 and 1:1 heptane-toluene. Earlier fractions contained iodoethyl benzene contaminated with self-coupled products. The product was obtained from later fractions, after crystallization from a mixture of isopropanol and toluene, 1.86 g (77%), m.p. 201-203° C. Mass spec: m/z 606 (M⁺). Anal. Calcd. for $C_{42}H_{42}N_2S$: C, 83.12; H, 6.98; N, 4.62 and S, 5.28%. Found: C, 82.95; H, 7.09; N, 4.35 and S, 5.18%. ¹H NMR (CDCl₃) δ ppm: 0.26 (t, 3H, 7.30 Hz), 0.37 (t, 3H, 7.30 Hz), 0.92 (t, 3H, 7.50 Hz), 1.00 (t, 3H, 7.54 Hz), 1.17 (t, 3H, 7.52 hz), 1.87 (m, 2H), 2.06 (m, 2H), 2.43 (m, 6H), 6.54 (m 2H), 6.79 (d, 1H, 7.36 Hz), 7.09 (m, 2H), 7.18 (m, 2H), 7.26 (m, 1H), 7.36 (m, 2H), 7.47 (m, 2H), 7.62 (d, 1H, 8.0 Hz), 7.89 (d, 1H, 8.0 Hz), 7.97 (dd, 1H, 1.52, 7.92 Hz), 8.05 (m, 2H). ¹³C NMR δ 8.28, 8.47, 13.44, 14.00, 14.27, 24.22, 24.73, 24.86, 32.64, 32.93, 56.31 (11 sp³C), 118.78, 120.84, 121.33, 121.49, 122.87, 124.03, 124.83, 125.22, 126.20, 126.64, 127.22, 127.33, 127.60, 128.23, 129.06, 130.79, 132.45, 132.93, 138.11, 143.09, 143.22, 143.40, 143.66, 145.16, 150.10, 150.42, 152.07, 154.32 and 169.06 (29 sp²C).

Example 16: 2,6-Diethyl-iodobenzene

Diethyl aniline (29.85 g, 0.2 mol) was diazotized in 25% sulfuric acid (160 mL) with sodium nitrite (14 g, 0.2 mole) at −20° C., and treated with potassium iodide (100 g, 0.6 mole) in water (100 mL). An extractive work-up using hexanes followed by silica gel chromatography gave diethyl iodo benzene, 32.01 g (62%). Mass spec: m/z 260 (M+). ¹H NMR (CDCl₃) δ ppm: 1.21 (t, 6H), 2.81 9q 4H), 7.04 (d, 2H), and 7.19 (t, 1H).

Example 17

N,7-[(Benzothiazol-2-yl)-9,9-diethylfluoren-2-yl]-N, N-bis(2,6-diethylphenyl)amine (AF337-22)

A mixture of 2,6,-diethyl-iodobenzene (15.6 mmol), N,7-[(benzothiazol-2-yl)-9,9-diethylfluoren-2-yl]-N-(2,6-diethylphenyl)amine (Example 12; (5.02 g, 10 mmol), 18-crown-6 (0.15 g, 0.567 mmol), copper powder (1.1 g, 17.3 mmol), and potassium carbonate (5.63 g, 40.8 mmol) was kept under nitrogen in a bath at 200-220° C. for 20 hours. TLC examination revealed partial conversion, and the presence of many products. Extractive work-up left a residue (16.85 g), which was chromatographed over silica gel. Elution with 5:3 heptane-toluene gave a product containing fraction (1.48 g). This was rechromatographed over silica gel, and the product was recrystallized from heptane, 0.26 g (4%), m.p. 227.3-229.1° C. Mass spec: m/z 634 (M⁺). Anal. Calcd. for $C_{44}H_{46}N_2S$: C, 83.24; H, 7.30; N, 4.41 and S, 5.05%. Found: C, 83.26; H, 7.26; N, 4.45; and S, 5.06%. ¹H NMR (CDCl₃) δ ppm: 0.33 (t, 3H, 7.28 Hz), 0.40 (t, 3H, 7.28 Hz), 0.76 (t, 3H, 6.04 Hz), 0.82 (t, 3H, 7.48 Hz), 1.05 (t, 3H, 7.52 Hz), 1.13 (t, 3H, 7.48 Hz) 1.90 (m, 2H), 2.08 (m 2H), 2.22 (m, 4H), 2.45 (m, 2H), 2.62 (m, 2H), 6.60 (d, 1H, 2.08 Hz), 6.66 (dd, 1H, 2.16 and 8.24 Hz), 7.08 (m, 2H), 7.22 (m, 4H), 7.39 (m, 1H), 7.52 (m, 2H), 7.68 (d, 1H, 5.64 hz), 7.92 (d, 1H, 7.64 Hz), 8.00 (dd, 1H, 1.64 and 5.36 Hz), 8.03 (m, 2H). ¹³C NMR δ ppm: 8.21, 8.59, 13.28, 13.31, 14.87, 14.93, 24.58, 24.74, 25.48, 32.64, 32.81, 56.29 (12 sp³C), 113.81, 118.85, 119.02, 121.04, 121.34, 121.49, 122.86, 124.84, 125.65, 125.78, 126.21, 127.02, 127.19, 127.36, 128.04, 128.30, 130.78, 132.50, 134.91, 140.96, 141.39, 141.41, 141.62, 142.96, 143.75, 145.11, 150.14, 152.34, 152.95, 154.30, and 169.05 (31 sp²C).

Example 18: N,7-[(benzothiazol-2-yl)-9,9-diethylfluoren-2-yl]-2-isopropylphenylamine A mixture of 2-(7-bromo-9,9-diethylfluoren-2-yl)benzothiazole (Example 4 10.85 g, 25 mmol), 2-isopropyl aniline (4.16 g, 30.8 mmol) and toluene (100 mL) was azeotroped dry under nitrogen and cooled. Bis(dibenzylidene acetone) palladium(0) (295.5 mg, 0.514 mmol), 1,1-bis(diphenylphosphino)ferrocene (292.4 mg, 0.528 mmol) and sodium t-butoxide (3.48 g, 36.2 mmol) were then added, and the mixture was held at 92° C. for 4 hours. After cooling and dilution with toluene, the toluene solution was washed with water, dried, and concentrated. The residue (39 g) was chromatographed over silica gel, and the column was eluted with 65% toluene-heptane to get the product, 11.44 g (93%), m.p. 193-195° C. Mass spec: m/z 488 (M⁺). Anal. Calcd. for $C_{33}H_{32}N_2S$: C, 81.10, H, 6.60, N, 5.72 and S, 6.56%. Found: C, 81.19; H, 6.61; N, 5.72 and S, 6.55%. ¹H NMR (CDCl₃): δ ppm: 0.38 (t, 6H, 7.32 Hz), 1.27 (d, 6H, 6.84 Hz), 1.98 (m, 2H), 2.12 (m, 2H), 3.20 (septet, 1H, 6.82 Hz), 5.60 (s, 1H), 6.86 (m, 2H), 7.11 (td, 1H, 1.28, 7.56 Hz), 7.18 (t, 1H, 1.6 and 7.4 Hz), 7.33 (m, 3H), 7.48 (t, 1H, 8.24 Hz), 7.59 (d, 1H, 8.12 Hz), 7.65 (d, 1H, 7.92 Hz), 7.89 (d, 1H, 7.84 Hz), 7.99 (d, 1H, 1.56, 7.88 Hz), 8.07 (m, 2H). ¹³C NMR δ ppm: 8.58, 23.08, 27.69, 32.82, 56.33 (5 sp³C), 110.68, 115.64, 118.73, 121.17, 121.33, 121.50, 121.97, 122.85, 123.72, 124.84, 126.21, 125.55, 127.26, 130.79, 132.76, 134.89, 139.41, 140.86, 145.12, 145.77, 150.04, 152.64, 154.28 and 169.06 (24 sp²C).

Example 19: N,7-[(benzothiazol-2-yl)-9,9-diethylfluoren-2-yl]-N,N-bis(2-isopropylpheny)lamine (AF388-11)

A mixture of N,7-[(benzothiazol-2-yl)-9,9-diethylfluoren-2-yl]-2-isopropylphenylamine (Example 17; 2.62 g, 5.32 mmol), 2-isopropyl bromobenzene (1.99 g, 10 mmol) and toluene (50 mL) was azeotroped dry under nitrogen and cooled. Bis-dibenzylidene acetone palladium (0) (69.2 mg, 0.12 mmol), 2-di-t-butylphosphino biphenyl (70.4 mg, 0.24 mmol), and sodium t-butoxide (1.34 g, 13.9 mmol) were then added, and the mixture was held at 94° C. for 24 hours, and at 100° C. for 44 hours. Extractive work-up left a residue (5.31 g), which was chromatographed over silica gel. Elution with 1:1 toluene-heptane gave the product, which was crystallized from toluene and isopropanol, 2.01 g (62%), m.p. 206-208° C. Mass spec: m/z 606 (M⁺). Anal. Calcd. for $C_{42}H_{42}N_2S$: C, 83.12, H, 6.98, N, 4.62 and S, 5.28%. Found: C, 83.11, H, 6.94, N, 4.61 and S, 5.30%. ¹H NMR (CDCl₃) δ ppm: 0.31 (t, 6H, 7.30 Hz), 1.03 (d, 12H, 6.68 Hz), 1.87 (m, 2H), 2.17 (m, 2H), 3.29 (m, 2H), 6.69 (m, 2H), 6.97 (d, 2H, 7.76 Hz), 7.12 (td, 2H, 1.6, 7.84 Hz), 7.19 (td, 2H, 1.24, 7.44 Hz), 7.35, (m, 3H), 7.49 (m, 2H), 7.64 (d, 1H, 7.92 Hz), 7.89 (d, 1H, 8.0 Hz), 7.98 (dd, 1H, 1.6, 7.88 Hz), 8.06 (m, 2H). ¹³C NMR δ ppm: 8.50, 23.48, 27.43, 32.68, 56.41 (5 sp³C), 115.00, 118.99, 120.61, 121.33, 121.50, 122.87, 124.86, 125.59, 126.22, 126.65, 127.18, 127.53, 128.32, 130.97, 133.44, 134.90, 144.96, 145.34, 150.22, 151.83, 151.91, 154.27 and 169.00 (23 sp²C). Toluene-heptane 3:1 returned some starting amino benzothiazole (Example 17), 0.65 g, m.p. 188-191° C.

Example 20: N,7-[(Benzothiazol-2-yl)-9,9-diethylfluoren-2-yl)-N-(2,6-diisopropylphenyl)amine 2-(7-bromo-9,9-diethylfluoren-2-yl)benzothiazole (Example 4; 11.65 g, 26.84 mmol) was aminated with 2,6-diisopropyl aniline (5.24 g, 29.6 mmol) using palladium (II)acetate (64.9 mg, 0.29 mmol), DPE Phos (231.5 mg, 0.43 mmol) and sodium t-butoxide (3.35 g, 34.8 mmol) in toluene (100 mL0 at 99° C. for 5 hours. Extractive work up followed by chromatography on silica gel, gave the product in 65% toluene-heptane eluates, 12.66 g (89%), m.p. 189-191° C. (isopropanol). Mass spec: m/z 530 (M⁺). Anal. Calcd. for $C_{36}H_{38}N_2S$: C, 81.46; H, 7.22, N, 5.28 and S, 6.04%. Found: C, 81.25, H, 7.32, N, 5.21 and S, 6.07%.

Example 21: N,7-[(benzothiazol-2-yl)-9,9-diethyl-fluoren-2-yl]-N-(2,6-diisopropylphenyl)-phenylamine (AF338-20)

A mixture of N,7-[(benzothiazol-2-yl)-9,9-diethylfluoren-2-yl)-N-(2,6-diisopropylphenyl)amine (Example 19; 2.65 g, 5 mmol), bromobenzene (2.35 g, 15 mmol), and toluene (50 mL) was azeotroped dry under nitrogen and cooled. Bis (dibenzylidene acetone)palladium (0) (59.2 mg, 0.103 mmol), 2-di-t-butylphosphino biphenyl (63 mg, 0.21 mmol) and sodium t-butoxide (1.35 g, 14 mmol) were then added, and the mixture was held at 92° C. for 20 hour. Second portions of bromobenzene (2.66 g, 16.94 mmol) and sodium t-butoxide (1.45 g, 15.1 mmol) were added and the reaction was kept at 100° C. for 24 hours. After cooling and extractive work-up, the residue (7.75 g) left after evaporation of the solvents was chromatrographed over silica gel. The product was eluted out with 65% toluene-heptane, and was crystallized from a mixture of isopropanol and toluene, 1.57 g (52%), m.p. 217-218.5° C. Mass spec: m/z 606 (M⁺). Anal. Calcd. for $C_{42}H_{42}N_2S$: C, 83.12; H, 6.98; N, 4.62 and S 5.28%. Found: C, 83.11, H, 6.97; N, 4.62 and S, 5.31%. ¹H NMR (CDCl₃) δ ppm: 0.36 (t, 6H, 7.30 Hz), 0.95 (2 overlapping doublets, 12H, 6.94 Hz), 1.92 (m 2H), 2.07 (m, 2H), 3.20 (quintet, 2H, 6.84 Hz), 6.90 (m, 2H), 7.06 (dd, 2H, 0.88 and 12.56 Hz), 7.13 (d, 1H, 1.96 Hz), 7.23 (m, 4H), 7.38 (m, 2H), 7.46 (td, 1H, 8.08 and 1.0 Hz), 7.54 (m, 1H), 7.64 (d, 1H, 7.92 Hz), 7.89 (d, 1H, 7.48 Hz), 7.98 (dd, 1H, 1.6 and 7.92 Hz), 8.07 (m, 2H). ¹³C NMR δ ppm: 8.46, 23.79, 23.96, 28.32, 32.73, 56.35 (6 sp³C), 114.19, 119.01, 119.37, 120.11, 120.20, 120.81, 120.86, 121.34, 121.51, 122.88, 124.87, 125.03, 125.23, 127.24, 127.94, 128.47, 129.00, 131.03, 133.51, 134.90, 139.69, 144.84, 147.24, 147.54, 148.48, 150.38, 151.93, 154.27 and 168.97 (29 sp²C).

Example 22: 2-Isopropyl Iodobenzene

2-Isopropyl aniline (27.04 g, 0.2 mole) was diazotised in 25% sulfuric acid (w/w 160 mL), with sodium nitrite (14 g) in water (26 mL) at −20° C. This was transferred to potassium iodide (100 g) in water (100 mL), and after 18 hours, sodium hydroxide (36 g) and water (125 mL) were added. The mixture was extracted with hexanes, and the hexanes extract was passed through a column of silica gel, and concentrated, 35.8 g (73%). Mass spec: m/z 246 (M⁺). ¹H NMR (CDCl₃) δ ppm: 1.23 (d, 6H, 6.84 Hz), 3.18 (septet, 1H, 6.84 Hz), 6.86 (m, 1H), 7.28 (m, 2H), 7.82 (dd, 1H, 1.24 and 7.92 Hz).

Example 23: N,7-[(benzothiazol-2-yl)-9,9-diethyl-fluoren-2-yl]-N-(2,6-diisopropylphenyl)-N-(2-isopropylphenyl)amine (AF-338-21)

A mixture of N,7-[(benzothiazol-2-yl)-9,9-diethylfluoren-2-yl)-N-(2,6-diisopropylphenyl)amine (Example 19; 4.24 g, 8 mmol), 2-isopropyl iodobenzene (12.3 g, 50 mmol), 18-crown-6 (0.169 g), copper powder (1 g, 15.7 mmol) and potassium carbonate (4.41 g, 32 mmol) was kept at 240° C. for 4 hours under nitrogen, cooled, diluted with toluene and filtered. The filtrate was washed with water, dried and concentrated. The residue (15.32 g) was chromatographed over silica gel. The column was eluted with 1:1 toluene to get the product, and the product was crystallized from a mixture of isopropanol and toluene, 3.85 g (74%), m.p. 259.3-262.9° C. Mass spec: m/z 648 (M⁺). Anal. Calcd. for $C_{45}H_{48}N_2S$: C, 83.29; H, 7.46; N, 4.32 and S, 4.94%. Found: C, 83.33; H, 7.45; N, 4.31 and S, 4.96%. ¹H NMR (CDCl₃) δ ppm: 0.29, 0.32 (2t, 6H, 7.28, 7.36 Hz), 0.75 (broad envelope 6H), 1.18 (broad, 12H), 1.90 (m, 2H), 2.08 (m, 2H), 3.20 (broad s?, 2H), 3.35 (m, 1H), 6.58 (m, 1H), 6.81 (dd, 1H, 1.32 and 7.88 Hz), 7.08 (m, 2H), 7.23 (m, 3H), 7.34 (m, 3H), 7.47 (m, 2H), 7.62 (d, 1H, 7.92 Hz), 7.88 (d, 1H, 7.88 Hz), 7.99 (m, 2H). ¹³C NMR δ ppm: 8.33, 8.60, 21.46, 23.85, 27.66, 28.00, 28.57, 32.50, 32.90, 56.55 (10 sp³C), 118.89, 119.76, 120.75, 121.30, 121.49, 122.87, 124.27, 124.85, 125.30, 125.78, 126.22, 126.43, 127.18, 127.87, 128.23, 129.04, 130.86, 132.95, 134.91, 142.58, 142.88, 143.53, 145.02, 148.05, 148.19, 150.06, 151.86, 152.06, 154.29 and 169.02 (30 sp²C).

Example 24: 2,6-Diisopropyl-iodobenzene 2,6-Diisopropyl aniline (41.3 g. 0.233 mol) was diazotized in sulfuric acid (25% w/w, 280 mL), using sodium nitrite (16.3 g) in water (30 mL) at −20° C. The diazotized paste was transferred to a solution of potassium iodide (116 g) in water (125 mL). After 18 hours, a solution of sodium hydroxide (84 g) in water (240 mL) was added, and the mixture was extracted with hexanes. The extract was washed with water, dried, and passed through a column of silica gel to get the product after removal of solvents, 49.41 g (73%). Mass spec: m/z 288 (M⁺). ¹H NMR (CDCl₃) δ ppm: 1.23 (d, 12H, 6.8 Hz), 3.41 (septet, 2H, 6.8 Hz), 7.07 (d, 2H, 7.6 Hz), 7.23 (m, 1H).

Example 25: N,7-[(benzothiazol-2-yl)-9,9-diethyl-fluoren-2-yl]-N,N-bis(2,6-diisopropylphenyl)amine (AF338-22)

A mixture of N,7-[(Benzothiazol-2-yl)-9,9-diethylfluoren-2-yl)-N-(2,6-diisopropylphenyl)amine (Example 19; 5.31 g, 10 mmol), 2,6-diisopropyl iodobenzene (18 g, 62.5 mmol), 18-crown-6 (0.2 g), copper powder (1.25 g, 19.7 g atom), and potassium carbonate (5.5 g, 39.9 mmol) was heated to 250° C., and held at this temperature for 9 hours. After cooling, the reaction mass was diluted with toluene and filtered. The filtrate was washed with water, and the organic phase was dried and concentrated. The residue was chromatographed successively twice over silica gel and the product was eluted with 3:1 toluene-heptane, 1.58 g (26%). Mass spec: m/z 690 (M⁺). Anal. Calcd. for $C_{48}H_{54}N_2S$: C, 83.43; H, 7.88; N, 4.05 and S 4.64%. Found: C, 83.46; H, 7.75; N, 3.79 and S, 4.21%. ¹H NMR is too complex to interpret, and the carbon spectrum has too many peaks. The sample shows two fluorene tertiary carbon, at 55.90 and 56.45 suggesting that the sample is a mixture of two compounds or the presence of at least two conformationally-rigid isomers.

Example 26: N,7-[(benzothiazol-2-yl)-9,9-diethyl-fluoren-2-yl]-N-(2-t-butylphenyl)amine A mixture of 2-(7-bromo-9,9-diethylfluoren-2-yl)benzothiazole (Example 4; 10.85 g, 25 mmol), 2-t-butylaniline (4.8 g, 32.2 mmol), and toluene (125 mL) was azeotroped dry under nitrogen and cooled. Palladium (II) acetate (59.3 mg, 0.264 mmol), DPE Phos (207.2 mg, 0.385 mmol), and sodium t-butoxide were then added, and the mixture was held at 98° C. for 3.5 hours. On cooling, the product (10.64 g) was filtered, and washed with water. Recrystallization from a mixture of toluene and heptane, gave purer product, 9.58 g, m.p. 213-215° C. The crystallization mother liquor and the original toluene filtrate after washing and drying were passed through a column of silica gel. Elution with 3:1 toluene-heptane gave additional product, 1.9 g, m.p. 212-214° C. Total recovery of the product was 11.5 g (88%).

Mass spec: m/z 502 (M⁺). Anal. $C_{34}H_{34}N_2S$: C, 81.23; H, 6.82; N, 5.57 and S, 6.34%. Found: C, 81.26; H, 6.73; N, 5.59 and S, 6.29%. ¹H NMR (CDCl₃) δ ppm: 0.38 (t, 6H, 7.32 Hz), 1.45 (s, 9H), 1.96 (m, 2H), 2.10 (m, 2H), 5.58 (s, 1H), 6.78 (m, 2H), 7.10 (M, 1H), 7.21 (m, 1H), 7.35 (m, 2H), 7.48 (m, 2H), 7.57 (d, 1H, 8.12 Hz), 7.63 (d, 1H, 7.88 HZ), 7.89 (d, 1H, 7.96 Hz), 7.98 (dd, 1H, 1.64 and 7.92 Hz), 8.07 (m, 2H). ¹³C NMR δ ppm: 8.58, 30.61, 32.81, 34.92, 56.27 (5 sp³C), 110.21, 115.07, 118.61, 121.22, 121.33, 121.49, 122.84, 124.24, 124.81, 126.20, 127.01, 127.17, 127.26, 130.66, 132.21, 134.90, 141.03, 143.67, 145.23, 146.56, 150.01, 152.70, 154.30 and 169.10 (24 sp²C).

Example 27: N,7[(benzothiazol-2-yl)-9,9-diethyl-fluoren-2-yl]-(2-t-butylphenyl)phenylamine (AF339-10)

A mixture of N,7-[(benzothiazol-2-yl)-9,9-diethylfluoren-2-yl]-N-(2-t-butylphenyl)amine (Example 25; 2.51 g, 5 mmol), bromobenzene (3.14 g, 20 mmol), and toluene (50 mL) was azeotroped dry under nitrogen and cooled. Pd(dba)₂ (67.1 mg, 0.117 mmol), 2-di-t-butylphosphino biphenyl (68.7 mg, 0.23 mmol) and sodium t-butoxide (2.02 g, 21 mmol) were added, and the reaction mass was held at 93° C. for 21 hours. After cooling and dilution with toluene, the toluene solution was washed with water, dried, and concentrated. The residue (6.62 g) was chromatographed over silica gel and the column was eluted with 1:1 toluene-heptane to get the product. The product was crystallized from a mixture of isopropanol and toluene, 2.46 g (85%), m.p. 193-195° C. Mass spec: m/z 578 (M⁺). Anal. Calcd. for $C_{40}H_{38}N_2S$: C, 83.00; H, 6.62; N, 4.84 and S, 5.54%. Found: C, 82.95; H, 6.70; N, 4.86 and S 5.45%. ¹H NMR (CDCl₃) δ ppm: 0.37 (2 overlapping triplets, 6H, 7.22 and 6.92 Hz), 1.26 (s, 9H), 1.92 (M, 2H), 2.06 (m, 2H), 6.91 (m, 2H), 7.04 (m 3H), 7.09 (m, 1H), 7.22 (m, 2H), 7.31 (m, 3H), 7.48 (dt, 1H, 1.16 and 7.28 Hz), 7.56 (d, 1H, 8.28 Hz), 7.60 (dd, 1H, 1.6 and 7.92 Hz), 7.66 (d, 1H, 7.92 Hz), 7.89 (d, 1H, 7.6 Hz), 7.99 (dd, 1H, 1.6 and 7.92 Hz), 8.07 (m, 2H). ¹³C NMR δ ppm: 8.48, 8.56, 31.41, 32.65, 32.67, 35.77, 56.32 (7 sp³C), 116.39, 119.16, 120.66, 121.06, 121.15, 121.43, 121.52, 122.92, 124.90, 126.24, 127.04, 127.23, 127.74, 128.80, 129.58, 131.22, 133.85, 134.04, 134.94, 144.71, 144.79, 148.50, 148.55, 148.81, 150.57, 157.75, 154.30 and 168.93 (28 sp²C).

Example 28: 2-t-Butyliodobenzene 2-t-Butylaniline (13.35 g, 89.4 mmol) was diazotized in sulfuric acid (25% w/w, 110 mL) with sodium nitrite (9.34 g) in water (18 mL) at −20° C. The diazonium salt was transferred to a solution of potassium iodide (67 g) in water 20 mL, and after 18 hours, a solution of sodium hydroxide (25 g) in water (100 mL) was added. The mixture was extracted with hexanes, hexane extracts passed through a column of silica gel, and concentrated. The product was obtained as a liquid, 13.77 g (59%). Mass spec: m/z 260 (M⁺). ¹H NMR (CDCl₃) δ ppm: 1.53 (s, 9H), 6.82 (td, 1H, 1.68 and 7.68 Hz), 7.27 (td, 1H, 1.4 and 7.32 Hz), 7.43 (dd, 1H, 1.64 and 8.0 Hz), 7.99 (dd, 1.4 and 7.8 Hz).

Example 29: N,7-[(benzothiazol-2-yl)-9,9-diethyl-fluoren-2-yl]-N,N-bis(2-tert-butylphenyl)amine (AF339-11)

A mixture of N,7-[(benzothiazol-2-yl)-9,9-diethylfluoren-2-yl]-N-(2-t-butylphenyl)amine (Example 25; 3.77 g, 7.5 mmol), 2-t-butyliodobenzene (7 g, 27 mmol), 18-crown-6 (0.12 g), copper powder (0.8 g, 12.6 g. atom), and potassium carbonate (2.77 g, 20 mmol), was held at 205-225° C. for 11 hours, cooled, and diluted with toluene. The mixture was filtered, and the filtrate was washed with water, dried and concentrated. The residue (7.98 g) was chromatographed over silica gel, and the column was eluted with 1:1 toluene-heptane to get the product. The product was crystallized from a mixture of isopropanol and toluene, 1.4 g (37%), m.p. 213.4-215.9° C. Mass spec: m/z 634 (M⁺). Anal. Calcd. for $C_{44}H_{46}N_2S$: C, 83.24; H, 7.30; N, 4.41 and S, 5.05%. Found: C, 83.23; H, 7.28; N, 4.45 and S, 4.97%. ¹H NMR (CDCl₃) δ ppm: 0.26-0.36 (7 peaks, methyl hydrogens), 1.23, 1.29 (doublet? 9H), 1.34, 1.35 (d, 9H, 3.92 Hz), 1.80-1.91 (m, 2H), 2.01-2.35 (m, 2H), 6.40-6.46 (m, 1H), 6.71, 6.74, 6.80 (not integrated broad, 2H), 7.06-7.24 (m, 5H), 7.33-7.38 (m, 1H), 7.45-7.61 (m 5H), 7.87-7.89 (m, 1H), 7.96-8.1 (m, 1H). ¹³C NMR δ ppm: 8.22, 8.45, 8.55, 8.72, 25.37, 32.29, 32.61, 32.67, 32.73, 32.92, 33.00, 36.27, 36.52, 36.68, 56.33, 56.39 (16 sp³C), 112.11, 117.46, 118.62, 119.22, 120.29, 120.80, 121.21, 121.36, 121.47, 121.50, 122.81, 122.90, 124.79, 124.90, 125.21, 125.30, 125.50, 126.18, 126.23, 126.57, 127.00, 127.12, 128.16, 128.23, 129.04, 130.51, 131.23, 131.70, 131.91, 131.94, 132.28, 134.34, 134.88, 134.92, 143.93, 144.67, 144.74, 145.31, 146.03, 146.36, 149.82, 150.50, 151.51, 152.12, 154.24, 154.27, 154.29, 157.11, 168.94 and 169.13. Sample appears to be isomeric mixture of at least two compounds, possibly rotational isomers.

In addition to the foregoing, other exemplary TPA compounds of the present invention were prepared and characterized. A summary of the exemplary TPA compounds, as well as their molecular structure and physical properties, is provided in Table 1.

TABLE 1

Molecular Structures and physical properties of a series of AF-240 derivatives with varied numbers of ortho-alkyl substituents.

| AFX | Molecular Structure | Physical Properties | $\lambda_{max}$ 2PA (nm) | Cross-section (GM) |
|---|---|---|---|---|
| AF-240 | 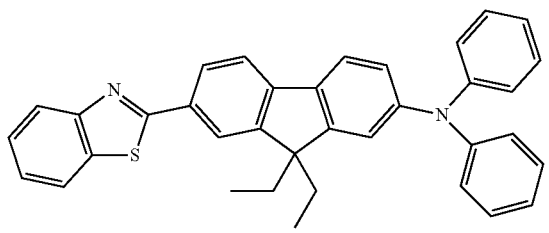 [SMILES: CCC1(CC)c2cc(-c3nc4ccccc4s3)ccc2-c2ccc(N(c3ccccc3)c3ccccc3)cc21] | | 825 | 565 |

TABLE 1-continued

Molecular Structures and physical properties of a series of AF-240 derivatives with varied numbers of ortho-alkyl substituents.

| AFX | Molecular Structure | Physical Properties | $\lambda_{max}$ 2PA (nm) | Cross-section (GM) |
|---|---|---|---|---|
| AF-331-11 | 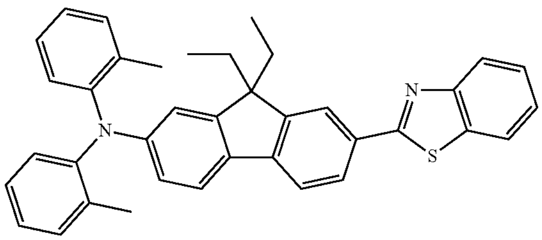 [SMILES: CCC1(CC)c2cc(-c3nc4ccccc4s3)ccc2-c2ccc(N(c3ccccc3C)c3ccccc3C)cc21] | MP 203-204° C.<br>Sol: PhMe, THF, CH$_2$Cl$_2$<br>Recrystallized: 60% heptanes/PhMe<br>MW = 550.75 | 765 | 145 |
| AF-331-20 | 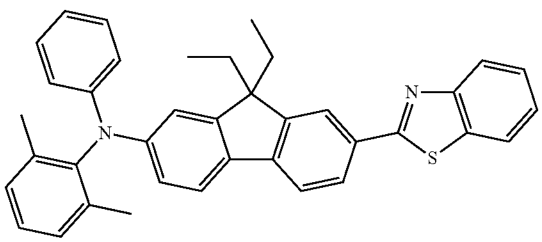 [SMILES: CCC1(CC)c2cc(-c3nc4ccccc4s3)ccc2-c2ccc(N(c3ccccc3)c3c(C)cccc3C)cc21] | MP 225.5-227° C.<br>Sol: PhMe, THF, CH$_2$Cl$_2$<br>MW = 550.75<br>Recrystallized: IPA/PhMe<br>MW = 550.75 | 760 | 225 |
| AF-331-21 | 2009-54 | MP 245-247° C.<br>Sol: PhMe, THF, CH$_2$Cl$_2$<br>Recrystallized: 1:1 IPA/PhMe<br>MW = 564.78 | 760 | 145 |
| AF-331-22 | 2009-55 | MP 236-237.5° C.<br>Sol: PhMe, THF, CH$_2$Cl$_2$<br>Recrystallized: 1:1 IPA/PhMe<br>MW = 578.81 | 776 | 135 |
| AF-337-11 | 2009-60 | MP 166.5-168° C.<br>Recrystallized: IPA/PhMe<br>Sol: PhMe, THF, CH$_2$Cl$_2$<br>MW = 578.81 | 780 | 136 |

TABLE 1-continued

Molecular Structures and physical properties of a series of AF-240 derivatives with varied numbers of ortho-alkyl substituents.

| AFX | Molecular Structure | Physical Properties | $\lambda_{max}$ 2PA (nm) | Cross-section (GM) |
|---|---|---|---|---|
| AF-337-20 | 2009-70 | MP 170 -171.5° C. Recrystallized: 1:1 IPA/PhMe Sol: PhMe, THF, $CH_2Cl_2$ MW = 578.81 | 790 | 171 |
| AF-337-21 | 2009-74 | MP 206-208° C. Recrystallized: 1:1 IPA/PhMe Sol: PhMe, THF, $CH_2Cl_2$ MW = 606.86 | 795 | 158 |
| AF-337-22 | 2009-88 | MP 223.6-226.1° C. Recrystallized: heptanes? Sol: PhMe, THF, $CH_2Cl_2$ sparingly sol in cold heptanes. MW = 634.91 | 782 | 157 |
| AF-338-11 | 2009-68 | MP 206-208° C. Recrystallized: IPA/PhMe Sol: PhMe, THF, $CH_2Cl_2$ MW = 606.86 | 750 762 | 240 210 |

TABLE 1-continued

Molecular Structures and physical properties of a series of AF-240 derivatives with varied numbers of ortho-alkyl substituents.

| AFX | Molecular Structure | Physical Properties | $\lambda_{max}$ 2PA (nm) | Cross-section (GM) |
|---|---|---|---|---|
| AF-338-20 | 2009-62 | MP 217-218.5° C. Recrystallized: IPA/PhMe Sol: PhMe, THF, CH$_2$Cl$_2$ MW = 606.86 | 775 | 272 |
| AF-338-21 | 2009-62 | MP 259.3-262.9° C. Recrystallized: IPA/PhMe Sol: readily in THF, CH$_2$Cl$_2$; with warming in PhMe, 15-20%, MW = 648.94 | 774 | 150 |
| AF-339-10 | 2009-65 t-Bu = t-butyl (—CMe$_3$) | MP 193-195° C. Recrystallized: IPA/PhMe Sol: readily in THF, CH$_2$Cl$_2$; with warming in PhMe, 15-20%,; MW = 578.81 | 770 | 153 |
| AF-339-11 | 2009-79 t-Bu = t-butyl (—CMe$_3$) | MP 247.5-248.9° C. Recrystallized: IPA/PhMe Sol: readily in THF, CH$_2$Cl$_2$; with warming in PhMe, 15-20%, MW = 643.91 | 775 | 140 |

Figure 5:
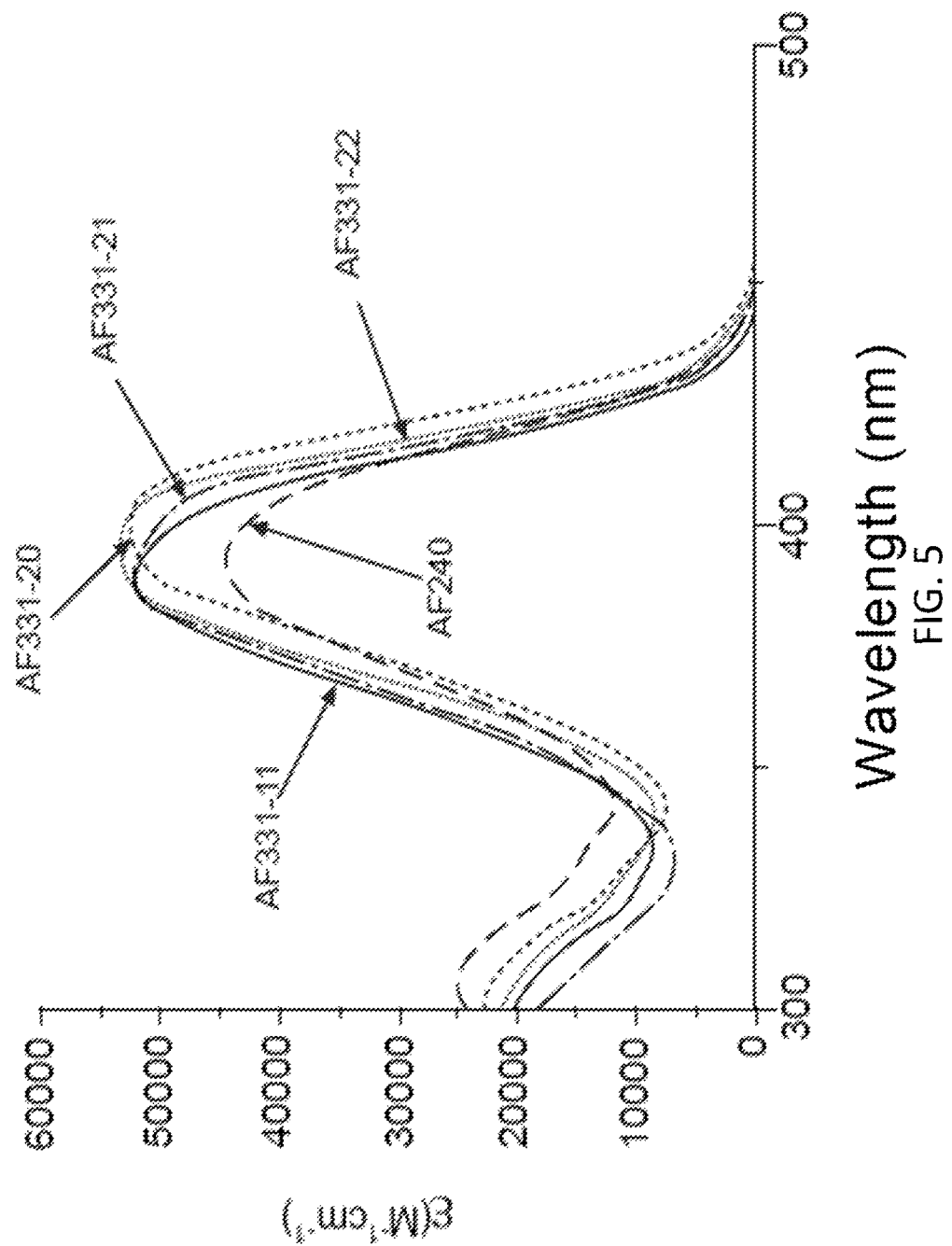
FIG. 5 is a plot of molar attenuation coefficient ($M^{-1} \cdot cm^{-1}$) versus wavelength (nm) showing a linear absorption spectra of an ortho-methylated series of TPA compounds.
Figure 6:
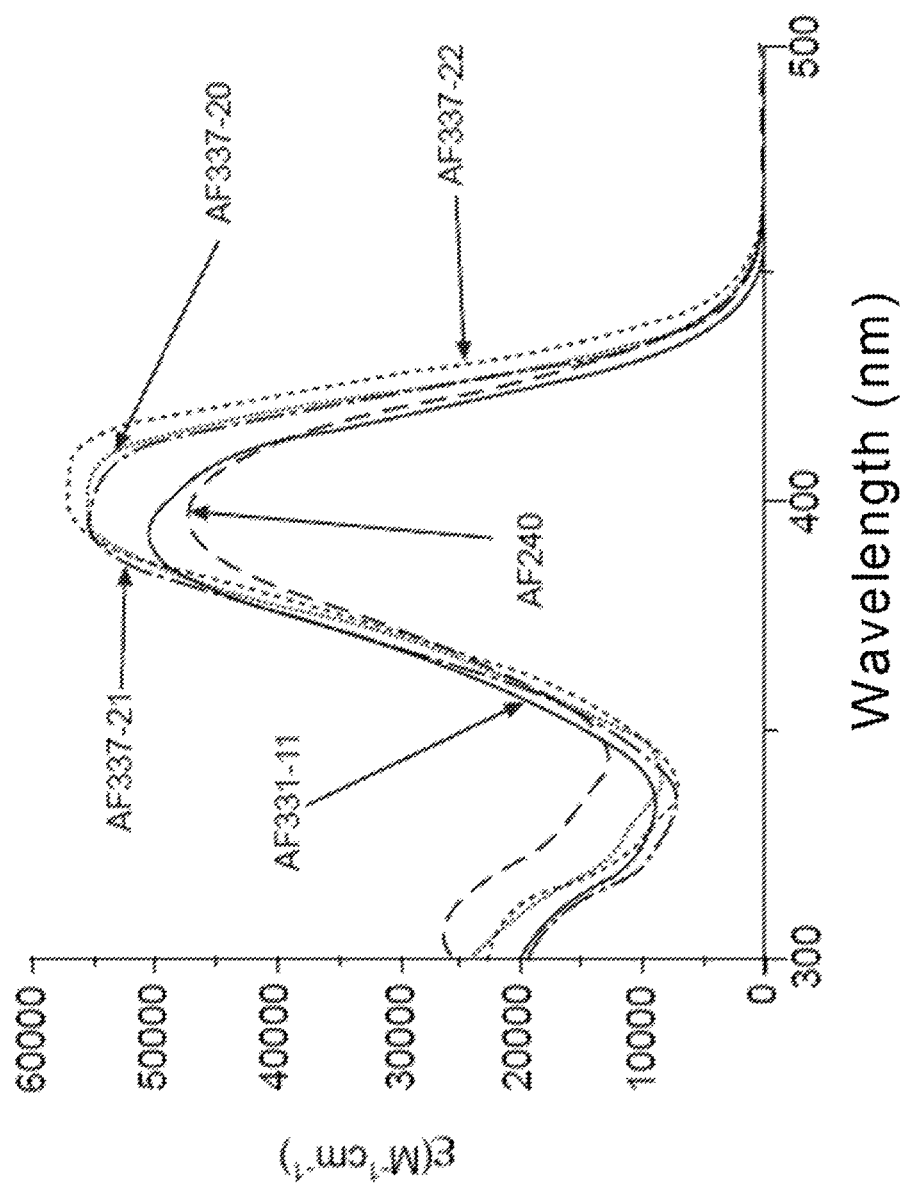
FIG. 6 is a plot of molar attenuation coefficient ($M^{-1} \cdot cm^{-1}$) versus wavelength (nm) showing a linear absorption spectra of an ortho-ethylated series of TPA compounds.
Figure 7:
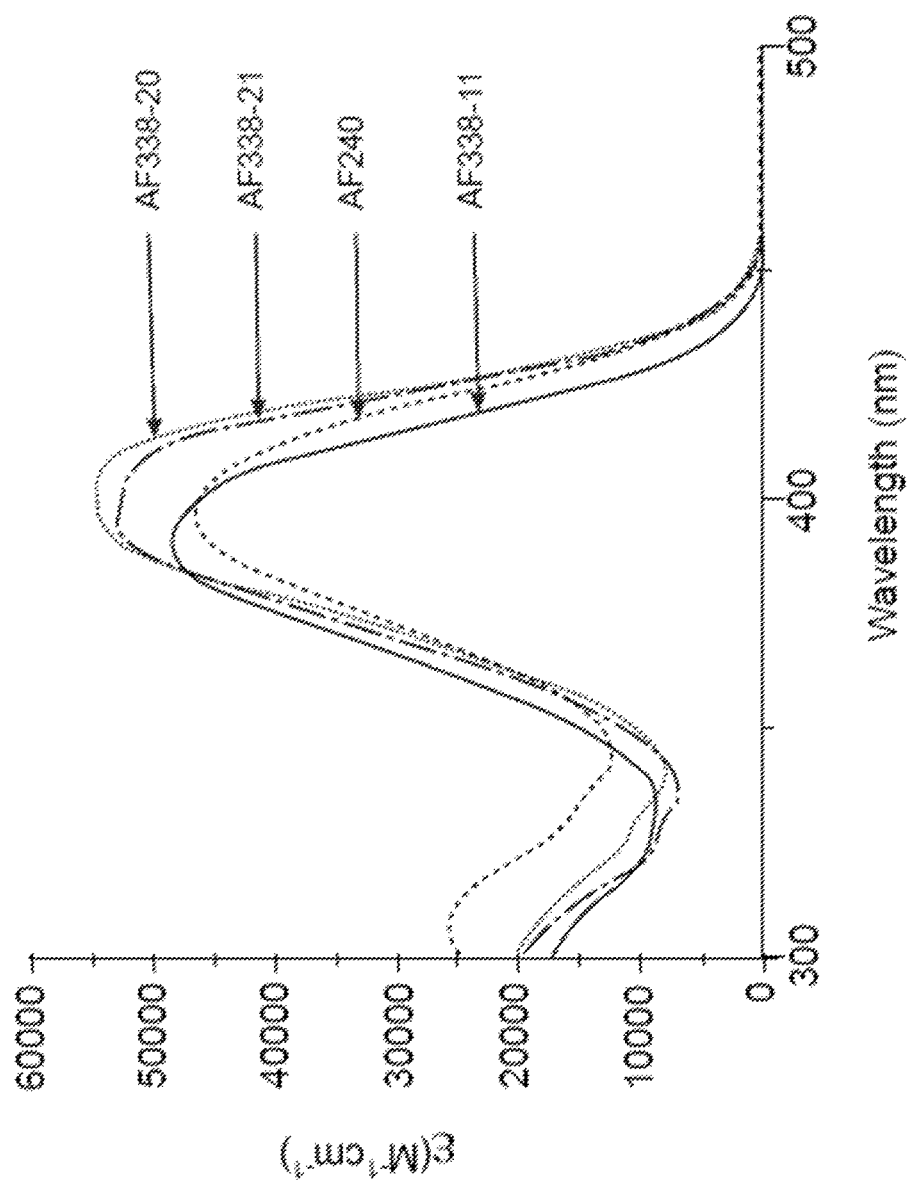
FIG. 7 is a plot of molar attenuation coefficient ($M^{-1} \cdot cm^{-1}$) versus wavelength (nm) showing a linear absorption spectra of an ortho-isopropylated series of TPA compounds.
Figure 8:
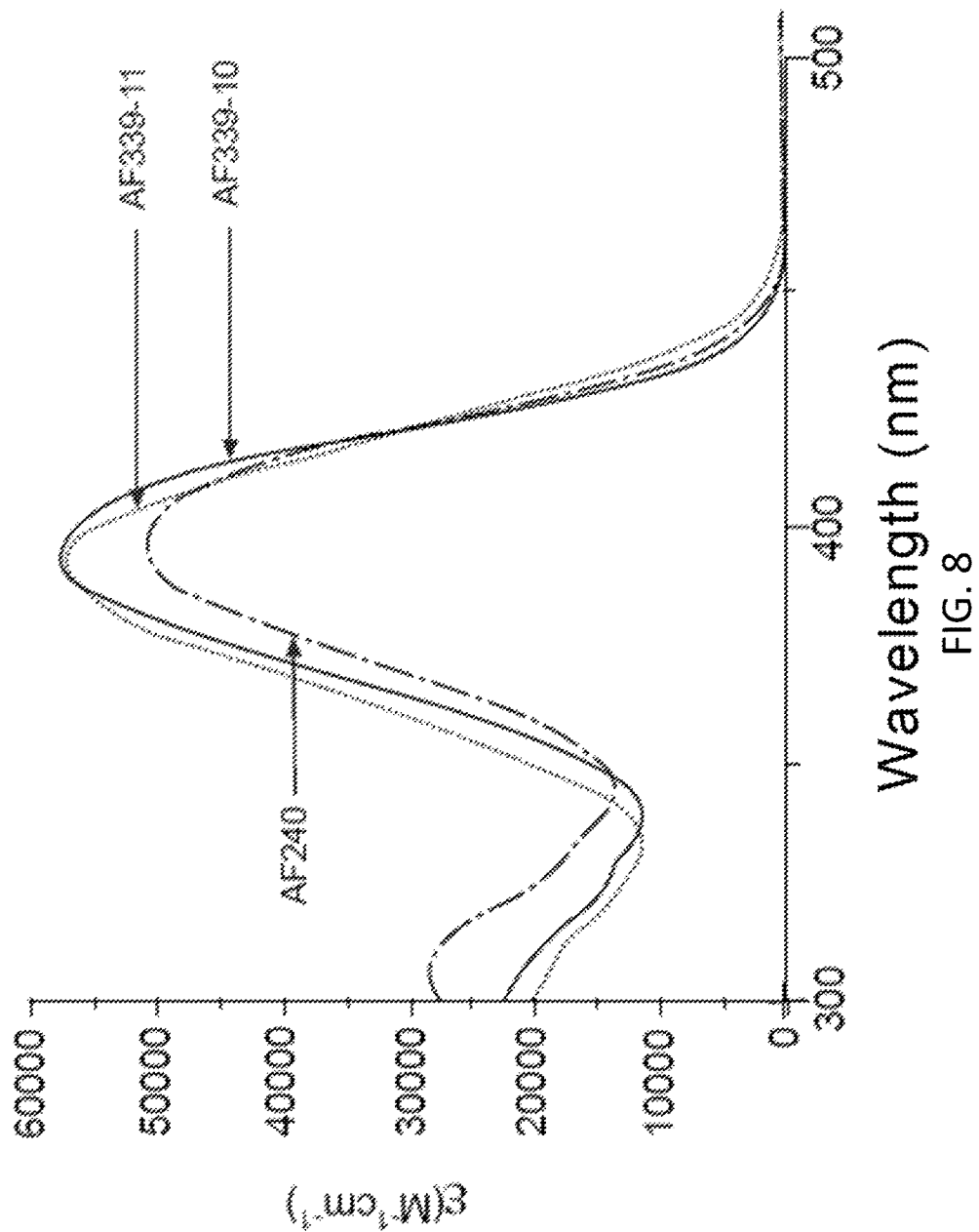
FIG. 8 is a plot of molar attenuation coefficient ($M^{-1} \cdot cm^{-1}$) versus wavelength (nm) showing a linear absorption spectra of an ortho-t-butylated series of TPA compounds.

Ground state absorbance spectra were taken for all chromophores in THF (FIGS. 5-8). FIG. 5 is a plot of molar extinction coefficient (M$^{-1}$·cm$^{-1}$) versus wavelength (nm) showing a linear absorption spectra of an ortho-methylated series of TPA compounds. FIG. 6 is a plot of molar extinction coefficient (M$^{-1}$·cm$^{-1}$) versus wavelength (nm) showing a linear absorption spectra of an ortho-ethylated series of TPA compounds. FIG. 7 is a plot of molar extinction coefficient (M$^{-1}$·cm$^{-1}$) versus wavelength (nm) showing a linear absorption spectra of an ortho-isopropylated series of TPA compounds. FIG. 8 is a plot of molar extinction coefficient (M$^{-1}$·cm$^{-1}$) versus wavelength (nm) showing a linear absorption spectra of an ortho-t-butylated series of TPA compounds. Overall, the spectral shape is similar for all the chromophores, and there are only small shifts (3-4 nm) observed in the peak maximum and small differences in the molar absorption coefficients among a series. Comparing to AF240, these sterically-hindered derivatives all have higher molar absorption coefficients (>44,400 M$^{-1}$cm$_{-1}$). However, within the series with same alkyl group, higher number of alkyl groups tends to have slightly larger and more red-shifted absorption.

Steady state emission studies were done for each chromophore exciting at 355 nm. The results are shown below for each group. The data is directly comparable because all samples were made up to the same absorbance at 355 nm. In addition the fluorescence quantum yield was measured for each chromophore and these values are given in Table 2 (see below) with their peak maximum. All of the ortho-alkylated AFX chromophores have fluorescence peak blue-shifted by 8-15 nm, and larger fluorescence quantum yields (0.87-0.95±0.01) than AF240 (quantum yield=0.73±0.05 at 475 nm).

Time correlated single photon counting (TCSPC) was also utilized to measure the singlet excited state lifetimes in air saturated THF. In this experiment the samples are excited with a 70 ps, 375 nm pulse and the emission is monitored at the peak. All of the lifetimes of the ortho-alkylated AFX chromophores are consistently around 1.7 ns and shorter than that of the unsubstituted AF240 (2.2 ns).

Nanosecond laser flash photolysis was conducted to probe the triplet excited state of these AFX chromophores, which were excited at 355 nm in deoxygenated THF and probed by scanning from 350-850 nm. For all the compounds intersystem crossing to the triplet excited state is small based on the weak signal measured. Also we do know that for AF240 in THF that intersystem crossing is 0.064±0.007. We expect the others to follow a similar trend. At this time we have not determined either triplet molar absorption coefficients or intersystem crossing quantum yields for the series. The data is shown below for each chromophore separately due to noisy spectra. The peak maximum and lifetime for each chromophore are given in Table 2.

TABLE 2

Absorbance and Emission Properties of Sterically-Hindered AF240 in THF.

|  | Abs $_{max}$ | ε(M$^{-1}$ cm$^{-1}$) | Fl $_{max}$ | Φ$_{fl}$ (air sat) | τ$_s$ |
|---|---|---|---|---|---|
| AF331-11 | 388 nm | 52100 ± 1000 | 463 nm | 0.93 ± 0.01 | 1736 ps |
| AF331-20 | 394 nm | 53300 ± 2300 | 463 nm | 0.92 ± 0.01 | 1749 ps |
| AF331-21 | 388 nm | 52000 ± 700 | 460 nm | 0.95 ± 0.01 | 1643 ps |
| AF331-22 | 398 nm | 52200 ± 700 | 468 nm | 0.87 ± 0.01 | 1897 ps |
| AF337-11 | 388 nm | 47400 ± 500 | 462 nm | 0.89 ± 0.01 | 1712 ps |
| AF337-20 | 395 nm | 54200 ± 800 | 463 nm | 0.88 ± 0.01 | 1725 ps |
| AF337-21 | 390 nm | 52200 ± 2000 | 460 nm | 0.88 ± 0.01 | 1666 ps |
| AF337-22 | 398 nm | 53600 ± 2000 | 462 nm | 0.90 ± 0.01 | 1747 ps |
| AF338-11 | 387 nm | 46600 ± 1000 | 461 nm | 0.91 ± 0.01 | 1733 ps |
| AF338-20 | 395 nm | 52000 ± 500 | 461 nm | 0.92 ± 0.01 | 1756 ps |
| AF338-21 | 391 nm | 50600 ± 1000 | 460 nm | 0.96 ± 0.01 | 1719 ps |
| AF339-10 | 389 nm | 50300 ± 1000 | 463 nm | 0.89 ± 0.01 | 1788 ps |
| AF339-11 | 390 nm | 49900 ± 800 | 460 nm | 0.91 ± 0.01 | 1747 ps |
| AF240 | 391 nm | 44400 ± 700 | 475 nm | 0.73 ± 0.05 | 2170 ps |

TABLE 3

Triplet Excited State Properties of Sterically-Hindered AF240 in Deoxygenated THF.

|  | T$_1$-T$_{n\,max}$ | τ$_T$ |
|---|---|---|
| AF331-11 | 465 nm | 138 ± 33 µs |
| AF331-20 | 465 nm | 185 ± 42 µs |
| AF331-21 | 460 nm | 172 ± 24 µs |
| AF331-22 | 465 nm | 217 ± 52 µs |
| AF337-11 | 460 nm | 452 ± 80 µs |
| AF337-20 | 460 nm | 346 ± 116 µs |

TABLE 3-continued

Triplet Excited State Properties of Sterically-Hindered AF240 in Deoxygenated THF.

|  | T$_1$-T$_{n\,max}$ | τ$_T$ |
|---|---|---|
| AF337-21 | 460 nm | 406 ± 85 µs |
| AF337-22 | 460 nm | 317 ± 36 µs |
| AF338-11 | 460 nm | 220 ± 70 µs |
| AF338-20 | 460 nm; 685 nm | 580 ± 112 µs |
| AF338-21 | 460 nm | 519 ± 168 µs |
| AF339-10 | 460 nm | 888 ± 428 µs |
| AF339-11 | 460 nm | 662 ± 112 µs |
| AF240 | 460 nm | 109 ± 17 µs |

Two-Photon Properties

Figure 9:
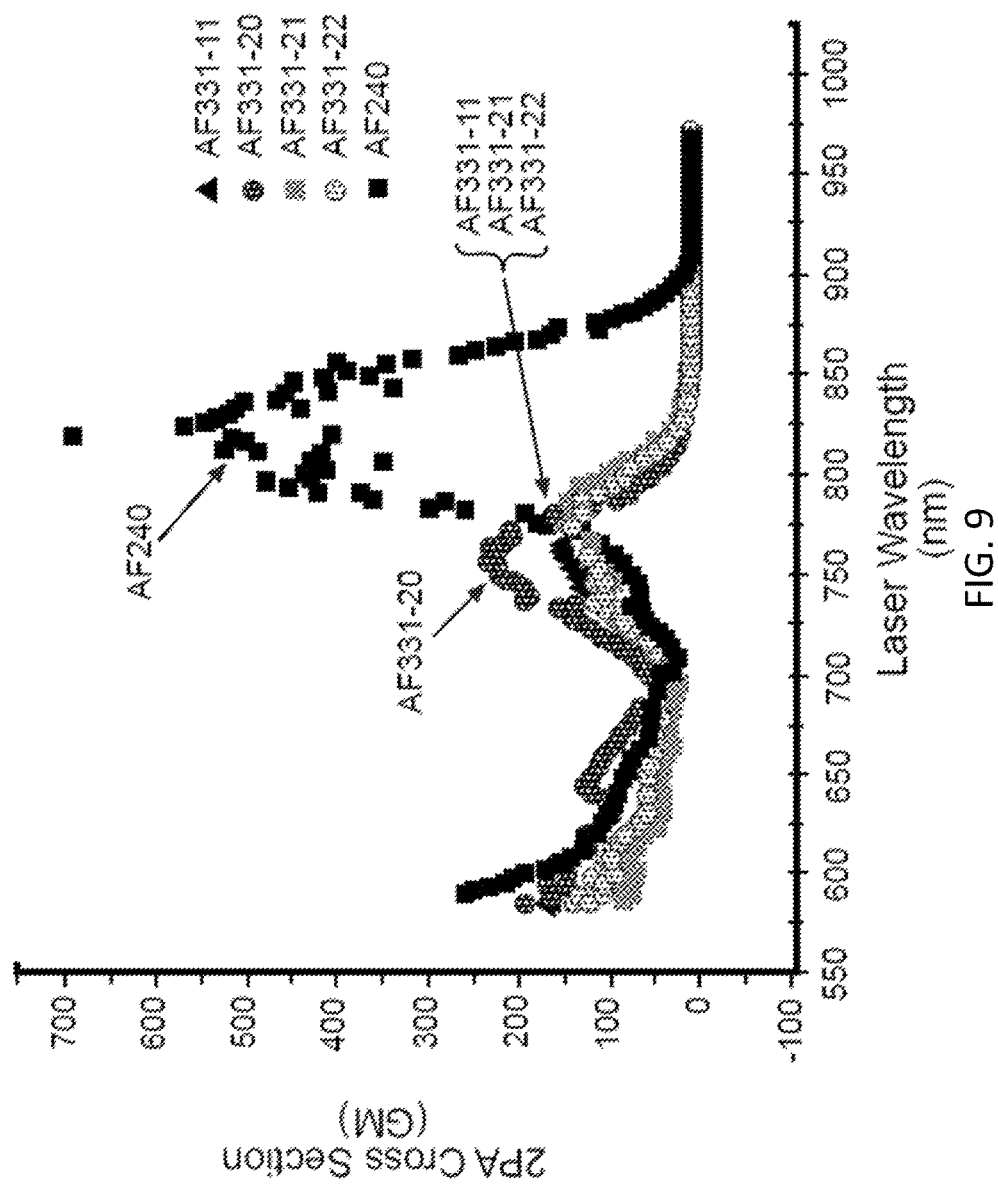
FIG. 9 is a plot of molecular two-photon cross-section (in units of Goeppert-Mayer (GM) versus wavelength (nm) showing a two photon absorption (2PA) spectra of an ortho-methylated series of TPA compounds.
Figure 10:
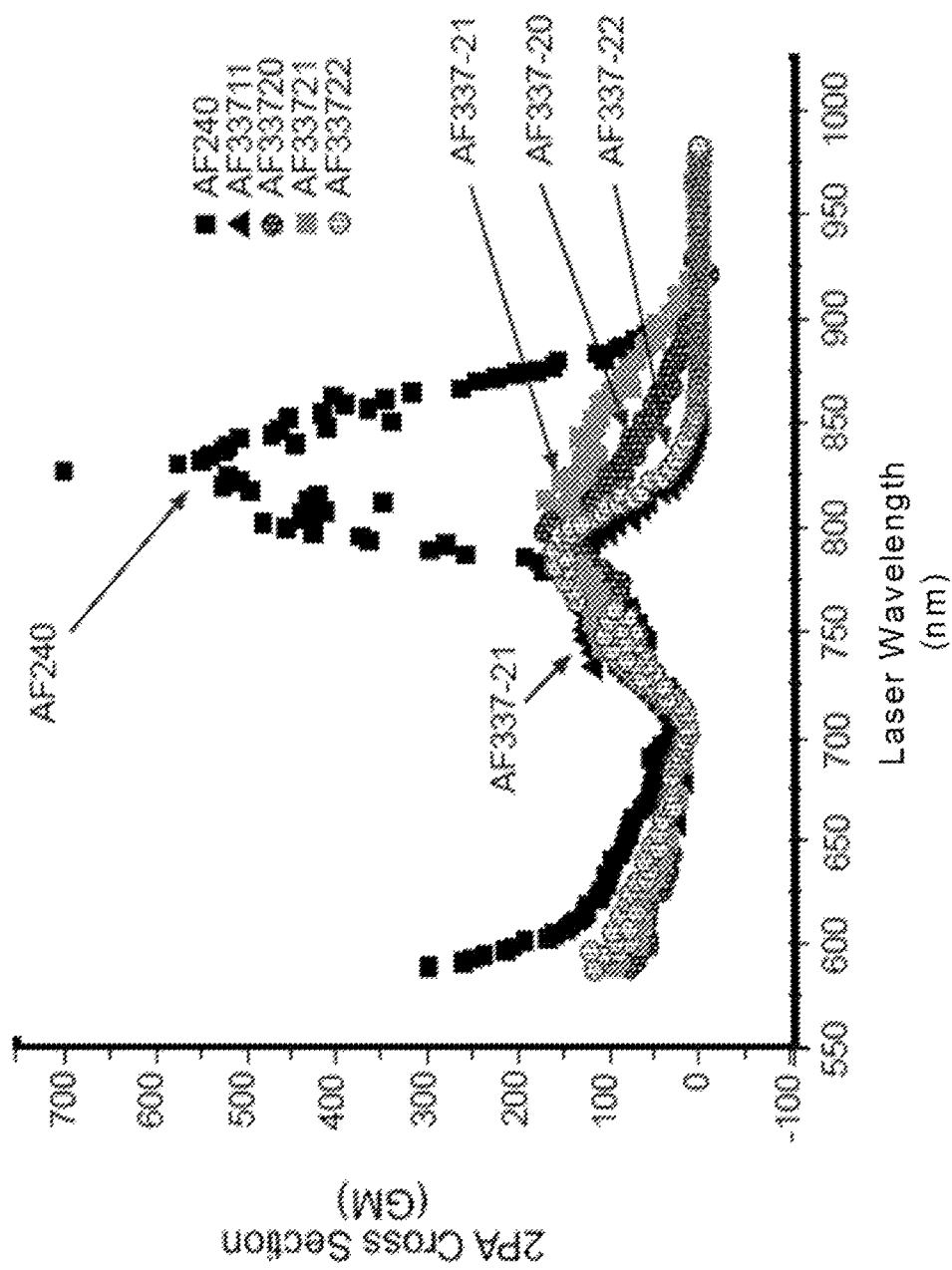
FIG. 10 is a plot of molecular two-photon cross-section (in units of Goeppert-Mayer (GM) versus wavelength (nm) showing a two photon absorption (2PA) spectra of an ortho-ethylated series of TPA compounds.
Figure 11:
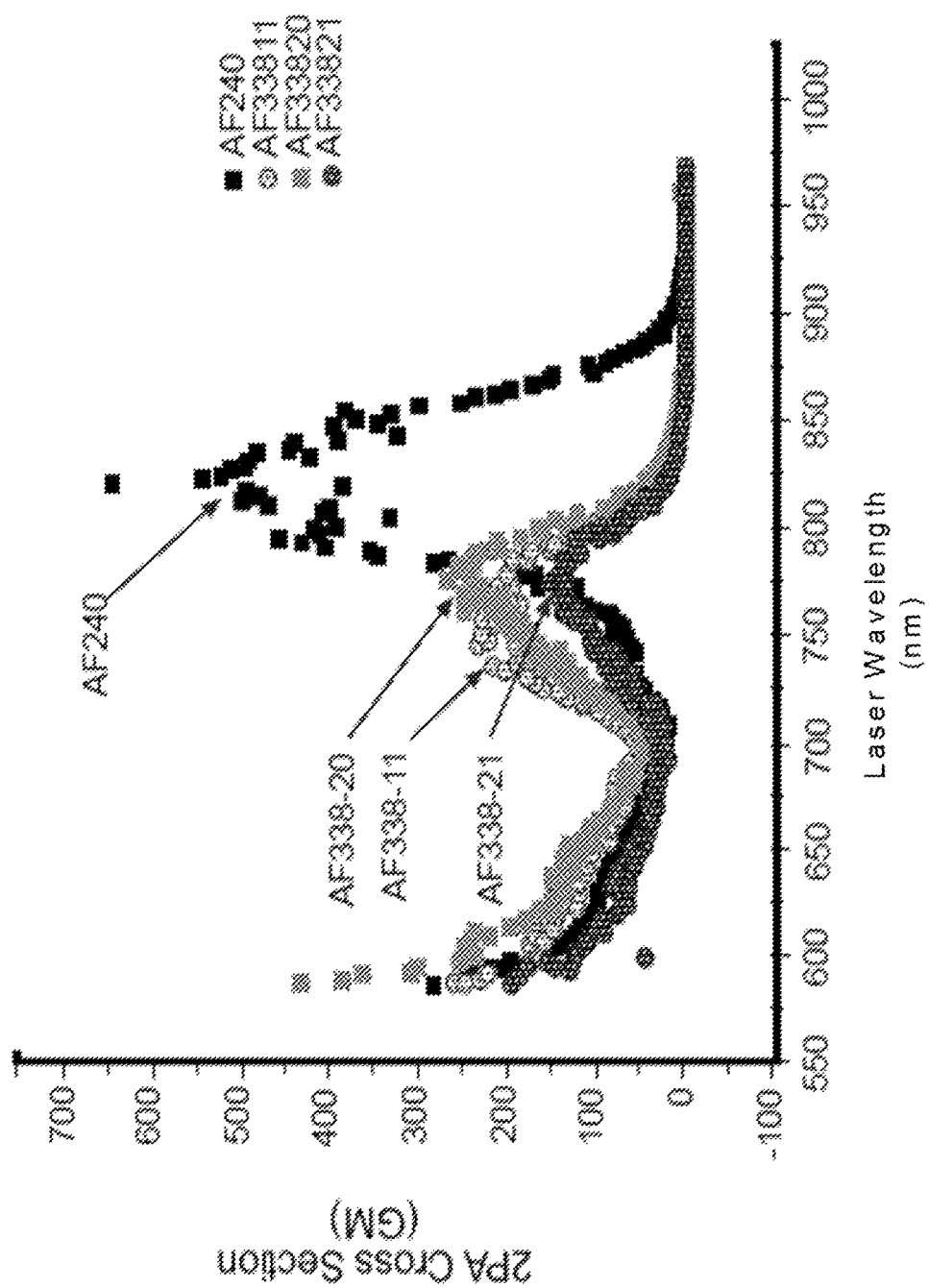
FIG. 11 is a plot of molecular two-photon cross-section (in units of Goeppert-Mayer (GM) versus wavelength (nm) showing a two photon absorption (2PA) spectra of an ortho-isopropylated series of TPA compounds.
Figure 12:
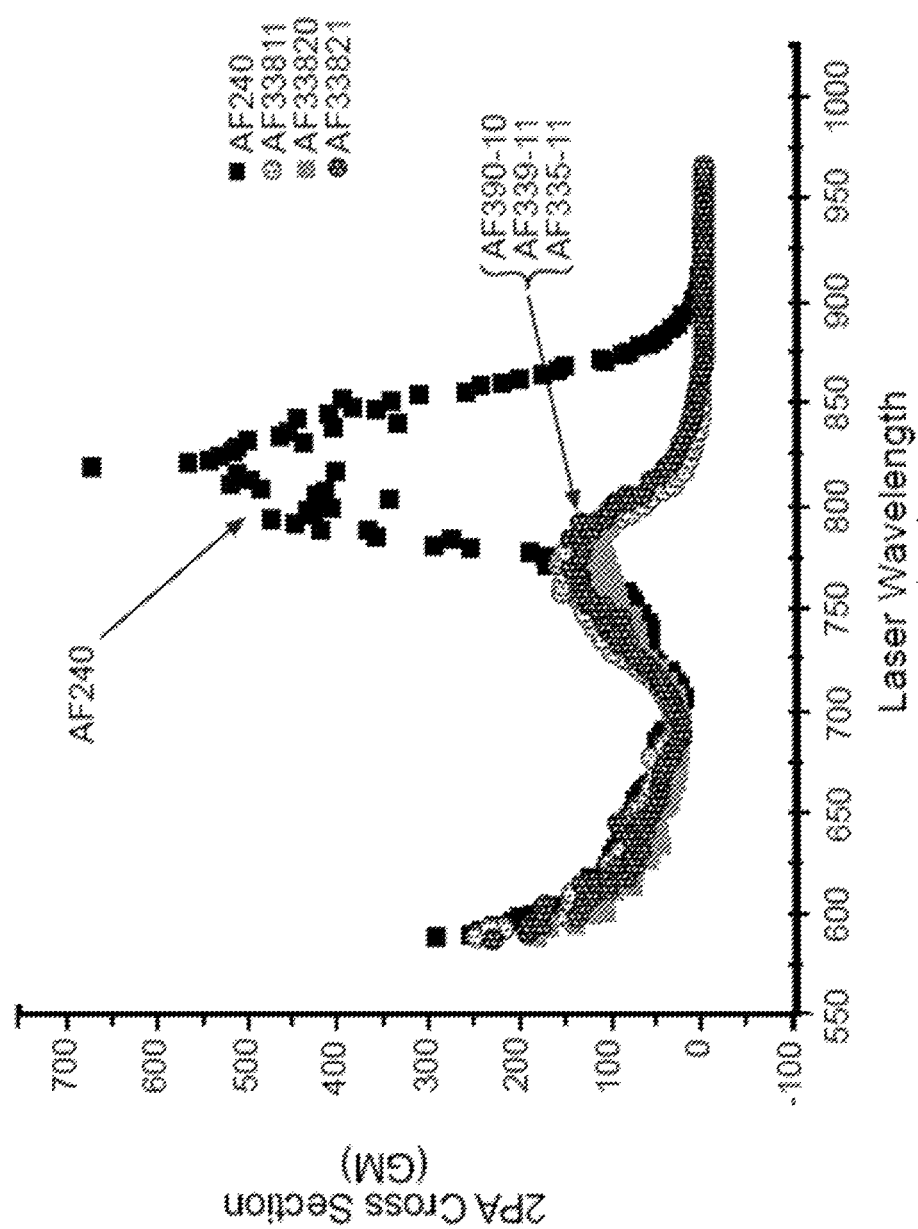
FIG. 12 is a plot of molecular two-photon cross-section (in units of Goeppert-Mayer (GM) versus wavelength (nm) showing a two photon absorption (2PA) spectra of an ortho-t-butylated series of TPA compounds.

Two-photon spectra in THF of these AFX chromophores were obtained by two-photon induced fluorescence technique. FIG. 9 is a plot of molecular two-photon cross-section (in units of Goeppert-Mayer (GM) versus wavelength (nm) showing a two photon absorption (2PA) spectra of an ortho-methylated series of TPA compounds. FIG. 10 is a plot of molecular two-photon cross-section (in units of Goeppert-Mayer (GM) versus wavelength (nm) showing a two photon absorption (2PA) spectra of an ortho-ethylated series of TPA compounds. FIG. 11 is a plot of molecular two-photon cross-section (in units of Goeppert-Mayer (GM) versus wavelength (nm) showing a two photon absorption (2PA) spectra of an ortho-isopropylated series of TPA compounds. FIG. 12 is a plot of molecular two-photon cross-section (in units of Goeppert-Mayer (GM) versus wavelength (nm) showing a two photon absorption (2PA) spectra of an ortho-t-butylated series of TPA compounds. As shown (FIGS. 9-12) in the two-photon spectra of the alkylated derivatives in comparison with that of the parent molecule (AF240), the two-photon absorption peaks are all blue-shifted, i.e. toward shorter wavelengths relative to the AF240 peak and at the same time the cross-section values were significantly reduced, but still remained in the range (>100 GM, see Table 3) for practical uses, such as two-photon fluorescence imaging.

In a comprehensive study on two comparative series of two-photon active molecules containing triarylamino donor and diarylborane acceptor with a simple phenylene as 7-connector, Makarov et al. have examined the effects of planarizing the triarylamino donor in the molecular structures that were systematically varied from linear dipolar, bent quadrupolar and then to octupolar geometry. By comparing the linear and two-photon optical properties of these structurally related molecules, a series of which has the phenyls of triarylamine group free to undergo hindered torsion while the other series has planarized triarylamine whose phenyl groups were "locked" across all ortho positions with the 2,2-isopropyl bridges. In the case of linear dipolar case, they found that (i) both one-photon and two-photon absorption peaks were red-shifted (1PA, charge-transfer or CT band: from 379 to 407 nm and 2PA peak: from 758 to 814 nm) and (ii) little change was observed in both CT band extinction coefficients and 2PA cross-section (~32 GM for peak value) when the triaryamino donor was locked into a planar configuration. Thus, a conclusion of this work is that there is insignificant sensitivity of both 1P & 2P processes when the triarylamine donor is essentially planarized with N being nearly sp$^2$-hybridized. In our class of TPA compounds, a significant influence on 2PA process as manifested by the relatively large sensitivity variation (both wavelength and cross-section) is evidently arisen from the steric congestion caused by the alkyl groups at the ortho positions of the triarylamino donor.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

Example 30. 2-bromo-7-chloro-9H-fluorene

To a mechanically stirred slurry of 2-bromofluorene (25.00 g, 0.102 mol), a mixture of N-chlorosuccinimide (13.6 g, 0.102 mol), acetonitrile (250 mL), and concentrated hydrochloric acid (25 mL) was added drop-wise over a 30-min period, keeping the temperature below 40° C. The mixture was stirred for 24 hours, and then heated to reflux and held at reflux temperature for 2 hours, when the thick slurry became thin. The heavy solids that separated on cooling were collected, washed with plenty of water, 20.61 g, m.p. 145.6-147.5° C. The crude product was recrystallized from a mixture of isopropanol and toluene (4:1) to get colorless crystals, 15.63 g (55% yield), m.p. 148.5-150.0° C. Mass Spec: m/z 278, 280, 282. $^1$H NMR (CDC$_3$) δ ppm: 3.78 (s, 2H), 7.23-7.32 (m, 1ArH), 7.44-7.61 (m, 5ArH). $^{13}$C NMR δ ppm: 36.52 (sp$^3$C), 120.75, 121.07, 125.30, 127.24, 128.00, 130.04, 132.81, 139.17, 139.59, 144.40, 144.84, (sp$^2$C). Anal. Calcd. for C$_{13}$H$_8$BrCl: C, 55.85; H, 2.88; Br, 28.58; Cl, 12.68%. Found: C, 55.76; H, 2.87; Br, 28.76; Cl, 12.55%.

Example 31.
7-Bromo-2-chloro-9,9-diethyl-9H-fluorene

To a mixture of 7-chloro-2-bromofluorene (55.91 g, 0.2 mol), DMSO (150 mL), powdered potassium hydroxide (56.1 g, 1.0 mol), and potassium iodide (1.66 g, 0.01 mol), bromoethane (32.82 mL, 0.44 mol) was added dropwise at 12° C. After 18 hours at room temperature, the mixture was poured into water and the resulting slurry was filtered. The crude air-dried product was reslurried in ethanol (200 mL) to get colorless solids, 59.02 g (88% Yield), m.p. 133-135° C. Mass spec: m/z 378, 380, 382 (M+, dibromo), 334, 336, 338 (M+, chloro-bromo). Anal Calcd. for C$_{17}$H$_{16}$BrCl: C, 60.83; H, 4.72, Br, 23.80; Cl, 10.08%. Found: C, 60.52; H, 4.72; Br, 23.51; Cl, 10.08. $^1$H NMR (CDCl$_3$) δ ppm: 0.31 (t, J=7.4 Hz, 6H), 1.99 (q, J=7.4 Hz, 4H), 7.28-7.32 (m, 2H), 7.44-7.47 (m, 2H), 7.51-7.54 (m, 2H), 7.58 (d, J=8.0 Hz, 1H). $^{13}$C NMR: 8.54, 32.78, 56.83 (3 sp$^3$C), 120.87, 121.20, 121.24, 121.49, 121.63, 123.47, 126.40, 127.52, 130.34, 130.36, 133.46, 139.17, 139.61, 151.58, 151.88, 152.00 (16 sp$^2$C).

Example 32.
7-Chloro-9,9-diethyl-9H-fluorene-2-carbonitrile
(2008-58)

A mixture of chlorobromo-diethyl-fluorene (42.01 g, 0.125 mol), copper(I) cyanide (13.43 g, 0.15 mol) and DMF (150 mL) was held at 138° C. for 22 hours, cooled, and poured into water, and then filtered. The solids were resuspended in water, treated with ammonium hydroxide (28%, 250 mL), and the mixture was stirred with toluene (400 mL). The aqueous phase was separated and re-extracted with toluene. The combined toluene extract was washed with dilute ammonium hydroxide, and water, dried, and concentrated. The residue was suspended in 1:3 toluene-heptanes (200 mL), and the separated solids were collected, 3.12 g (8% yield), m.p. 167-169° C. This material is identified as 7-chloro-9,9-diethylflyorene-2-carboxamide. Mass spec: m/z 299, 301 (M+). The filtrate was transferred to a column of silica gel, and the column was eluted with a mixture of heptanes and toluene (1:1) to get the product, which was crystallized from pentane, 21.09 g (60% Yield), m.p. 87-89° C. Mass spec: m/z 281, 283 (M$^+$). Elution of the column with toluene-heptanes (3:1), gave 9,9-diethylfluorene-2,7-dinitrile, m.p. 157-159° C., 5.48 g (20% Yield). Mass spec: m/z 272 (M+).

Example 33. 7-(2-Isopropylphenylamino)-9,9-diethyl-9H-fluorene-2-carbonitrile (33) (2010-38)

A mixture of 7-chloro-9,9-diethylfluorene-2-nitrile (11.13 g, 39.45 mmol), 2-isopropyl aniline (7.45 g, 55 mmol), and toluene (110 mL) was azeotroped dry under nitrogen and cooled. Bis(dibenzylideneacetone)palladium(0) (376.1 mg (0.654 mmol), tri-t-butylphosphonium tetrafluoroborate (166.8 mg), and sodium-t-butoxide (4.62 g, 48 mmol) were added, and the mixture was held at 79-81° C. for 4.5 hours. After cooling and dilution with toluene, the toluene solution was washed with water, dried and concentrated. The residue (18.49 g) was chromatographed over silica gel, and elution with 65% toluene-heptane gave the product, 14.6 g (97%), m.p. 111.3-113° C. (hexanes). Mass spec: m/z 380 (M$^+$). Analysis: Calcd for C$_{27}$H$_{28}$N$_2$: C, 85.22; H, 7.42 and N, 7.36%. Found: C, 85.27; H, 7.44 and N, 7.26%. $^1$H NMR (CDCl$_3$) δ ppm: 0.33 (t, 6H, 7.30 Hz), 1.25 (d, 6H, 6.84 Hz), 1.94 (m, 4H), 3.2 (septet, 1H, 6.8 Hz), 5.68 (s, 1H), 6.78 (s, 1H), 6.84 (d, 1H, 8.12 Hz), 7.17 (m, 2H), 7.28 (d, 1H, 7.6 Hz), 7.35 (d, 1H, 7.4 Hz), 7.49 (s, 1H), 7.57 (m, 3H). $^{13}$C NMR δ ppm: 8.68, 23.42, 28.01, 32.87, 56.54 (5 sp3C), 108.06, 109.99, 115.52, 118.96, 120.56, 122.07, 123.33, 124.73, 126.34, 126.63, 128.88, 131.54, 131.73, 139.09, 142.13, 146.91, 147.33, 150.06, and 152.97 (19 sp$^2$- and sp-C).

Example 34. 7-(bis(2-isopropylphenyl)amino)-9,9-diethyl-9H-fluorene-2-carbonitrile (27a) (2010-46)

A mixture of 7-(2-isopropyl)-phenylamino-9,9-diethylfluorene-2-nitrile (7.6 g, 19.97 mmol), 2-isopropyliodobenzene (24.88 g, 101 m·mol), copper powder (3.13 g, 49.25 mmol), potassium carbonate (12.71 g, 92 mmol), 18-crown-6 (0.34 g, 1.29 mmol) and xylenes (5 mL) was held at 165-175° C. for 19 hours cooled, diluted with toluene and filtered. The filtrate was washed with water, dried and concentrated. The residual liquid (27.15 g) was chromatographed over silica gel, and elution with 3:1 heptane-toluene recovering first the unreacted iodobenzene. The product came out in 1:1 and 65% toluene-heptane eluates, and was recrystallized from isopropanol, 6.82 g (68%), m.p. 179.2-180.4° C. Mass spec: m/z 498 (M+). Analysis: Calcd for $C_{36}H_{38}N_2$: C, 86.70; H, 7.68 and N, 5.62%. Found: C, 86.61; H, 7.68, and N, 5.41%. $^1$H NMR (CDCl$_3$) δ ppm: 0.27 (t, 6H, 7.32 Hz), 1.04 (d, 12H, 6.36 Hz), 1.89 (m, 4H), 3.26 (q, 2H, 6.6 Hz), 6.67 (m, 2H), 6.97 (d, 2H, 7.64 Hz), 7.17 (m 2H), 7.21 (m, 2H), 7.35 (dd, 2H, 1.28 and 7.72 Hz), 7.49 (t, 2H, 5 Hz), 7.54 (m, 2H). $^{13}$C NMR δ ppm: 8.32, 23.48, 27.42, 32.44 and 56.36 (5 sp$^3$C), 108.15, 118.98, 120.14, 121.15, 125.87, 126.07, 126.73, 127.59, 128.36, 131.39, 132.18, 145.37, 146.37, 149.96, 151.91 and 152.55 (16 sp$^2$ and sp C).

Example 35. 7,7',7"-(1,3,5-triazine-2,4,6-triyl)tris(9,9-diethyl-N,N-bis(2-isopropylphenyl)-9H-fluoren-2-amine) (13A-1; AF452-2,2'-6iPr) (2010-52)

To ice cold trifluoromethane sulfonic acid (5.5 mL), 7-di-(2-isopropyl)-phenylamino-9,9-diethylfluorene-2-nitrile (3 g) was added and the mixture was stirred at room temperature for 44 hours. Chloroform (5 mL) was added, and the stirring continued for 24 hours after which the mixture was poured into ice and ammonium hydroxide. After chloroform was allowed to evaporate, the yellow solid (3 g) was collected and chromatographed over silica gel. Elution with 3:7 toluene-heptane gave the product which was recrystallized from a mixture of toluene and heptane, 2.62 g (87%), m.p. 281.2-283.7° C. Analysis: Calcd for $C_{108}H_{114}N_6$: C, 86.70; H, 7.68 and N, 5.62%. Found: C, 86.71, H, 7.36; and N, 7.23%. $^1$H NMR (CDCl$_3$) δ ppm: 0.38 (t, 18H, 7.2 Hz), 1.05 (d, 36 Hz, 6.68 Hz), 1.92 (sextet, 6H, 7.26 Hz), 2.15 (sextet, 6H, 7.26 Hz), 3.31 (septet, 6H, 6.68 Hz), 6.73 (m, 6H), 6.99 (d, 6H, 7.4 Hz), 7.16 (m, 12H), 7.35 (dd, 6H, 1.44 and 7.76 Hz), 7.58 (d, 3H, 7.4 Hz), 7.77 (d, 3H, 8.0 Hz), 8.66 (d, 3H, 1.08 Hz), 8.79 (dd, 3H, 1.44 and 7.96 Hz). $^{13}$C NMR δ ppm: 8.61, 23.51, 27.46, 32.69, 56.26 (5 sp$^3$C), 115.16, 118.70, 120.82, 122.99, 125.58, 126.66, 127.54, 128.37, 128.46, 133.80, 134.08, 145.38, 145.91, 146.20, 149.72, 151.89, 152.44, and 171.67 (18 sp$^2$C).

Example 36. 7-bromo-N-(2,6-diisopropylphenyl)-9,9-diethyl-9H-fluoren-2-amine (36) (2010-61)

A mixture of 2,7-dibromo-9,9-diethylfluorene (28.41 g, 74.76 mmol, 1.46 eq.), 2,6-di-isopropylaniline (9.0 g, 50.76 mmol), and toluene (250 mL) was azeotroped dry under nitrogen and cooled. Palladium(II) acetate (112.4 mg, 0.5 mmol), DPE Phos (401 mg, 0.74 mmol), and sodium t-butoxide (4.97 g, 51.7 mmol) were added, and the mixture was held at 85° C. for 19 hours. Extraction by adding toluene and water, washing toluene phase with water, drying and evaporation left a residue (36.67 g), which was chromatographed over silica gel. Elution with heptane returned unused dibromofluorene, 11.85 g (42%), m.p. 158.3-160.3° C. The desired product eluted out of the column by 10 and 15% toluene-heptane, and was recrystallized from isopropanol, 14.12 g (58% yield), m.p 150.6-151.5° C. Mass spec: m/z 475, 477 (M$^+$). Analysis: Calcd for $C_{29}H_{34}$NBr: C, 73.10; H, 7.19; N, 2.94 and Br, 16.77%. Found: C, 73.06; H, 7.07; N, 2.54; and Br, 16.75%. 1H NMR (CDCl$_3$) δ ppm: 0.27 (t, 6H, 7.32 Hz), 1.14 (d, 12H, 6.88 Hz), 1.83 (m, 4H), 3.24 (septet, 2H, 6.88 Hz), 5.24 (s, 1H), 6.24 (s, 1H), 6.58 (d, 1H, 6.12 Hz), 7.30 (m, 6H), 7.45 (d, 1H, 8.12 Hz). 13C NMR: 8.28, 23.80, 28.28, 32.82, 56.20 (5 sp3C), 106.66, 112.67, 118.67, 119.34, 120.57, 123.95, 125.79, 127.42, 129.70, 130.78, 135.01, 141.30, 147.66, 148.55, 151.15, and 151.44 (16 sp$^2$C). Increased amount of dibromofluorene (1.92 molar equivalents) resulted in only a modest improvement in yield, 60%.

Example 37. 7-bromo-N-(2,6-diisopropylphenyl)-9,9-diethyl-N-phenyl-9H-fluoren-2-amine (22a) (2010-66)

(Method A): A mixture of diisopropylamino-bromofluorene (Example 36) (4.4 g, 9.23 mmol), bromobenzene (6.95 g, 44.3 mmol) and toluene (50 mL) was azeotroped dry under nitrogen and cooled. Bis(dibenzylideneacetone)palladium(0) (86.8 mg, 0.16 mmol), dppf (86.1 mg, 0.15 mmol) and sodium t-butoxide (1.54 g, 16 mmol) were added, and the mixture was held at 83° C. for 20 hours. TLC examination revealed partial conversion, and additional t-butoxide (2.5 g, 26 mmol) was added. After an additional reaction period of 48 hours, the reaction was worked up by extraction into toluene, and the residue (9.11 g) was chromatographed over silica gel. Elution with heptane yielded unreacted bromobenzene. The product was eluted with 5% toluene-heptane and was recrystallized from isopropanol, 1.10 g (22%), m.p. 156-157° C. Mass spec: m/z 551, 553 (M$^+$). Analysis: Calcd for $C_{35}H_{38}$NBr: C, 76.07; H, 6/93; N, 2.53 and Br, 14.46%. Found: C, 76.05; H, 6.86; N, 2.66 and Br, 14.61%. $^1$H NMR (CDCl$_3$) δ ppm: 0.33 (t, 6H, 7.32 Hz), 0.94 (dd, 12H, 2.52 and 6.88 Hz), 1.87 (m, 4H), 3.19 (septet, 2H, 6.84 hz), 6.87 (m, 2H), 7.02 (dd, 2H, 1.0 and 8.72 Hz), 7.09 (d, 1H, 2.08 Hz), 7.15 (m, 4H), 7.41 (m, 5H).

Method B via Ullmann Reaction. A mixture of 2,6-diisopropylamino diethyl bromofluorene (Example 36) (4.77 g, 10.0 mmol), iodobenzene (5.6 g, 27.4 mmol), potassium carbonate (3.78 g, 27.4 mmol), TDA-1 (0.9 g), copper powder (0.6 g, 9.44 mmol) and xylenes (10 mL), was held under nitrogen at 182° C. for 19 hours, cooled, diluted with toluene and filtered. The filtrate was washed with water, dried and concentrated. The residue (8.94 g) was chromatographed over silica gel, and the product was eluted with 5% toluene-heptane, and crystallized from isopropanol, 2.3 g (42%), m.p. 155-156° C. Mass spec: m/z 551, 553 (M+).

Example 38. 7,7',7''-(1,3,5-triazine-2,4,6-triyl)tris (N-(2,6-diisopropylphenyl)-9,9-diethyl-N-phenyl-9H-fluoren-2-amine) (13A-2; AF452-2,6-6iPr) (2010-78)

A solution of 7-bromo-2-(2,6-diisopropylphenyl)-phenylamino-fluorene (Example 37) (7.0 g, 12.67 mmol) in THF (85 mL) was cooled in dry-ice acetone bath. A solution of n-butyl lithium in hexanes (1.6 M, 8.0 mL, 12.8 mmol) was syringed in. The gel was allowed to warm to −40° C., and after 30 min, a solution of 2,4,6-trifluoro-1,3,5-triazine (0.5 mL) in THF (10 mL) was added dropwise. The mixture was allowed to come to room temperature, diluted with toluene, washed with water, the organic phase was dried and concentrated. The residue (11.08 g) was chromatographed over silica gel, and the product was eluted with 5:3 heptane-toluene and crystallized from a mixture of toluene and heptane, 4.78 g (76%), m.p. 290-292° C. Analysis: Calcd for $C_{108}H_{114}N_6$: C, 86.70; H, 7.68 and N, 5.62%. Found: C, 86.79; H, 7.74 and N, 5.83%. $^1$H NMR (CDCl$_3$) δ ppm: 0.43 (t, 18H, 7.24 Hz), 0.96 (d, 18H, 6.88 Hz), 0.99 (d, 18H, 6.84 Hz), 1.97 (m, 6H), 2.17 (m, 6H), 3.23 (septet, 6H, 6.78 Hz), 6.91 (t, 6H, 7.36 Hz), 7.07 (d, 6H, 8.48 Hz), 7.23 (m, 15H), 7.42 (t, 3H, 7.68 Hz), 7.62 (d, 3H, 8.28 Hz), 7.78 (d, 3H, 8.0 HZ, 8.68 (s, 3H), 8.81 (d, 3H, 8.0 Hz). $^{13}$C NMR δ ppm: 8.56, 23.81, 24.00, 28.35, 32.76, 56.21 (6 sp$^3$C), 114.30, 118.72, 119.39, 120.15, 120.85, 121.03, 122.99, 125.05, 128.49, 129.01, 133.85, 134.10, 139.76, 146.11, 147.34, 147.57, 148.54, 149.86, 152.44, and 171.64 (20 sp$^2$C).

What is claimed is:

1. A two-photon active compound having a structural formula:

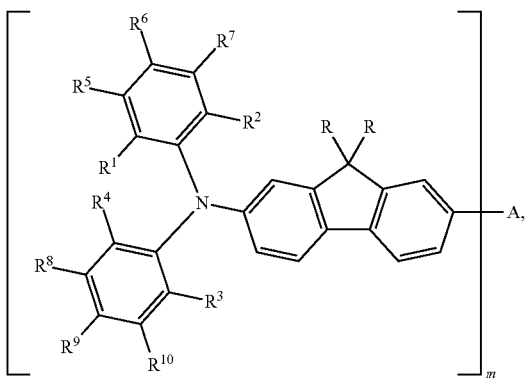

wherein A is an aromatic-heterocyclic π-electron acceptor moiety that is connected to m number of diarylaminofluorene arms (m=1-3); in each diarylaminofluorene arms, R is selected from linear or branched alkyl chains having a general formula $C_nH_{2n+1}$, where n is in a range from 2 to 25; wherein $R^1$, $R^2$, and $R^3$ are independently selected from the group consisting of H and C1-C5 alkyls; wherein $R^4$ is selected from the group consisting of C1-C5 alkyls; and wherein $R^5$ through $R^{10}$ are independently selected from the group consisting of H, alkoxyls, alkyls, and aryls.

2. The two-photon active compound of claim 1, wherein A is selected from the group consisting of benzothiazol-2-yl, benzo[1,2-d:4,5-d']bisthiazole-2,6-diyl, thiazolo[5,4-d]thiazole-2,5-diyl, 1,3,5-triazine-2,4,6-triyl, and benzo[1,2-d:3,4-d':5,6-d'']tristhiazole-2,5,8-triyl

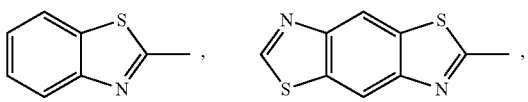

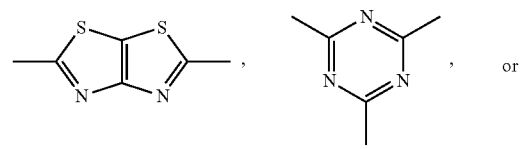

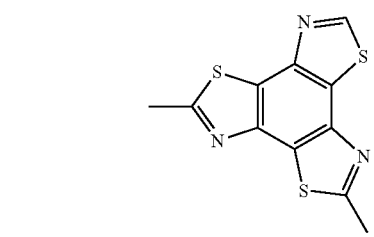

3. The two-photon active compound of claim 1, wherein the acceptor moiety is a benzothiazol-2-yl moiety, whereby the two-photon active compound has a structural formula:

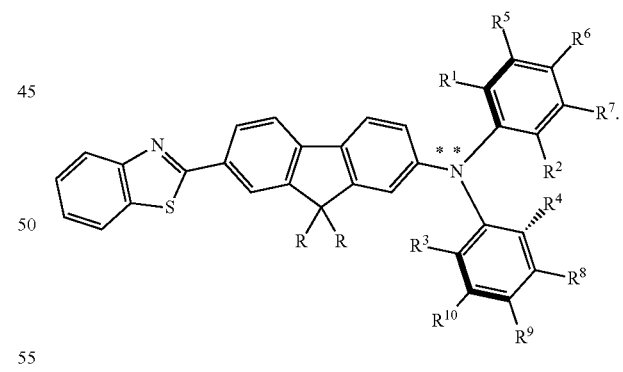

4. The two-photon active compound of claim 1, wherein n is in a range from 6 to 20.

5. The two-photon active compound of claim 4, wherein n is in a range from 10 to 15.

6. The two-photon active compound of claim 1, wherein $C_1$-$C_5$ alkyls are selected from the group consisting of methyl, ethyl, n-propyl, isopropyl, n-butyl, isobutyl, tert-butyl, n-pentyl, isopentyl, and neopentyl.

7. The two-photon active compound of claim 1, wherein $R^5$ through $R^{10}$ are H.

8. The two-photon active compound of claim 1, wherein the acceptor moiety is a 1,3,5-triazine-2,4,6-triyl moiety, whereby the two-photon active compound has a structural formula:

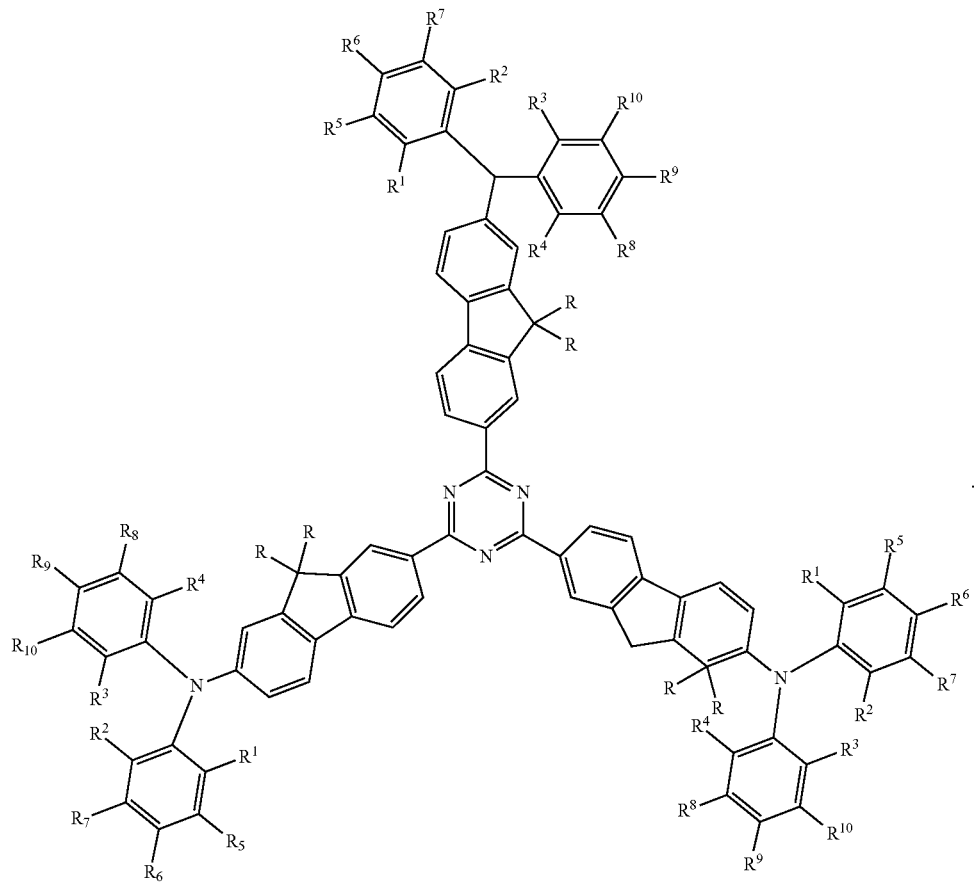

9. A method of synthesizing the two-photon active compound of claim 1, comprising:

reacting an amino-fluorene intermediate having a formula:

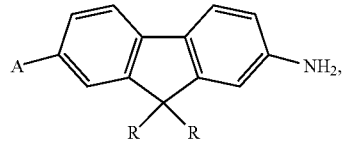

wherein R is selected from linear or branched alkyl chains having a general formula $C_nH_{2n+1}$, where n is in a range from 2 to 25, with an excess of an ortho-substituted aryl halide in the presence of a catalyst, wherein the ortho-substituted aryl halide comprises a $C_1$-$C_5$ alkyl substituent positioned ortho to a halide on a phenyl moiety.

10. The method of claim 9, wherein the acceptor moiety is a benzothiazole moiety, whereby the amino-fluorene intermediate has a structural formula:

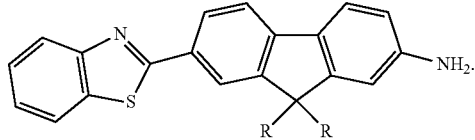

11. The method of claim 9, wherein the $C_1$-$C_5$ alkyl substituent is selected from the group consisting of methyl, ethyl, n-propyl, isopropyl, n-butyl, isobutyl, tert-butyl, n-pentyl, isopentyl, and neopentyl.

12. The method of claim 9, wherein the catalyst comprises one or more of copper(I) iodide, palladium (II) acetate, and bis(dibenzylidene acetone) palladium.

13. A method of synthesizing the two-photon active compound of claim 1, comprising:

reacting a halo-fluorene intermediate having a formula

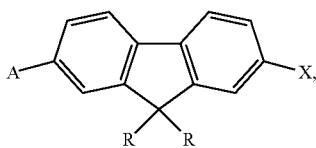

wherein R is selected from linear or branched alkyl chains having a general formula $C_nH_{2n+1}$, wherein n is in a range from 2 to 25, with an aniline derivative having a general formula:

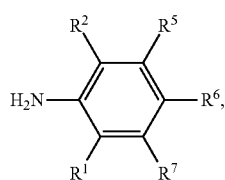

in the presence of a first catalyst to form a monoaryl-substituted amino fluorene intermediate; and reacting the monoaryl-substituted amino fluorene intermediate with an ortho-substituted aryl halide having a general formula:

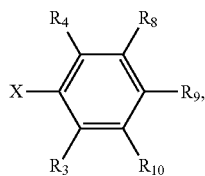

where X is bromide or iodide, in the presence of a second catalyst, and wherein the ortho-substituted aniline ($R_1$, $R_2$) and aryl halide ($R_3$, $R_4$) comprise a $C_1$-$C_5$ alkyl substituent positioned ortho to a halide on a phenyl moiety.

14. The method of claim 13, wherein the acceptor moiety is a benzothiazole moiety, whereby the halo-fluorene derivative has a structural formula:

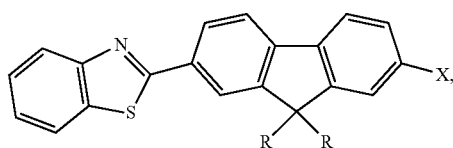

wherein R is selected from linear or branched alkyl chains having a general formula $C_nH_{2n+1}$, wherein n is in a range from 2 to 25.

15. The method of claim 13, wherein the first catalyst or the second catalyst comprises one or more of copper(I) iodide, palladium (II) acetate, and bis(dibenzylidene acetone) palladium.

16. A two-photon active compound having a structural formula:

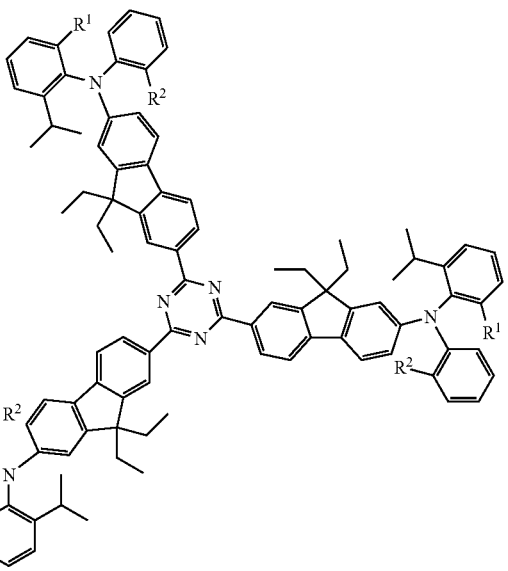

wherein $R^1$ is selected from is selected from the group consisting of H and isopropyl; wherein $R^2$ is selected from the group consisting of H, methyl, ethyl, t-butyl, and isopropyl.

17. The two-photon active compound of claim 16, wherein $R^1$ is H, and $R^2$ is selected from the group consisting of H and isopropyl.

18. The two-photon active compound of claim 16, wherein $R^1$ is isopropyl, and $R^2$ is isopropyl.

19. A method of synthesizing the two-photon active compound of claim 17, comprising:

reacting a chloro-fluorene-bromide having a formula

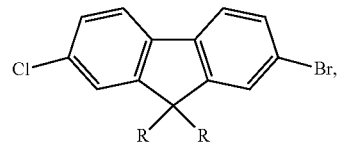

wherein R is selected from linear or branched alkyl chains having a formula $C_nH_{2n+1}$ where n is in a range from 2 to 25, with copper cyanide in DMF with heating to form a chloro-fluorene-nitrile intermediate having a formula

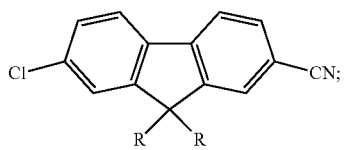

reacting the chloro-fluorene-nitrile intermediate with a 2-isopropyl aniline in the presence of a first catalyst to form a monoaryl-substituted amino fluorene nitrile intermediate having a formula

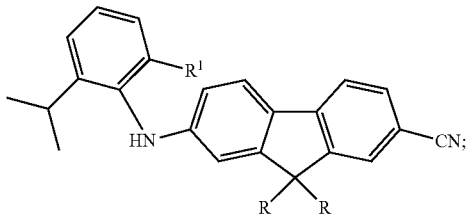

and
reacting the monoaryl-substituted amino fluorene nitrile intermediate with an ortho-substituted aryl halide having a formula:

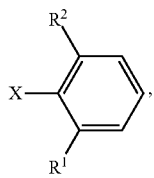

where X is bromide or iodide, and $R_1$ and $R_2$ are $C_1$-$C_5$ alkyl, in the presence of a second catalyst to form a diaryl-substituted-amino fluorene nitrile intermediate having a general formula

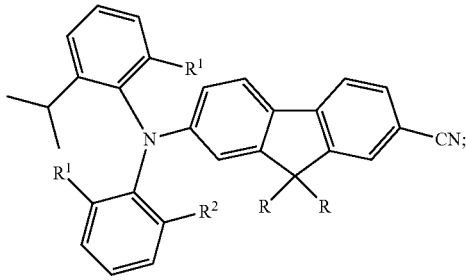

and
cyclotrimerizing the diaryl-substituted-amino fluorene nitrile intermediate in trifluoromethyl sulfonic acid.

20. A method of synthesizing the two-photon active compound of claim 18, comprising:
monoaminating a dibromodialkyl fluorene having a formula

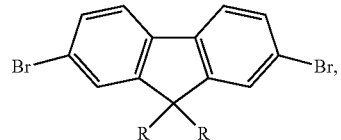

wherein R is selected from linear or branched alkyl chains having a formula $C_nH_{2n+1}$ where n is in a range from 2 to 25, with 2,6-diisopropylaniline in sodium t-butoxide (NaOBut) with heating to form an aniline-bromofluorene intermediate having a formula

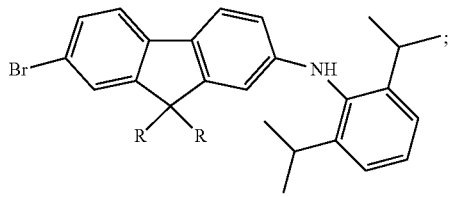

reacting the aniline-bromofluorene derivative with a 2-alkyl halo-benzene, where the halogen is bromide or iodide, in the presence of a catalyst to form a diarylamino-7-bromo-fluorene intermediate having a general formula

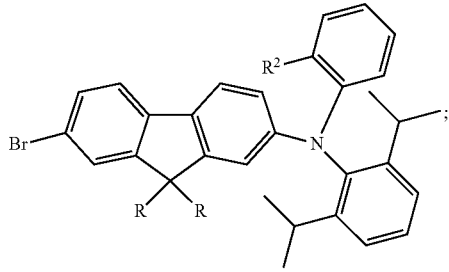

performing halogen-metal exchange with the diarylamino-7-bromo-fluorene intermediate with butyl-lithium, and performing triple aromatic nucleophilic displacement with 2,4,6-trifluoro-1,3,5-triazine.

* * * * *